US008975229B2

(12) United States Patent
Tsujikawa et al.

(10) Patent No.: US 8,975,229 B2
(45) Date of Patent: Mar. 10, 2015

(54) METHODS FOR TREATING A DISEASE CAUSED BY CHOROIDAL NEOVASCULARIZATION

(75) Inventors: Motokazu Tsujikawa, Osaka (JP); Yusuke Nakamura, Tokyo (JP); Takuya Tsunoda, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/377,110

(22) PCT Filed: Jun. 10, 2010

(86) PCT No.: PCT/JP2010/003871
§ 371 (c)(1),
(2), (4) Date: Mar. 8, 2012

(87) PCT Pub. No.: WO2010/143435
PCT Pub. Date: Dec. 16, 2010

(65) Prior Publication Data
US 2012/0156233 A1 Jun. 21, 2012

(30) Foreign Application Priority Data
Jun. 11, 2009 (JP) ................. 2009-140363

(51) Int. Cl.
| A61K 38/00 | (2006.01) |
| A61P 35/00 | (2006.01) |
| C07K 14/515 | (2006.01) |
| A61P 9/10 | (2006.01) |
| A61P 27/02 | (2006.01) |
| A61K 38/08 | (2006.01) |
| B60N 2/225 | (2006.01) |
| C07K 14/00 | (2006.01) |
| C07K 14/71 | (2006.01) |

(52) U.S. Cl.
CPC .............. *B60N 2/2252* (2013.01); *C07K 14/00* (2013.01); *C07K 14/71* (2013.01); *A61K 38/00* (2013.01)
USPC .......................... 514/13.3; 514/20.8; 514/21.6

(58) Field of Classification Search
None
See application file for complete search history.

(56) References Cited

U.S. PATENT DOCUMENTS

| 5,712,380 A | 1/1998 | Kendall et al. |
| 5,861,301 A | 1/1999 | Terman et al. |
| 6,348,333 B1 | 2/2002 | Niwa et al. |
| 6,383,486 B1 | 5/2002 | Davis-Smyth et al. |
| 7,514,084 B2 | 4/2009 | Tahara et al. |
| 7,556,809 B2 | 7/2009 | Romero et al. |
| 7,695,720 B2 | 4/2010 | Tahara et al. |
| 8,206,719 B2 | 6/2012 | Tahara et al. |
| 8,257,711 B2 | 9/2012 | Tahara et al. |
| 8,703,713 B2* | 4/2014 | Yamaue .................... 514/19.3 |
| 2005/0175624 A1 | 8/2005 | Romero et al. |
| 2005/0187241 A1 | 8/2005 | Wen et al. |
| 2006/0216301 A1 | 9/2006 | Tahara et al. |
| 2006/0234941 A1 | 10/2006 | Khleif et al. |
| 2008/0234941 A1 | 9/2008 | Jackson et al. |
| 2008/0254050 A1 | 10/2008 | Romero et al. |
| 2009/0214581 A1 | 8/2009 | Tahara et al. |
| 2009/0252752 A1 | 10/2009 | Tahara et al. |
| 2010/0047265 A1* | 2/2010 | Romero et al. ............ 424/185.1 |
| 2010/0184088 A1 | 7/2010 | Nakatsuru |
| 2010/0215676 A1 | 8/2010 | Tahara et al. |
| 2010/0297157 A1 | 11/2010 | Tamaki et al. |
| 2011/0082088 A1 | 4/2011 | Yamaue |
| 2011/0250219 A1 | 10/2011 | Tahara et al. |

FOREIGN PATENT DOCUMENTS

| CN | 1646153 A | 7/2005 |
| CN | 1694901 A | 9/2005 |
| EP | 0921193 A1 | 6/1999 |
| EP | 1086705 A1 | 3/2001 |
| EP | 1502599 A1 | 2/2005 |
| EP | 1548032 A1 | 6/2005 |
| EP | 2119447 A1 | 11/2009 |
| EP | 2261247 A2 | 12/2010 |
| EP | 2261248 A2 | 12/2010 |
| EP | 2261249 A2 | 12/2010 |
| EP | 2267021 A2 | 12/2010 |
| EP | 2267022 A2 | 12/2010 |
| EP | 2267023 A2 | 12/2010 |
| EP | 2270041 A2 | 1/2011 |
| EP | 2270042 A2 | 1/2011 |

(Continued)

OTHER PUBLICATIONS

Bicknell, et al., "Mechanisms and therapeutic implications of angiogenesis," *Curr Opin Oncol.*, vol. 8(1), pp. 60-65 (Jan. 1996).
Binetruy-Tournaire, et al., "Identification of a peptide blocking vascular endothelial growth factor (VEGF)-mediated angiogenesis" *Embo J.*, vol. 19(7), pp. 1525-1533 (Apr. 3, 2000).
Brown, et al., "Expression of Vascular Permeability Factor (Vascular Endothelial Growth Factor) and its Receptors in Breast Cancer," *Hum Pathol.*, vol. 26(1), pp. 86-91 (Jan. 1995).

(Continued)

*Primary Examiner* — Robert Landsman
(74) *Attorney, Agent, or Firm* — Kilpatrick Townsend & Stockton LLP

(57) ABSTRACT

The present invention provides novel pharmaceutical agents and methods for treating or preventing diseases caused by neovascularization in human choroid (neovascular maculopathy). The present invention provides pharmaceutical compositions and vaccines for treating and/or preventing diseases caused by neovascularization in human choroid (neovascular maculopathy), comprising at least one type each of a peptide comprising an amino acid sequence derived from a VEGFR-1 protein and having an activity of inducing cytotoxic T cells, and a peptide comprising an amino acid sequence derived from a VEGFR-2 protein and having an activity of inducing cytotoxic T cells.

22 Claims, 19 Drawing Sheets

(56) References Cited

FOREIGN PATENT DOCUMENTS

| | | |
|---|---|---|
| JP | 2006-501145 A | 1/2006 |
| JP | 2006-511475 A | 4/2006 |
| JP | 2006-315988 A | 11/2006 |
| JP | 2007-191485 A | 8/2007 |
| JP | 2008-531463 A | 8/2008 |
| WO | 94/11499 A1 | 5/1994 |
| WO | 94/21679 A1 | 9/1994 |
| WO | 98/11223 A1 | 3/1998 |
| WO | 98/31794 A1 | 7/1998 |
| WO | 98/58053 A1 | 12/1998 |
| WO | 99/40118 A1 | 8/1999 |
| WO | 99/43801 A1 | 9/1999 |
| WO | 99/59636 A1 | 11/1999 |
| WO | 01/12809 A2 | 2/2001 |
| WO | 02/056907 A2 | 7/2002 |
| WO | 03/028643 A2 | 4/2003 |
| WO | 03/086450 A1 | 10/2003 |
| WO | 2004/024766 A1 | 3/2004 |
| WO | 2004/027027 A2 | 4/2004 |
| WO | 2006/093030 A1 | 9/2006 |
| WO | 2008/099908 A1 | 8/2008 |
| WO | 2008/152816 A1 | 12/2008 |
| WO | 2009/028150 A1 | 3/2009 |

OTHER PUBLICATIONS

Bruns, et al., "Effect of the Vascular Endothelial Growth Factor Receptor-2 Antibody DC101 Plus Gemcitabine on Growth, Metastatis and Angiogenesis of Human Pancreatic Cancer Growing Orthotopically in Nude Mice," *Int J Cancer*, vol. 102(2), pp. 101-108 (Nov. 10, 2002).
Carmeliet, et al., Synergism between vascular endothelial growth factor and placental growth factor contributes to angiogenesis and plasma extravasation in pathological conditions, *Nat Med.*, vol. 7(5), pp. 575-583 (May 2001).
El-Mousawi, et al., "A Vascular Endothelial Growth Factor High Affinity Receptor 1-specific Peptide with Antiangiogenic Activity Identified Using a Phase Display Peptide Library," *J Biol Chem.*, vol. 278(47), pp. 46681-46691 (Nov. 21, 2003, Epub Sep. 2, 2003).
Ferrara, et al., "The Biology of Vascular Endothelial Growth Factor," *Endocrine Reviews*, vol. 18(1), pp. 4-25 (1997).
Flamme, et al., "Vascular Endothelial Growth Factor (VEGF) and VEGF Receptor 2 (flk-1) Are Expressed during Vasculogenesis and Vascular Differentiation in the Quail Embryo," *Dev Biol.*, vol. 169(2), pp. 699-712 (Jun. 1995).
Folkman, "Angiogenesis in cancer, vascular, rheumatoid and other disease," *Nat Med.*, vol. 1(1), pp. 27-31 (Jan. 1995).
Gehlbach, et al., "Periocular Gene Transfer of sFlt-1 Suppresses Ocular Neovascularization and Vascular Endothelial Growth Factor-Induced Breakdown of the Blood-Retinal Barrier," *Hum Gene Ther.*, vol. 14(2), pp. 129-141 (Jan. 20, 2003).
Gery, et al., "Autoimmunity in the eye and its regulation," *Curr Opin Immunol.*, vol. 6(6), pp. 938-945 (Dec. 1994).
Hazama, et al., "Peptide Vaccine for Colorectal Cancer, an Update," *Biotherapy*, vol. 25(6), pp. 857-861 (Nov. 2011).
Hou, et al., "Combination of Low-Dose Gemcitabine and Recombinant Quail Vascular Endothelial Growth Factor Receptor-2 as a Vaccine Induces Synergistic Antitumor Activities" *Oncology*, vol. 69(1), pp. 81-87 (2005, Epub Aug. 2, 2005).
Huang, et al., "Combined Therapy of Local and Metastatic 4T1 Breast Tumor in Mice Using SU6668, an Inhibitor of Angiogenic Receptor Tyrosine Kinases, and the Immunostimulator B7.2-IgG Fusion Protein," *Cancer Res.*, vol. 62(20), pp. 5727-5735 (Oct. 15, 2002).
Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).

Iunuma, et al., "Novel Peptide Vaccine Therapy Combined with Chemoradiation for Advanced or Recurrent Esophageal Cancer," *Biotherapy*, vol. 22(suppl-1), W8-3, p. 129 (Nov. 2008).
Kinose, et al., "Inhibition of retinal and choroidal neovascularization by a novel KDR kinase inhibitor," *Mol Vis.*, vol. 11, pp. 366-373 (May 27, 2005).
Klinkenbijl, et al., "Adjuvant Radiotherapy and 5-Fluorouracil After Curative Resection of Cancer of the Pancreas and Periampullary Region," *Ann Surg.*, vol. 230(6), pp. 776-782, discussion 782-784 (Dec. 1999).
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Krause, et al., "Vascular Endothelial Growth Factor Antisense Pretreatment of Bladder Cancer Cells Significantly Enhances the Cytotoxicity of Mitomycin C, Gemcitabine and Cisplatin," *J Urol.*, vol. 174(1), pp. 328-331 (Jul. 2005).
Kubo, et al., "Definition of Specific Peptide Motifs for Four Major HLA-A Alleles," *J Immunol.*, vol. 152(8), pp. 3913-3924 (Apr. 15, 1994).
Kwak, et al., "VEGF Is Major Stimulator in Model of Choroidal Neovascularization," *Invest Ophthalmol Vis Sci.*, vol. 41(10), pp. 3158-3164 (Sep. 2000).
Li, et al., "Active Immunization Against the Vascular Endothelial Growth Factor Receptor flk1 Inhibits Tumor Angiogenesis and Metastasis," *J Exp Med.*, vol. 195(12), pp. 1575-1584 (Jun. 17, 2002).
Liu, et al., "Immunotherapy of tumors with vaccine based on quail homologous vascular endothelial growth factor receptor-2," *Blood*, vol. 102(5), pp. 1815-1823 (Sep. 1, 2003, Epub May 15, 2003).
Lu, et al., "Complete Inhibition of Vascular Endothelial Growth Factor (VEGF) Activates with a Bifunctional Diabody Directed against Both VEGF Kinase Receptors, fms-like Tyrosine Kinase Receptor and Kinase Insert Domain-containing Receptor," *Cancer Res.*, vol. 61(19), pp. 7002-7008 (Oct. 1, 2001).
Luttun, et al., "Revascularization of ischemic tissues by PIGF treatment, and inhibition of tumor angiogenesis arthritis and atherosclerosis by anti-Flt1," *Nat Med.*, vol. 8(8), pp. 831-840 (Aug. 2002, Epub Jul. 1, 2002).
Lyden, et al., "Impaired recruitment of bone marrow-derived endothelial and hematopoietic precursor cells blocks tumor angiogenesis and growth," *Nat Med.*, vol. 7(11), pp. 1194-1201 (Nov. 2001).
Maeda, et al., "Detection of peptide-specific CTL-precursors in peripheral blood lymphocytes of cancer patients," *Br J Cancer*, vol. 87(7), 796-804 (Sep. 23, 2002).
Matsushita, et al., "Phase 1 Clinical Trial of Peptide Vaccine with UFT/LV for Advanced or Recurrent Colorectal Cancer," *Biotherapy*, vol. 24(5), pp. 394-402 (Sep. 2010).
Miyazawa, et al., "The combination therapy of an epitope peptide molecularly targeting VEGFR2 and gemcitabine for pancreatic cancer," *Suizo*, 23:267, S1-10 (2008).
Miyazawa, et al., "Phase 1 clinical trial using peptide vaccine for human vascular endothelial growth factor receptor 2 in combination with gemcitabine for patients with advanced pancreatic cancer," *Cancer Sci.*, vol. 101(2), pp. 433-439 (Feb. 2010, Epub Oct. 27, 2009).
Mochimaru, et al., "Suppression of Choroidal Neovascularization by Dendritic Cell Vaccination Targeting VEGFR2," *Invest Ophthalmol Vis Sci.*, vol. 48(10), pp. 4795-4801 (Oct. 2007).
Molina, et al., "Trastuzumab (Herceptin), a Humanized Anti-HER2 Receptor Monoclonal Antibody, Inhibits Basal and Activated HER2 Ectodomain Cleavage in Breast Cancer Cells," *Cancer Res.*, vol. 61(12), pp. 4744-4749 (Jun. 15, 2001).
Norgren, et al., EMBL Accession No. Q8SPP2, 1 page (Jun. 1, 2002).
Ogawa, et al., *Biotherapy*, vol. 24(2), pp. 129-137 (Mar. 2010).
Okuyama, et al., "Phase I Clinical Trial of Peptide Vaccine Therapy for Advanced or Metastatic Unresectable Pancreatic Cancer," *Biotherapy*, vol. 23(suppl-1), 0-13-3, p. 136 (Sep. 2009).
Park, et al., "Placenta Growth Factor," *J Biol Chem.*, vol. 269(41), pp. 25646-25654 (Oct. 14, 1994).
Plate, et al., "Vascular Endothelial Growth Factor and Glioma Angiogenesis: Coordinate Induction of Vegf Receptors, Distribution of Vegf Protein and Possible In Vivo Regulatory Mechanisms," *Int J Cancer*, vol. 59(4), pp. 520-529 (Nov. 15, 1994).

(56) References Cited

OTHER PUBLICATIONS

Shibuya, et al., "Nucleotide sequence and expression of a novel human receptor-type tyrosine kinase gene (flt) closely related to the fms family," *Oncogene*, vol. 5(4), pp. 519-524 (Apr. 1990).
Shibuya, et al., "Structure and Function of Vascular Endothelial Growth Factor Receptor-1 and -2," *Curr Top Microbiol Immunol.*, vol. 237, pp. 59-83 (1999).
Shinkai, et al., "Mapping of the Sites Involved in Ligand Association and Dissociation at the Extracellular Domain of the Kinase Insert Domain-containing Receptor for Vascular Endothelial Growth Factor," *J Biol Chem.*, vol. 273(47), pp. 31283-31288 (Nov. 20, 1998).
Stefanik, et al., "Monoclonal antibodies to vascular endothelial growth factor (VEGF) and the VEGF receptor, FLT-1, inhibit the growth of C6 glioma in a mouse xenograft," *J Neurooncol.*, vol. 55(2), pp. 91-100 (Nov. 2001).
Sun, et al., "Both farensyltransferase and geranylgeranyltransferase I inhibitors, are required for inhibition of oncogenic K-Ras prenylation but each alone is sufficient to suppress human tumor growth in nude mouse xenografts," *Oncogene*, vol. 16(11), pp. 1467-1473 (Mar. 1998).
Tahara, Slides for the symposium of the Japanese Cancer Association, *Slides for the Symposium of the Japanese Cancer Association*, 6 pages (Feb. 7, 2006).
Takayama, et al., "In vivo electroporation (IVE) of flt3-ligand plasmid DNA induces anti-tumor specific immunity by mobilization of dendritic cells in situ," *The American Association for Cancer Research/AACR*, vol. 44, #734, p. 168 (2003).
Tanaka, et al., "Immunogenicity and Specificity of HLA-A2.1-Restricted Peptides from Carcinogenic Antigen (CEA) and Nonspecific Cross-Reacting Antigen (NCA) in Transgenic Mice," *The American Association for Cancer Research/AACR*, vol. 42, #3669, pp. 681-682 (2001).
Tsunoda, et al., "Phase I clinical trial with VEGFR2-epitope peptides and gemcitabine for patients with advanced pancreatic cancer," *Proceedings 66th Annual Meeting of the Japanese Cancer Association*, SST5-5, pp. 256-257 (2007).
Uemura, et al., "Peptide Vaccination Therapy for Urologic Malignancies Refractory to Standard Treatments—Our Experiences and Future Aspect-," *Biotherapy*, vol. 24(5), pp. 365-374 (Sep. 2010).
Ueno, et al., "Prolonged Blockade of VEGF Family Members Does Not Cause Identifiable Damage to Retinal Neurons or Vessels," *J Cell Physiol.*, vol. 217(1). pp. 13-22 (Oct. 2008).
Umeki, et al., Database Uniprot, Q9SX54, 1 page (downloaded Apr. 1, 2011).
Wada, "Development of a new type of cancer immunotherapy that targets tumor angiogenesis," *Jpn J Gastroenterol Surg.*, vol. 58, #PP-2-606, p. 564 (2003).
Wada, "Development of a cancer vaccine therapy that targets tumor angiogenesis," *J Jpn Surg Soc.*, vol. 103, PS3124-3, p. 533 (2003).
Wada, "Development of a novel cancer vaccine targeting tumor angiogenesis," *Cancer Science* (*The 62nd Annual Meeting of the Japanese Cancer Association*, vol. 202(#2267-0P) (Aug. 25, 2003).
Wada, "Development of the new cancer vaccine treatment that can be opposed to escape mechanism of immunological," *Cancer Science* (*The 63rd Annual Meeting of the Japanese Cancer Association*), 95 Supplement, vol. 436(W-464) (Aug. 25, 2004).
Wada, "Mechanism for cancer immunotherapy with peptide vaccination targeting tumor angiogenesis," *Proceedings of the 64th Annual Meeting of the Japanese Cancer Association*, vol. 326(#W-471) (Aug. 15, 2005).
Wada, et al., "Development of cancer immunotherapy against tumor angiogenesis," *The American Association for Cancer Research/AACR*, vol. 44, #848, p. 167 (2003).
Wada, et al., "Rationale for Antiangiogenic Cancer Therapy with Vaccination Using Epitope Peptides Derived from Human Vascular Endothelial Growth Factor Receptor 2," *Cancer Res.*, vol. 65(11), pp. 4939-4946 (Jun. 1, 2005).

Waltenberger, et al., "Different Signal Transduction Properties of KDR and Flt1, Two Receptors for Vascular Endothelial Growth Factor," *J Biol Chem.*, vol. 269(43), pp. 26988-26995 (Oct. 28, 1994).
Wood, et al., "PTK787/ZK 222584, a Novel and Potent Inhibitor of Vascular Endothelial Growth Factor Receptor Tyrosine Kinases, Impairs Vascular Endothelial Growth Factor-induced Responses and Tumor Growth after Oral Administration," *Cancer Res.*, vol. 60(8), pp. 2178-2189 (Apr. 15, 2000).
Zhang, et al., "Recombinant anti-vascular endothelial growth factor fusion protein efficiently suppresses choroidal neovascularization in monkeys," *Mol Vis.*, 14, pp. 37-49 (Jan. 10, 2008).
Zierhut, et al., "Immunology of the skin and the eye," *Immunol Today*, vol. 17(10), pp. 448-450 (Oct. 1996).
U.S. Appl. No. 13/494,930, filed Jun. 12, 2012, 76 pages.
U.S. Appl. No. 13/494,933, filed Jun. 12, 2012, 76 pages.
U.S. Appl. No. 13/566,933, filed Aug. 3, 2012, 40 pages.
International Search Report for PCT/JP2010/003871, mailed Aug. 31, 2010, 5 pages.
Albuquerque et al., "Alternatively Spliced VEGF Receptor-2 is an Essential Endogenous Inhibitor of Lymphatic Vessels," *Nat Med* Sep. 2009; 15(9): 1023-1030.
Bowie et al., "Deciphering the Message in Protein Sequences: Tolerance to Amino Acid Substitutions," *Science*, vol. 247, Mar. 1990, 1306-1310.
Burgess et al., "Possible Dissociation of the Heparin-Binding and Mitogenic Activities of Heparin-Binding (Acidic Fibroblast) Growth Factor-1 From its Receptor-Binding Activities by Site-Directed Mutagenesis of a Single Lysine Residue," *The Journal of Cell Biology*, vol. 111, Nov. 1990, 2129-2138.
Dalbadie-McFarland, et al., "Oligonucleotide-Directed Mutagenesis as a General and Powerful Method for Studies of Protein Function," *Proc. Natl. Acad. Sci USA*, vol. 79, Nov. 1982, 6409-6413.
Dionne, et al., "Her-2/neu Altered Peptide Ligand-Induced CTL Responses: Implications for peptides with Increased HLA Affinity and T-Cell-Receptor Interaction," *Cancer Immunol. Immunother*, Apr. 2004, 53: 307-314.
Guba et al., "Rapamycin Inhibits Primary and Metastatic Tumor Growth by Antiangiogenesis: Involement of Vascular Endothelial Growth Factor," *Nature Medicine*, vol. 8, No. 2, Feb. 2002, 128-135.
Hoffmann, et al, "The Ability of Variant Peptides to Reverse the Nonresponsiveness of T Lymphocytes to the Wild-Type Sequence p53 $_{264-272}$ Epitope[1]," *J. Immunol.*, Feb. 2002, 168:3, 1338-47.
Ishida, "Immunotherapy Targeting VEGFR-2 for Prevention from Pathological Retinal Angiogenesis," *The Waksman Foundation of Japan, Inc.*, 2006, 55-62.
Mark et al., "Site-Specific Mutagenesis of the Human Fibroblast Interferon Gene," *Proc. Nat. Acad. Sci. USA*, vol. 81, Sep. 1984, 5662-5666.
Parker et al., "Scheme for Ranking Potential HLA-A2 Binding Peptides Based on Independent Binding of Individual Peptide Side-Chains," *J. Immunol*, Jan. 1994, 1:152(1), 163-175.
Pawson et al., "Assembly of Cell Regulatory Systems Through Protein Interaction Domains," *Science*, Apr. 2003, vol. 300, 445-452.
Streilein, "Ocular Immune Privilege: The eye Takes a Dim but Practical View of Immunity and Inflammation," *Journal of Leukocyte Biology*, vol. 74, Aug. 2003, 179-185.
Takahashi et al., "Suppression of Chroroidal Neovascularization by Vaccination with Epitope Peptide Derived from Human VEGF Receptor 2 in an Animal Model," *Invest Ophthalmol Vis Sci.* May 2008;49(5):2143-7.
Tsujikawa, et al., "Phase 1 Trial of Anti-VEGFR Vaccine Therapy for Neovascular Maculopathy," *Annual Meeting of American Academy of Ophthalmology*, 2012, P0484.
Zoller et al., "Oligonucleotide-Directed Mutagenesis using M13-Derived Vectors: An Eficient and General Procedure for the Production of Point Mutations in Any Fragment of DNA," *Nucleic Acids Res.* Oct. 25, 1982:10(20):6487-500.
U.S. Appl. No. 14/160,436, filed Jan. 21, 2014, 40 pages.

* cited by examiner

HLA-A0201-Case1 Pre-treatment

A

B

C

Fig. 1-2
HLA-A0201-Case1 5 months later after stating treatment
D
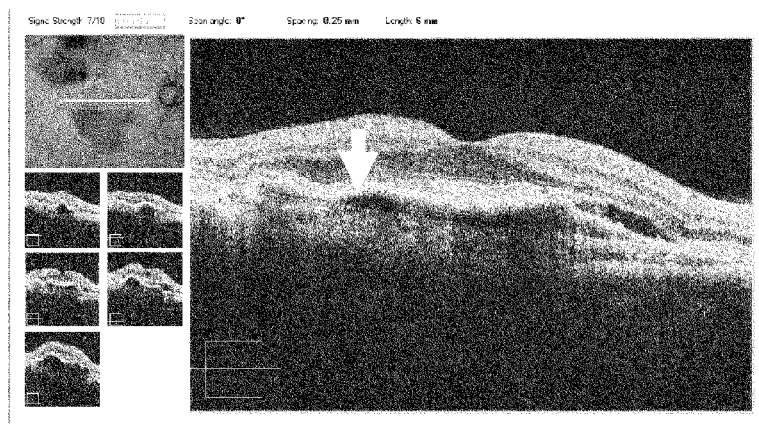
E
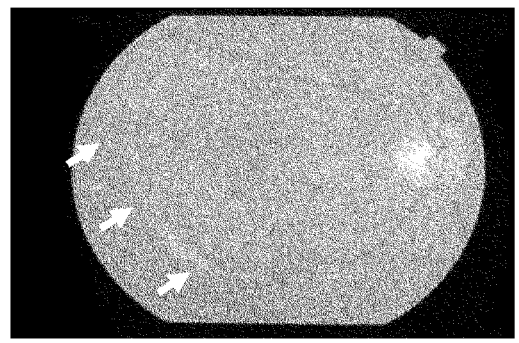
F
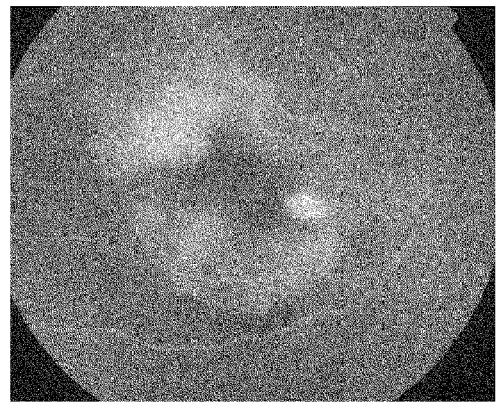

HLA-A0201-Case3

A Pre-treatment

B One month later after treatment

HLA-A2402-Case1 a A0201-Case 1. pre-treatment (VEGFR1)

b A0201-Case 1. post-1course (VEGFR1)

a  A0201-Case 1. pre-treatment (VEGFR2)

b  A0201-Case 1. post-1course (VEGFR2)

c  A0201-Case 1. post-2course (VEGFR2)

d  A0201-Case 1. post-3course (VEGFR2)

e  A0201-Case 1. post-4course (VEGFR2)

a  A0201-Case 3. post-1course (VEGFR1)

b  A0201-Case 3. post-3course (VEGFR1)

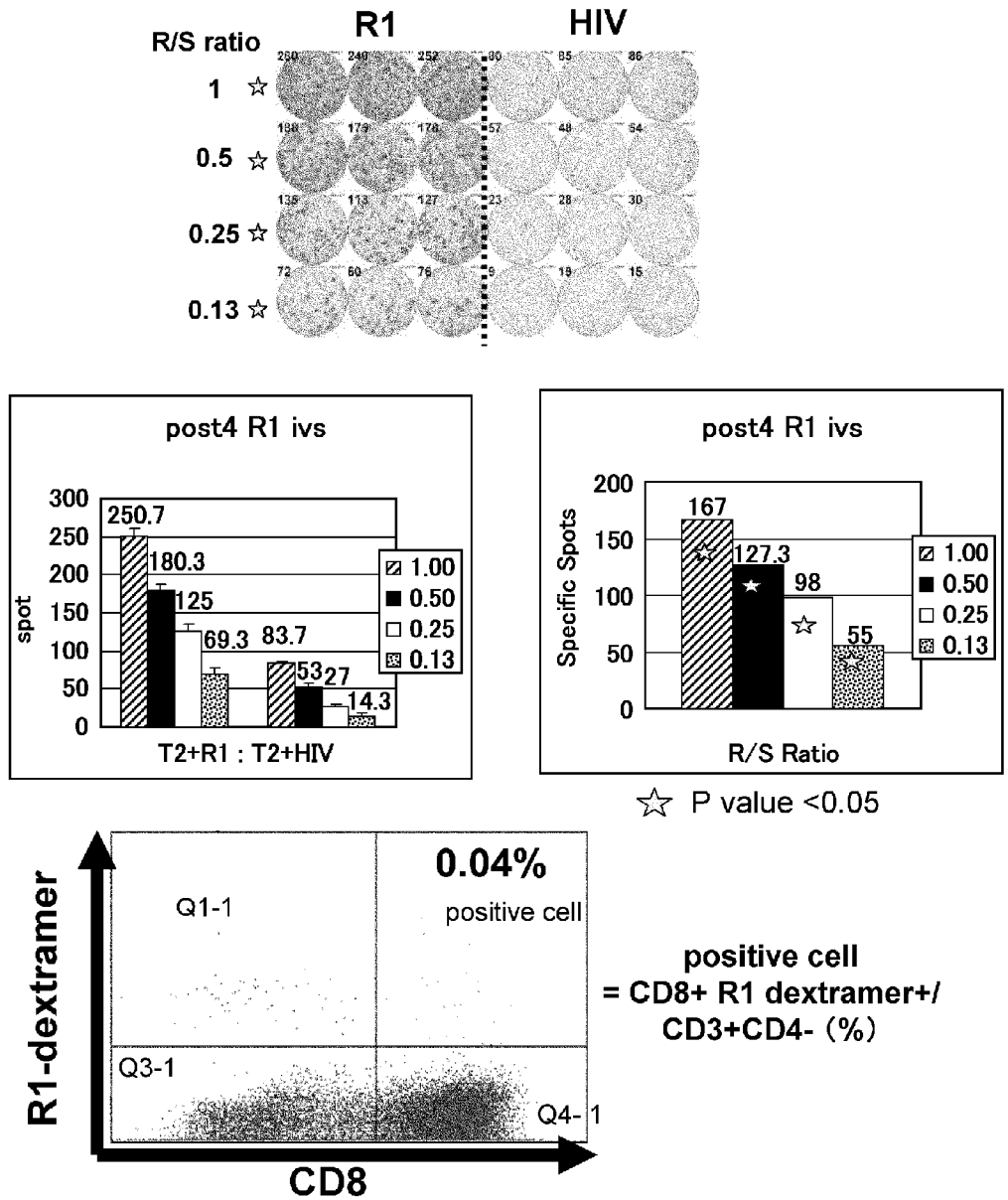

d  A0201-Case 3. post-5 course (VEGFR1)

Fig. 7-1
a A0201-Case 3. pre-treatment (VEGFR2)
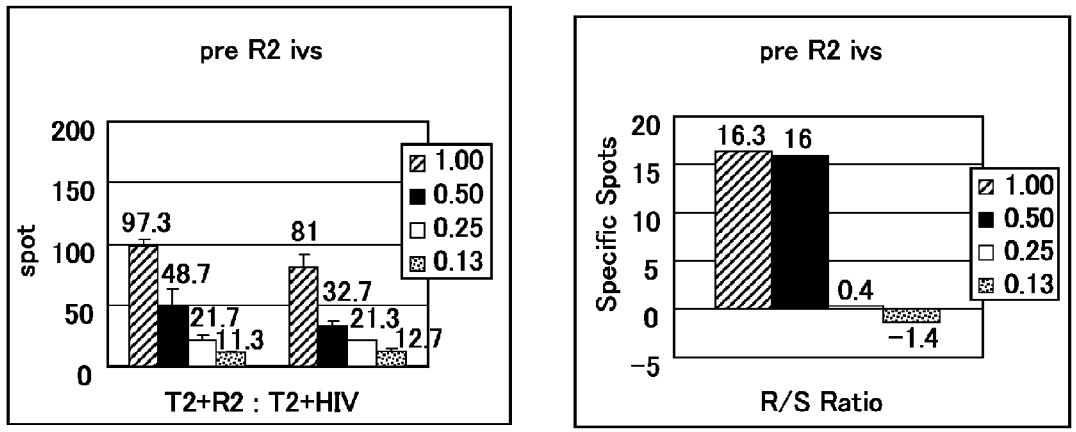
b A0201-Case 3. post-1course (VEGFR2)
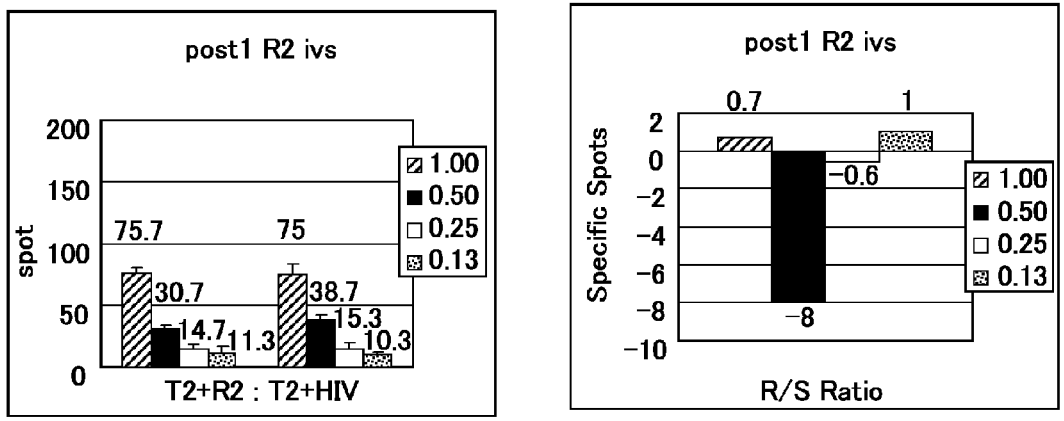
c A0201-Case 3. post-3course (VEGFR2)
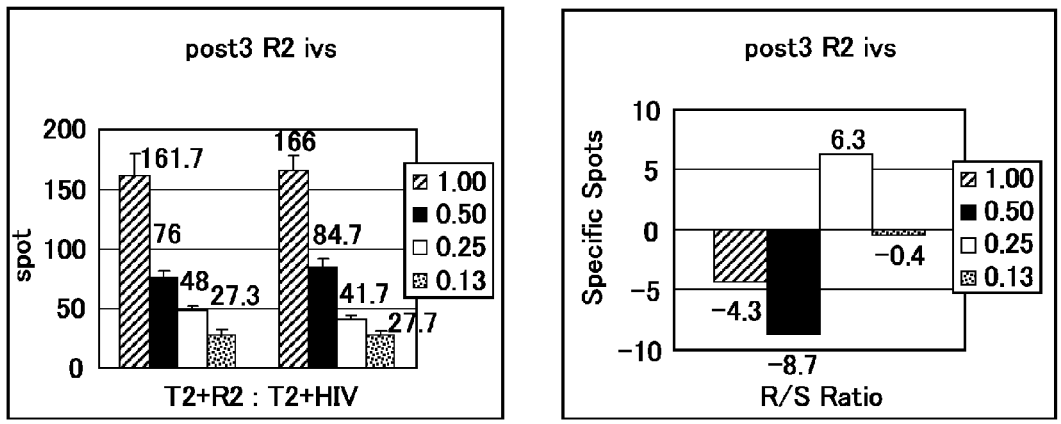

d  A0201-Case 3. post-4course (VEGFR2)

e  A0201-Case 3. post-5course (VEGFR2)

a  A2402-Case 1. post-2course (VEGFR1)

b  A2402-Case 1. post-6course (VEGFR1)

a A2402-Case 1. post-2course (VEGFR2)

b A2402-Case 1. post-6course (VEGFR2)

Change in vision after treatment

METHODS FOR TREATING A DISEASE CAUSED BY CHOROIDAL NEOVASCULARIZATION

PRIORITY

This application is a U.S. National Phase of PCT/JP2010/003871, filed Jun. 10, 2010, which claims the benefit of Japanese Patent Application Number. 2009-140363 filed Jun. 11, 2009, the contents of which are hereby incorporated herein by reference in their entirety for all purposes.

REFERENCE TO A SEQUENCE LISTING

This application includes a Sequence Listing as a text file named "SEQTXT 87331-027400US-825489.txt" created Dec. 7, 2011 and containing 44,327 bytes. The material contained in this text file is incorporated by reference in its entirety for all purposes.

TECHNICAL FIELD

This application claims the benefit of Japanese Patent Application Number. 2009-140363 filed Jun. 11, 2009, the contents of which are hereby incorporated herein by reference in their entirety for all purposes.

The present invention relates to pharmaceutical compositions and vaccines for treatment and/or prevention of diseases caused by neovascularization in the choroid (neovascular maculopathy). The present invention also relates to pharmaceutical compositions and vaccines for inhibiting neovascularization in the choroid.

BACKGROUND ART

Exudative age-related macular degeneration (AMD) caused by choroid neovascularization (CNV) is one of the major causes for severe visual impairment in developed countries. Evidence to date suggests that vascular endothelial growth factor (VEGF) plays a central role in the development of CNV. For example, it has been reported that CNV is suppressed by compounds that inhibit the production of VEGF or compounds that inhibit the signal transduction pathway of VEGF. Furthermore, it has also been reported that anti-VEGF antibodies show higher therapeutic efficacy compared to conventional therapeutic methods including photodynamic therapy. Therefore, in recent years, anti-VEGF agents have become a main option for drug therapy against CNV.

VEGF signaling is mediated by two types of receptor tyrosine kinases, i.e., VEGF receptor 1 (VEGFR-1) and VEGF receptor 2 (VEGFR-2). The two receptors are expressed on the human CNV membrane and the laboratory mouse CNV membrane. However, the role of VEGFR-1 signal transduction pathway in CNV is still controversial. For example, one study reports that the inhibition of VEGFR-1 signaling by oral administration of an antibody, gene knockdown, or siRNA inhibits CNV. Another study reports that in the eye, activation of VEGFR-1 by VEGF or placental growth factor 1 (PIGF1), which is a ligand of VEGFR-2, leads to activation of CNV via activation of VEGFR-2 by SPARC. On the other hand, for VEGFR-2, the finding that activation of VEGFR-2 signaling promotes CNV growth is generally accepted. Thus, antiangiogenic approaches targeting VEGFR-2, such as systemic or local administration of anti-VEGFR-2 agents or VEGFR-2 antibodies, and intravitreal administration of siRNA, are expected to inhibit VEGFR-2 signaling and CNV growth.

However, the problem with currently available anti-VEGF agents is that they need to be injected repeatedly at 4- to 6-week intervals. Furthermore, there is a high risk of severe complications such as endophthalmitis and retinal detachment. Therefore, it is desirable to establish a novel therapeutic method that replaces currently used anti-VEGF agents.

A vaccine using a peptide derived from human VEGF receptor 2 is known to induce cytotoxic T-lymphocytes (CTLs) in tumor tissues which have potent cytotoxicity against VEGFR-2-expressing endothelial cells (Patent Document 1). A vaccine using a peptide derived from human VEGF receptor 1 is also known to induce CTLs which have potent cytotoxicity against VEGFR-1-expressing endothelium (Patent Document 2). Furthermore, a vaccine using a peptide derived from VEGF receptor 2 has been confirmed to have CNV inhibitory effects in mice (Patent Document 3). However, as in other tissues, there are many unclear points in the mechanism of neovascularization in the choroid, and the presence of a vaccine that effectively inhibits CNV in human choroid is not known.

CITATION LIST

Patent Literature

[PTL 1] WO 2004/024766
[PTL 2] WO 2006/093030
[PTL 3] WO 2008/099908

SUMMARY OF INVENTION

Technical Problem

The present invention was achieved in view of the above circumstances. An objective to be achieved by the present invention is to provide novel pharmaceutical agents and methods for treating and/or preventing a disease caused by neovascularization in human choroid (neovascular maculopathy).

Solution to Problem

The present inventors administered a pharmaceutical composition/vaccine containing a VEGFR-1-derived peptide to neovascular maculopathy patients, and as a result discovered that this can effectively inhibit human CNV without causing problems suggestive of safety issue, and thereby completed the present invention.

More specifically, the present invention provides a pharmaceutical composition for treating and/or preventing a disease caused by neovascularization in human choroid (neovascular maculopathy), comprising as an active ingredient at least a peptide comprising an amino acid sequence derived from a VEGFR-1 protein and having an activity of inducing cytotoxic T cells, and/or a polynucleotide encoding thereof.

The present invention also provides a vaccine for treating and/or preventing a disease caused by neovascularization in human choroid, comprising as an active ingredient at least a peptide comprising an amino acid sequence derived from a VEGFR-1 protein and having an activity of inducing cytotoxic T cells, and/or a polynucleotide encoding thereof.

The present invention also provides a pharmaceutical composition for inhibiting neovascularization in human choroid, comprising as an active ingredient at least a peptide comprising an amino acid sequence derived from a VEGFR-1 protein and having an activity of inducing cytotoxic T cells, and/or a polynucleotide encoding thereof.

Furthermore, the present invention provides a vaccine for inhibiting neovascularization in human choroid, comprising as an active ingredient at least a peptide comprising an amino acid sequence derived from a VEGFR-1 protein and having an activity of inducing cytotoxic T cells, and/or a polynucleotide encoding thereof.

The present invention provides a method for treating and/or preventing a disease caused by neovascularization in human choroid, comprising the step of administering to a subject at least a peptide comprising an amino acid sequence derived from a VEGFR-1 protein and having an activity of inducing cytotoxic T cells, and/or a polynucleotide encoding thereof.

The present invention also provides a method for inhibiting neovascularization in human choroid, comprising the step of administering to a subject at least a peptide comprising an amino acid sequence derived from a VEGFR-1 protein and having an activity of inducing cytotoxic T cells, and/or a polynucleotide encoding thereof.

The present invention further provides use of a peptide comprising an amino acid sequence derived from a VEGFR-1 protein and having an activity of inducing cytotoxic T cells, and/or a polynucleotide encoding thereof in manufacturing a pharmaceutical composition for treating and/or preventing a disease caused by neovascularization in human choroid.

Furthermore, the present invention provides use of a peptide comprising an amino acid sequence derived from a VEGFR-1 protein and having an activity of inducing cytotoxic T cells, and/or a polynucleotide encoding thereof, in manufacturing a vaccine for treating and/or preventing a disease caused by neovascularization in human choroid.

The present invention also provides use of a peptide comprising an amino acid sequence derived from a VEGFR-1 protein and having an activity of inducing cytotoxic T cells, and/or a polynucleotide encoding thereof, in manufacturing a pharmaceutical composition for inhibiting neovascularization in human choroid.

In addition, the present invention provides use of a peptide comprising an amino acid sequence derived from a VEGFR-1 protein and having an activity of inducing cytotoxic T cells, and/or a polynucleotide encoding thereof, in manufacturing a vaccine for inhibiting neovascularization in human choroid.

The present invention further provides a peptide comprising an amino acid sequence derived from a VEGFR-1 protein and having an activity of inducing cytotoxic T cells for use in treating and/or preventing a disease caused by neovascularization in human choroid.

Alternatively, the present invention further provides a method or process for manufacturing a pharmaceutical composition for treating or preventing a disease caused by neovascularization in human choroid, wherein the method or process includes the step of formulating a pharmaceutically or physiologically acceptable carrier with an active ingredient of a peptide comprising an amino acid sequence derived from a VEGFR-1 protein and having an activity of inducing cytotoxic T cells, and/or a polynucleotide encoding thereof.

In another embodiment, the present invention also provides a method or process for manufacturing a pharmaceutical composition for treating or preventing a disease caused by neovascularization in human choroid, wherein the method or process includes the steps of admixing an active ingredient with a pharmaceutically or physiologically acceptable carrier, wherein the active ingredient is a peptide comprising an amino acid sequence derived from a VEGFR-1 protein and having an activity of inducing cytotoxic T cells, and/or a polynucleotide encoding thereof.

Alternatively, in one embodiment, in the present invention, VEGFR-1-derived peptide may also be administered in combination with a VEGFR-2-derived peptide for treating or inhibiting human CNV. Accordingly, the present invention provides a pharmaceutical composition for treating and/or preventing a disease caused by neovascularization in human choroid (neovascular maculopathy), comprising as an active ingredient at least one type each of a peptide selected from the group consisting of;

(a) a peptide comprising an amino acid sequence derived from a VEGFR-1 protein and having an activity of inducing cytotoxic T cells, and/or a polynucleotide encoding thereof, and (b) a peptide comprising an amino acid sequence derived from a VEGFR-2 protein and having an activity of inducing cytotoxic T cells, and/or a polynucleotide encoding thereof.

The present invention also provides a vaccine for treating and/or preventing a disease caused by neovascularization in human choroid, comprising as an active ingredient at least one type each of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

The present invention also provides a pharmaceutical composition for inhibiting neovascularization in human choroid, comprising as an active ingredient at least one type each of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

Furthermore, the present invention provides a vaccine for inhibiting neovascularization in human choroid, comprising as an active ingredient at least one type each of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

The present invention provides a method for treating and/or preventing a disease caused by neovascularization in human choroid, comprising the step of administering to a subject at least one type each of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

The present invention also provides a method for inhibiting neovascularization in human choroid, comprising the step of administering to a subject at least one type each of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

The present invention further provides use of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, in manufacturing a pharmaceutical composition for treating and/or preventing a disease caused by neovascularization in human choroid.

Furthermore, the present invention provides use of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, in manufacturing a vaccine, and/or a polynucleotide encoding thereof for treating and/or preventing a disease caused by neovascularization in human choroid.

The present invention also provides use of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, in manufacturing a pharmaceutical composition for inhibiting neovascularization in human choroid.

In addition, the present invention provides use of a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, in manufacturing a vaccine for inhibiting neovascularization in human choroid.

In addition, the present invention provides a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, for use in treating or preventing a disease caused by neovascularization in human choroid.

In addition, the present invention provides a peptide selected from the group consisting of;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, for use in inhibiting neovascularization in human choroid.

Alternatively, the present invention further provides a method or process for manufacturing a pharmaceutical composition for treating or preventing a disease caused by neovascularization in human choroid, wherein the method or process includes the step of formulating a pharmaceutically or physiologically acceptable carrier with an active ingredient selected from among;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, as active ingredients.

Alternatively, the present invention further provides a method or process for manufacturing a vaccine for inhibiting neovascularization in human choroid, wherein the method or process includes the step of formulating a pharmaceutically or physiologically acceptable carrier with an active ingredient selected from among;

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof, as active ingredients.

In another embodiment, the present invention also provides a method or process for manufacturing a pharmaceutical composition for treating or preventing a disease caused by neovascularization in human choroid, wherein the method or process includes the steps of admixing an active ingredient with a pharmaceutically or physiologically acceptable carrier, wherein the active ingredient is selected from among:

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

In another embodiment, the present invention also provides a method or process for manufacturing a vaccine for inhibiting neovascularization in human choroid, wherein the method or process includes the steps of admixing an active ingredient with a pharmaceutically or physiologically acceptable carrier, wherein the active ingredient is selected from among:

(a) a peptide comprising an amino acid sequence derived from a VEGFR-1 protein and having an activity of inducing cytotoxic T cells, and/or a polynucleotide encoding thereof and (b) a peptide comprising an amino acid sequence derived from a VEGFR-2 protein and having an activity of inducing cytotoxic T cells, and/or a polynucleotide encoding thereof.

More, specifically, the present invention provides the following [1] to [30];

[1] A pharmaceutical composition for treating and/or preventing a disease caused by neovascularization in human choroid (neovascular maculopathy), comprising as an active ingredient at least one type of the peptides of (a) peptides comprising an amino acid sequence derived from a VEGF receptor 1 protein and having an activity of inducing cytotoxic T cells, or a polynucleotide encoding thereof,

[2] The pharmaceutical composition of [1], wherein the above-mentioned peptides of (a) include the peptide of (i) and (ii) below:
(i) at least one peptide comprising any one of the amino acid sequence selected from the group consisting of SEQ ID NOs: 1 to 4;
(ii) at least one peptide comprising an amino acid sequence with one or more amino acid substitutions, deletions, additions, and/or insertions in any one of the amino acid sequence selected from the group consisting of SEQ ID NOs: 1 to 4,

[3] The pharmaceutical composition of [2], wherein the above-mentioned peptide of (ii) is any one of peptides of (1) to (6) below:
(1) a peptide in which the second amino acid from the N terminus of any one of amino acid sequence of SEQ ID NOs: 1 to 3 is leucine or methionine;
(2) a peptide in which the C-terminal amino acid of any one of amino acid sequence of SEQ ID NOs: 1 to 3 is valine or leucine;
(3) a peptide in which the second amino acid from the N terminus of any one of amino acid sequence of SEQ ID NOs: 1 to 3 is leucine or methionine, and the C-terminal amino acid of any one of amino acid sequence of SEQ ID NOs: 1 to 3 is valine or leucine;
(4) a peptide in which the second amino acid from the N terminus of the amino acid sequence of SEQ ID NO: 4 is phenylalanine, tyrosine, methionine, or tryptophan;
(5) a peptide in which the C-terminal amino acid of the amino acid sequence of SEQ ID NO: 4 is phenylalanine, leucine, isoleucine, tryptophan, or methionine; and
(6) a peptide in which the second amino acid from the N terminus of the amino acid sequence of SEQ ID NO: 4 is phenylalanine, tyrosine, methionine, or tryptophan and the C-terminal amino acid of the amino acid sequence of SEQ ID NO: 4 is phenylalanine, leucine, isoleucine, tryptophan, or methionine,

[4] The pharmaceutical composition of any one of [1] to [3], wherein the composition further comprises at least one type of the peptides of (b) peptides comprising an amino acid sequence derived from a VEGF receptor 2 protein and having an activity of inducing cytotoxic T cells,

[5] The pharmaceutical composition of [4], wherein the above-mentioned peptides of (b) include (i) and (ii) below:
(i) at least one peptide comprising any one of the amino acid sequence selected from the group consisting of SEQ ID NOs: 5 to 17; and
(ii) at least one peptide comprising an amino acid sequence with one or more amino acid substitutions, deletions, additions, and/or insertions in any one of the amino acid sequence selected from the group consisting of SEQ ID NOs: 5 to 17,

[6] The pharmaceutical composition of [5], wherein the above-mentioned peptide of (ii) is any one of peptides of (1) to (6) below:
(1) a peptide in which the second amino acid from the N terminus of any one of the amino acid sequence of SEQ ID NOs: 11 to 17 is leucine or methionine;
(2) a peptide in which the C-terminal amino acid of any one of the amino acid sequence of SEQ ID NOs: 11 to 17 is valine or leucine;
(3) a peptide in which the second amino acid from the N terminus of any one of the amino acid sequence of SEQ ID NOs: 11 to 17 is leucine or methionine and the C-terminal amino acid of any one of the amino acid sequence of SEQ ID NOs: 11 to 17 is valine or leucine;
(4) a peptide in which the second amino acid from the N terminus of any one of the amino acid sequence of SEQ ID NOs: 5 to 10 is phenylalanine, tyrosine, methionine, or tryptophan;
(5) a peptide in which the C-terminal amino acid of any one of the amino acid sequence of SEQ ID NOs: 5 to 10 is phenylalanine, leucine, isoleucine, tryptophan, or methionine; and
(6) a peptide in which the second amino acid from the N terminus of any one of the amino acid sequence of SEQ ID NOs: 5 to 10 is phenylalanine, tyrosine, methionine, or tryptophan and the C-terminal amino acid of any one of the amino acid sequence of SEQ ID NOs: 5 to 10 is phenylalanine, leucine, isoleucine, tryptophan, or methionine,

[7] The pharmaceutical composition of any one of [1] to [6], wherein the disease caused by neovascularization in the choroid (neovascular maculopathy) is selected from exudative age-related macular degeneration, myopic macular degeneration, angioid streaks, central exudative chorioretinopathy, various retinal pigment epitheliopathy, choroidal atrophy, choroideremia, and choroidal osteoma,

[8] The pharmaceutical composition of any one of [1] to [7], which is administered to a subject whose HLA antigen is HLA-A02 or HLA-A24,

[9] A vaccine for treating and/or preventing a disease caused by neovascularization in human choroid (neovascular maculopathy), comprising as an active ingredient at least one type of the peptides of (a) peptides comprising an amino acid sequence derived from a VEGF receptor 1 protein and having an activity of inducing cytotoxic T cells, or a polynucleotide encoding thereof,

[10] The vaccine of [9], wherein the above-mentioned peptides of (a) include the peptide of (i) and (ii) below:
(i) at least one peptide comprising any one of the amino acid sequence selected from the group consisting of SEQ ID NOs: 1 to 4; and
(ii) at least one peptide comprising an amino acid sequence with one or more amino acid substitutions, deletions, additions, and/or insertions in any one of the amino acid sequence selected from the group consisting of SEQ ID NOs: 1 to 4,

[11] The vaccine of [10], wherein the above-mentioned peptide of (ii) is any one of peptides of (1) to (6) below:
(1) a peptide in which the second amino acid from the N terminus of any one of amino acid sequence of SEQ ID NOs: 1 to 3 is leucine or methionine;
(2) a peptide in which the C-terminal amino acid of any one of amino acid sequence of SEQ ID NOs: 1 to 3 is valine or leucine;
(3) a peptide in which the second amino acid from the N terminus of any one of amino acid sequence of SEQ ID NOs: 1 to 3 is leucine or methionine, and the C-terminal amino acid of any one of amino acid sequence of SEQ ID NOs: 1 to 3 is valine or leucine;
(4) a peptide in which the second amino acid from the N terminus of the amino acid sequence of SEQ ID NO: 4 is phenylalanine, tyrosine, methionine, or tryptophan;
(5) a peptide in which the C-terminal amino acid of the amino acid sequence of SEQ ID NO: 4 is phenylalanine, leucine, isoleucine, tryptophan, or methionine; and
(6) a peptide in which the second amino acid from the N terminus of the amino acid sequence of SEQ ID NO: 4 is phenylalanine, tyrosine, methionine, or tryptophan and the C-terminal amino acid of the amino acid sequence of SEQ ID NO: 4 is phenylalanine, leucine, isoleucine, tryptophan, or methionine,

[12] The vaccine of any one of [9] to [11], wherein the vaccine further comprises at least one type of the peptides of (b) peptides comprising an amino acid sequence derived from a VEGF receptor 2 protein and having an activity of inducing cytotoxic T cells,

[13] The vaccine of [12], wherein the above-mentioned peptides of (b) include (i) and (ii) below:
(i) at least one peptide comprising the amino acid sequence of any one of SEQ ID NOs: 5 to 17; and
(ii) at least one peptide comprising an amino acid sequence with one or more amino acid substitutions, deletions, additions, and/or insertions in any one of the amino acid sequence selected from the group consisting of SEQ ID NOs: 5 to 17,

[14] The vaccine of [13], wherein the above-mentioned peptide of (ii) is any one of peptides of (1) to (6) below:
(1) a peptide in which the second amino acid from the N terminus of any one of the amino acid sequence of SEQ ID NOs: 11 to 17 is leucine or methionine;
(2) a peptide in which the C-terminal amino acid of any one of the amino acid sequence of SEQ ID NOs: 11 to 17 is valine or leucine;
(3) a peptide in which the second amino acid from the N terminus of any one of the amino acid sequence of SEQ ID NOs: 11 to 17 is leucine or methionine and the C-terminal amino acid of any one of the amino acid sequence of SEQ ID NOs: 11 to 17 is valine or leucine;
(4) a peptide in which the second amino acid from the N terminus of any one of the amino acid sequence of SEQ ID NOs: 5 to 10 is phenylalanine, tyrosine, methionine, or tryptophan;
(5) a peptide in which the C-terminal amino acid of any one of the amino acid sequence of SEQ ID NOs: 5 to 10 is phenylalanine, leucine, isoleucine, tryptophan, or methionine; and
(6) a peptide in which the second amino acid from the N terminus of any one of the amino acid sequence of SEQ ID NOs: 5 to 10 is phenylalanine, tyrosine, methionine, or tryptophan and the C-terminal amino acid of any one of the amino acid sequence of SEQ ID NOs: 5 to 10 is phenylalanine, leucine, isoleucine, tryptophan, or methionine,

[15] The vaccine of any one of [9] to [14], wherein the disease caused by neovascularization in the choroid (neovascular maculopathy) is selected from exudative age-related macular degeneration, myopic macular degeneration, angioid streaks, central exudative chorioretinopathy, various retinal pigment epitheliopathy, choroidal atrophy, choroideremia, and choroidal osteoma,

[16] The vaccine of any one of [9] to [15], which is administered to a subject whose HLA antigen is HLA-A02 or HLA-A24,

[17] A pharmaceutical composition for inhibiting neovascularization in human choroid, comprising as an active ingredient at least one type of the peptides of (a) peptides comprising an amino acid sequence derived from a VEGF receptor 1 protein and having an activity of inducing cytotoxic T cells, or a polynucleotide encoding thereof,

[18] The pharmaceutical composition of [17], wherein the above-mentioned peptides of (a) include the peptide of (i) and (ii) below:
(i) at least one peptide comprising any one of the amino acid sequence selected from the group consisting of SEQ ID NOs: 1 to 4; and
(ii) at least one peptide comprising an amino acid sequence with one or more amino acid substitutions, deletions, additions, and/or insertions in any one of the amino acid sequence selected from the group consisting of SEQ ID NOs: 1 to 4,

[19] The pharmaceutical composition of [18], wherein the above-mentioned peptide of (ii) is any one of peptides of (1) to (6) below:
(1) a peptide in which the second amino acid from the N terminus of any one of amino acid sequence of SEQ ID NOs: 1 to 3 is leucine or methionine;
(2) a peptide in which the C-terminal amino acid of any one of amino acid sequence of SEQ ID NOs: 1 to 3 is valine or leucine;
(3) a peptide in which the second amino acid from the N terminus of any one of amino acid sequence of SEQ ID NOs: 1 to 3 is leucine or methionine, and the C-terminal amino acid of any one of amino acid sequence of SEQ ID NOs: 1 to 3 is valine or leucine;
(4) a peptide in which the second amino acid from the N terminus of the amino acid sequence of SEQ ID NO: 4 is phenylalanine, tyrosine, methionine, or tryptophan;
(5) a peptide in which the C-terminal amino acid of the amino acid sequence of SEQ ID NO: 4 is phenylalanine, leucine, isoleucine, tryptophan, or methionine; and
(6) a peptide in which the second amino acid from the N terminus of the amino acid sequence of SEQ ID NO: 4 is phenylalanine, tyrosine, methionine, or tryptophan and the C-terminal amino acid of the amino acid sequence of SEQ ID NO: 4 is phenylalanine, leucine, isoleucine, tryptophan, or methionine,

[20] The pharmaceutical composition of any one of [17] to [19], wherein the composition further comprises at least one type of the peptides of (b) peptides comprising an amino acid sequence derived from a VEGF receptor 2 protein and having an activity of inducing cytotoxic T cells,

[21] The pharmaceutical composition of [20], wherein the above-mentioned peptides of (b) include (i) and (ii) below:
(i) at least one peptide comprising the amino acid sequence of any one of SEQ ID NOs: 5 to 17; and
(ii) at least one peptide comprising an amino acid sequence with one or more amino acid substitutions, deletions, additions, and/or insertions in any one of the amino acid sequence selected from the group consisting of SEQ ID NOs: 5 to 17,

[22] The pharmaceutical composition of [21], wherein the above-mentioned peptide of (ii) is any one of peptides of (1) to (6) below:
(1) a peptide in which the second amino acid from the N terminus of any one of the amino acid sequence of SEQ ID NOs: 11 to 17 is leucine or methionine;
(2) a peptide in which the C-terminal amino acid of any one of the amino acid sequence of SEQ ID NOs: 11 to 17 is valine or leucine;
(3) a peptide in which the second amino acid from the N terminus of any one of the amino acid sequence of SEQ ID NOs: 11 to 17 is leucine or methionine and the C-terminal amino acid of any one of the amino acid sequence of SEQ ID NOs: 11 to 17 is valine or leucine;
(4) a peptide in which the second amino acid from the N terminus of any one of the amino acid sequence of SEQ ID NOs: 5 to 10 is phenylalanine, tyrosine, methionine, or tryptophan;
(5) a peptide in which the C-terminal amino acid of any one of the amino acid sequence of SEQ ID NOs: 5 to 10 is phenylalanine, leucine, isoleucine, tryptophan, or methionine; and (6) a peptide in which the second amino acid from the N terminus of any one of the amino acid sequence of SEQ ID NOs: 5 to 10 is phenylalanine, tyrosine, methionine, or tryptophan and the C-terminal amino acid of any one of the amino acid sequence of SEQ ID NOs: 5 to 10 is phenylalanine, leucine, isoleucine, tryptophan, or methionine,

[23] The pharmaceutical composition of any one of [15] to [19], which is administered to a subject whose HLA antigen is HLA-A02 or HLA-A24,

[24] A vaccine for inhibiting neovascularization in human choroid, comprising as an active ingredient at least one type of the peptides of (a) peptides comprising an amino acid sequence derived from a VEGF receptor 1 protein and having an activity of inducing cytotoxic T cells, or a polynucleotide encoding thereof,

[25] The vaccine of [24], wherein the above-mentioned peptides of (a) include the peptide of (i) and (ii) below:

(i) at least one peptide comprising any one of the amino acid sequence selected from the group consisting of SEQ ID NOs: 1 to 4; and (ii) at least one peptide comprising an amino acid sequence with one or more amino acid substitutions, deletions, additions, and/or insertions in any one of the amino acid sequence selected from group consisting of SEQ ID NOs: 1 to 4,

[26] The vaccine of [25], wherein the above-mentioned peptide of (ii) is any one of peptides of (1) to (6) below:

(1) a peptide in which the second amino acid from the N terminus of any one of amino acid sequence of SEQ ID NOs: 1 to 3 is leucine or methionine;

(2) a peptide in which the C-terminal amino acid of any one of amino acid sequence of SEQ ID NOs: 1 to 3 is valine or leucine;

(3) a peptide in which the second amino acid from the N terminus of any one of amino acid sequence of SEQ ID NOs: 1 to 3 is leucine or methionine, and the C-terminal amino acid of any one of amino acid sequence of SEQ ID NOs: 1 to 3 is valine or leucine;

(4) a peptide in which the second amino acid from the N terminus of the amino acid sequence of SEQ ID NO: 4 is phenylalanine, tyrosine, methionine, or tryptophan;

(5) a peptide in which the C-terminal amino acid of the amino acid sequence of SEQ ID NO: 4 is phenylalanine, leucine, isoleucine, tryptophan, or methionine; and (6) a peptide in which the second amino acid from the N terminus of the amino acid sequence of SEQ ID NO: 4 is phenylalanine, tyrosine, methionine, or tryptophan and the C-terminal amino acid of the amino acid sequence of SEQ ID NO: 4 is phenylalanine, leucine, isoleucine, tryptophan, or methionine,

[27] The vaccine of any one of [24] to [26], wherein the vaccine further comprises at least one type of the peptides of (b) peptides comprising an amino acid sequence derived from a VEGF receptor 2 protein and having an activity of inducing cytotoxic T cells,

[28] The vaccine of [27], wherein the above-mentioned peptides of (b) include the peptide of (i) and (ii) below:

(i) at least one peptide comprising the amino acid sequence of any one of SEQ ID NOs: 5 to 17; and (ii) at least one peptide comprising an amino acid sequence with one or more amino acid substitutions, deletions, additions, and/or insertions in any one of the amino acid sequence selected from the group consisting of SEQ ID NOs: 5 to 17,

[29] The vaccine of [28], wherein the above-mentioned peptide of (ii) is any one of peptides of (1) to (6) below:

(1) a peptide in which the second amino acid from the N terminus of any one of the amino acid sequence of SEQ ID NOs: 11 to 17 is leucine or methionine;

(2) a peptide in which the C-terminal amino acid of any one of the amino acid sequence of SEQ ID NOs: 11 to 17 is valine or leucine;

(3) a peptide in which the second amino acid from the N terminus of any one of the amino acid sequence of SEQ ID NOs: 11 to 17 is leucine or methionine and the C-terminal amino acid of any one of the amino acid sequence of SEQ ID NOs: 11 to 17 is valine or leucine;

(4) a peptide in which the second amino acid from the N terminus of any one of the amino acid sequence of SEQ ID NOs: 5 to 10 is phenylalanine, tyrosine, methionine, or tryptophan;

(5) a peptide in which the C-terminal amino acid of any one of the amino acid sequence of SEQ ID NOs: 5 to 10 is phenylalanine, leucine, isoleucine, tryptophan, or methionine; and (6) a peptide in which the second amino acid from the N terminus of any one of the amino acid sequence of SEQ ID NOs: 5 to 10 is phenylalanine, tyrosine, methionine, or tryptophan and the C-terminal amino acid of any one of the amino acid sequence of SEQ ID NOs: 5 to 10 is phenylalanine, leucine, isoleucine, tryptophan, or methionine, and

[30] The vaccine of any one of [24] to [29], which is administered to a subject whose HLA antigen is HLA-A02 or HLA-A24.

Advantageous Effects of Invention

The present invention can provide pharmaceutical compositions and vaccines effective for treating and preventing diseases caused by neovascularization in human choroid (neovascular maculopathy). Furthermore, the present invention can provide pharmaceutical compositions and vaccines effective for inhibiting neovascularization in human choroid.

DESCRIPTION OF EMBODIMENTS

Definitions

Figure 1:
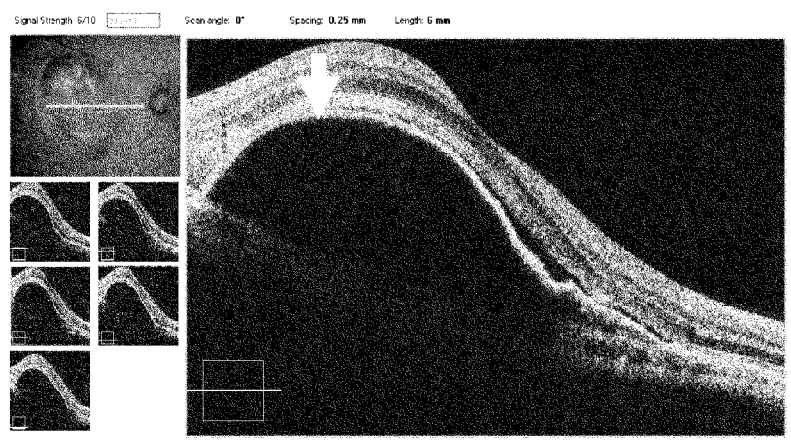
FIG. 1A-1C show the symptomatic relief of an age-related macular degeneration patient HLA-A0201-Case 1 who has been given a VEGFR-1-derived peptide and a VEGFR-2-derived peptide. (A) shows the tomographic images before starting the administration, (B) shows ocular fundus photographs before starting the administration, (C) shows fluorescein fundus photography before starting the administration. The arrows of (A) and (D) indicate the line of the pigment epithelium and of (B) and (E) indicate the detachment of the pigment epithelium.
FIG. 1D-1F show the symptomatic relief of an age-related macular degeneration patient HLA-A0201-Case 1 who has been given a VEGFR-1-derived peptide and a VEGFR-2-derived peptide. (D) shows the tomographic images five months after starting the administration, (E) shows the ocular fundus photograph five months after starting the administration, (F) shows fluorescein fundus photography five months after starting the administration. The arrows of (A) and (D) indicate the line of the pigment epithelium and of (B) and (E) indicate the detachment of the pigment epithelium.
Figure 1:
Figure 1:
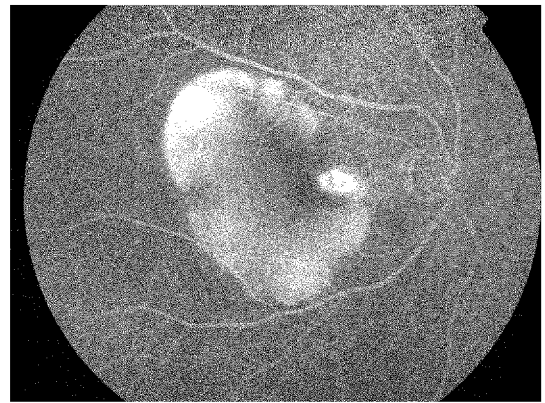

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are referred to by their commonly accepted single-letter codes.

The term "composition" as used herein is intended to encompass a product including the specified ingredients in the specified amounts, as well as any product that results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the phrase "pharmaceutical composition" encompasses any composition made by admixing a compound of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the active ingredient(s) from one organ, or portion of the body, to another organ, or portion of the body.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., virus-infected cells) and inducing the death of such cells.

Unless otherwise defined, the terms "HLA-A24" refers to the HLA-A24 type containing the subtypes such as HLA-A*2402.

Unless otherwise defined, the term "HLA-A02", as used herein, representatively refers to the subtypes such as HLA-A*0201.

Unless otherwise defined, the term "kit" as used herein, is used in reference to a combination of reagents and other materials. It is not intended that the term "kit" be limited to a particular combination of agents and/or materials.

To the extent that the methods and compositions of the present invention find utility in the context of the "treatment" of disease caused by neovascularization in human choroid (neovascular maculopathy), a treatment is deemed "efficacious" if it leads to clinical benefit such as, decrease in the detachment of pigment epithelium, amelioration of the detachment of pigment epithelium, reduced leakage, or amelioration of distortion in the subject. Efficaciousness is determined in association with any known method for treating the disease caused by neovascularization in human choroid (neovascular maculopathy).

Unless otherwise defined, all technical and scientific terms used herein have the same meaning as commonly understood by one of ordinary skill in the art to which the present invention belongs.

The present invention relates to pharmaceutical compositions for treating and/or preventing a disease caused by neovascularization in the choroid (neovascular maculopathy) and pharmaceutical compositions for inhibiting neovascularization in the choroid, which comprise as an active ingredient a peptide comprising an amino acid sequence derived from a VEGFR-1 protein and having an activity of inducing cytotoxic T cells (hereinafter referred to as "VEGFR-1 peptide") (hereinafter, the composition may together be referred to as "pharmaceutical composition of the present invention") and/or a polynucleotide encoding thereof. Furthermore, the present invention relates to vaccines for treating and/or preventing a disease caused by neovascularization in the choroid (neovascular maculopathy), and vaccines for inhibiting neovascularization in the choroid, which comprise VEGFR-1 (hereinafter, the vaccine may together be referred to as "vaccine of the present invention") and/or a polynucleotide encoding thereof. The pharmaceutical composition and vaccine above can comprise any other substances, for example immune stimulators. Preferably, a peptide comprising an amino acid sequence derived from other protein and having an activity of inducing cytotoxic T cells can be comprised. More preferably, a peptide comprising an amino acid sequence derived from a VEGFR-2 protein and having an activity of inducing cytotoxic T cells (hereinafter referred to as "VEGFR-2 peptide"). The present invention is based on the present inventors' finding that pharmaceutical compositions/vaccines comprising VEGFR-1 peptide are effective for inhibiting neovascularization in the choroid.

VEGFR-1 Peptide

The VEGFR-1 peptide contained in the pharmaceutical compositions and vaccines of the present invention (hereinafter, "VEGFR-1 peptide" may be referred to as "peptide of the present invention") can be obtained by synthesizing peptides from any position in the amino acid sequence of a known VEGFR-1 protein. The present invention can contain VEGFR-2 peptide and also can be obtained by synthesizing peptides from any position in the amino acid sequence of a known VEGFR-2. Amino acid sequences of human VEGFR-1 and human VEGFR-2 are known, and those skilled in the art can easily obtain them from protein sequence databases and such available on the Internet. An example of the amino acid sequence of a human VEGFR-1 protein is the amino acid sequence of SEQ ID NO: 19 (the amino acid sequence encoded by the nucleotide sequence of GenBank Accession No. NM_002019). An example of the amino acid sequence of a human VEGFR-2 protein is the amino acid sequence of SEQ ID NO: 21 (the amino acid sequence encoded by the nucleotide sequence of GenBank Accession No. NM_002253).

Peptide synthesis can be performed according to methods conventionally used in peptide chemistry. Conventional synthesis methods are described in documents such as "Peptide Synthesis", Interscience, New York, 1966; "The Proteins", Vol. 2, Academic Press Inc., New York, 1976; "Peptide Synthesis (Peptide Gosei)", Maruzen, 1975; "Fundamentals and Experiments of Peptide Synthesis (Peptide Gosei no Kiso to Jikken)", Maruzen, 1985; and "The sequel of Development of Pharmaceuticals (Zoku Iyakuhin no Kaihatsu)", Vol. 14, Peptide Synthesis (Peptide Gosei), Hirokawa Shoten, 1991, and in publications such as International Publication No. WO 99/67288. Peptides of the present invention may also be synthesized by known genetic engineering methods. The following is an example of a genetic engineering synthesis method. A vector into which a DNA encoding a peptide of the present invention has been inserted is introduced into suitable host cells to produce transformed cells. The peptides of the present invention can be obtained by collecting the peptides produced in these transformed cells. The peptides of the present invention may also be produced initially as a fusion protein, which is then cleaved using an appropriate protease to obtain the peptides.

In a method for preparing a fusion protein, a polynucleotide encoding a peptide of the present invention may be ligated in frame with a polynucleotide encoding another peptide, and this may be inserted into an expression vector for expression in a host. Techniques known to those skilled in the art can be used for this purpose. For peptides fused with the peptides of the present invention, one may use known peptides such as FLAG (Hopp, T. P. et al., BioTechnology (1988) 6, 1204-1210), 6× His consisting of six histidine (His) residues, 10× His, influenza hemagglutinin (HA), human c-myc fragments, VSV-GP fragments, p 18HIV fragments, T7-tag, HSV-tag, E-tag, SV40T antigen fragments, lck tag, alpha-tubulin fragments, B-tag, and Protein C fragments. It is also possible to ligate the peptides of the present invention to glutathione-S-transferase (GST), influenza hemagglutinin (HA), immunoglobulin constant regions, beta-galactosidase, maltose-binding protein (MBP), or such to produce the fusion proteins. The peptides of the present invention can be obtained by treating the fusion proteins produced in this manner with a suitable protease, and then collecting the peptides of interest. The peptides can be collected by methods known to those skilled in the art, such as affinity chromatography.

As an amino acid sequence of a peptide of the present invention, for example, any sequence can be selected from the whole amino acid sequence of a VEGFR-1 protein or the whole amino acid sequence of a VEGFR-2 protein using binding affinity to HLA antigens as an indicator. Binding affinity to HLA antigens can be measured by isolating cells having HLA antigens on the cell surface, such as dendritic cells, and measuring binding of the peptides to the cells using commonly performed methods. Alternatively, binding affinity can be calculated in silico by software recently available on the Internet, such as those described in Parker K. C., J. Immunol. 152, 1994. When applied to the Japanese, for example, A-24 type, A-02 type, or such, which are said to be frequently expressed in the Japanese population, is preferably used as an HLA antigen to obtain effective results. HLA antigens such as the A-02 and A-24 types each include subtypes such as A-0201 or A-2402. Examples of VEGFR-1 peptides having high binding affinity to HLA-A*0201 include peptides comprising the amino acid sequences of SEQ ID NOs: 1 to 3, and examples of VEGFR-1 peptides having high binding affinity to HLA-A*2402 include peptides comprising the amino acid sequence of SEQ ID NO: 4 (WO 2006/093030). Examples of VEGFR-2 peptides having high binding affinity to HLA-A*0201 include peptides comprising the amino acid sequences of SEQ ID NOs: 11 to 17, and examples of VEGFR-2 peptides having high binding affinity to HLA-A*2402 include peptides comprising the amino acid sequences of SEQ ID NOs: 5 to 10 (WO 2004/024766). In clinical practice, peptides having high binding affinity to an HLA antigen carried by a patient requiring treatment can be suitably selected by investigating the type of the HLA antigen in advance.

Peptides having high binding affinity to an HLA antigen are highly likely to be effective as peptides having an activity to induce cytotoxic T cells (CTLs). Still, it is desirable to examine whether or not the candidate peptide selected using the presence of high binding affinity as an indicator actually has an activity to induce CTLs. The CTL-inducing activity can be confirmed by stimulating antigen-presenting cells comprising human MHC antigens (such as B-lymphocytes, macrophages, and dendritic cells), preferably dendritic cells derived from human peripheral blood mononuclear cells, with the candidate peptide; mixing the cells with CD8-positive cells; and then measuring cytotoxicity against the target cells. As the reaction system, transgenic animals produced to express a human HLA antigen (for example, those described in Hum. Immunol. 2000 August; 61(8):764-79 Related Articles, Books, Linkout Induction of CTL response by a minimal epitope vaccine in HLA A*0201/DR1 transgenic mice: dependence on HLA class II restricted T(H) response., Ben Mohamed L., Krishnan R., Longmate J., Auge C., Low L., Primus J., Diamond D J.) may be used. Cytotoxicity can be calculated from the radioactivity released from target cells which are radiolabeled with, for example, 51Cr or such. Alternatively, the activity can be examined by measuring the IFN-gamma produced and released by CTLs in the presence of antigen-presenting cells that carry peptides, and visualizing the inhibition zone on the media using anti-IFN-gamma monoclonal antibodies.

The length of the peptides of the present invention is not particularly limited as long as they have CTL-inducing activity, but is preferably 50 amino acids or less, more preferably 30 amino acids or less, and even more preferably 15 amino acids or less. For example, when presented on antigen-presenting cells in vivo, various proteins are degraded to 9-mer peptides (nonapeptides) and are then presented. Therefore, the peptides of the present invention are desirably 9-mers (nonapeptides) or 10-mers (decapeptides). Preferred VEGFR-1 peptides include peptides comprising the amino acid sequences of SEQ ID NOs: 1 to 4 (WO 2006/093030). Preferred VEGFR-2 peptides include peptides comprising the amino acid sequences of SEQ ID NOs: 5 to 17 (WO 2004/024766).

Furthermore, one, two, or several amino acids can be substituted, deleted, added, and/or inserted to the amino acid sequences of partial peptides of naturally occurring VEGFR-1 or VEGFR-2. Herein, "several" means five or less, and preferably three or less. When modifying amino acid residues, it is desirable to substitute with amino acids in which the properties of the amino acid side chains are maintained. Examples of amino acid side chain properties are: hydrophobic amino acids (A, I, L, M, F, P, W, Y, and V); hydrophilic amino acids (R, D, N, C, E, Q, G, H, K, S, and T); amino acids comprising aliphatic side chains (G, A, V, L, I, and P); amino acids comprising hydroxyl group-containing side chains (S, T, and Y); amino acids comprising sulfur atom-containing side chains (C and M); amino acids comprising carboxylic acid- and amide-containing side chains (D, N, E, and Q); amino acids comprising basic side chains (R, K, and H); and amino acids comprising aromatic group-containing side chains (H, F, Y, and W) (all amino acids are represented by one-letter codes in parentheses). Amino acid substitution within each of these groups is generally called conservative substitution. A peptide comprising a modified amino acid sequence, in which one or more amino acid residues are substituted, deleted, added, and/or inserted to a certain amino acid sequence, is known to retain the biological activity of its original peptide (Mark, D. F. et al., Proc. Natl. Acad. Sci. USA (1984) 81, 5662-6; Zoller, M. J. and Smith, M., Nucleic Acids Res. (1982) 10, 6487-500; Wang, A. et al., Science (1984) 224: 1431-3; Dalbadie-McFarland, G. et al., Proc. Natl. Acad. Sci. USA (1982) 79: 6409-13). Preferred examples of such modified VEGFR-1 peptides include peptides comprising an amino acid sequence with one or more amino acid substitutions, deletions, additions, and/or insertions in the amino acid sequence of any one of SEQ ID NOs: 1 to 4. Preferred examples of modified VEGFR-2 peptides include peptides comprising an amino acid sequence with one or more amino acid substitutions, deletions, additions, and/or insertions in the amino acid sequence of any one of SEQ ID NOs: 5 to 17.

Furthermore, since the regularity of sequences of peptides displayed by binding to HLA antigens is already known (J. Immunol., 152:3913, 1994; Immunogenetics, 41:178, 1995; J. Immunol., 155:4307, 1994), sequences having such regularity can be selected, or modifications based on this regularity can be carried out on the peptides obtained as described above. For example, those with high HLA-24 binding affinity are known to be peptides in which the second amino acid from the peptide N terminus is phenylalanine, tyrosine, methionine, or tryptophan, and the C-terminal amino acid is phenylalanine, leucine, isoleucine, tryptophan, or methionine. Therefore, for peptides to be contained in the pharmaceutical compositions or vaccines for administration to subjects carrying the HLA-24-type HLA antigen, one can select peptides in which the second amino acid from the N terminus is phenylalanine, tyrosine, methionine, or tryptophan, and/or the C-terminal amino acid is phenylalanine, leucine, isoleucine, tryptophan, or methionine. Alternatively, the second amino acid from the N terminus of an obtained peptide can be modified to phenylalanine, tyrosine, methionine, or tryptophan, or the C-terminal amino acid can be modified to phenylalanine, leucine, isoleucine, tryptophan, or methionine. Preferred examples of such VEGFR-1 peptides include peptides in which the second amino acid from the N terminus is modified to phenylalanine, tyrosine, methionine, or tryptophan, and/or the C-terminal amino acid is modified to phenylalanine, leucine, isoleucine, tryptophan, or methionine in the amino acid sequence of SEQ ID NO: 4.

Furthermore, preferred examples of such VEGFR-2 peptides include peptides in which the second amino acid from the N terminus is modified to phenylalanine, tyrosine, methionine, or tryptophan, and/or the C-terminal amino acid is modified to phenylalanine, leucine, isoleucine, tryptophan, or methionine in the amino acid sequence of any one of SEQ ID NOs: 5 to 10. Meanwhile, those with high HLA-02 binding affinity are known to be peptides in which the second amino acid from the peptide N terminus is leucine or methionine, and the C-terminal amino acid is valine or leucine. Therefore, as the peptides to be contained in the pharmaceutical compositions or vaccines for administration to subjects carrying the HLA-02-type HLA antigen, one can select peptides in which the second amino acid from the N terminus is leucine or methionine, and/or the C-terminal amino acid is valine or leucine. Alternatively, the second amino acid from the N terminus of the obtained peptide can be modified to leucine or methionine, and the C-terminal amino acid can be modified to valine or leucine. Preferred examples of such VEGFR-1 peptides include peptides in which the second amino acid from the N terminus is modified to leucine or methionine and/or the C-terminal amino acid is modified to valine or leucine in the amino acid sequence of any one of SEQ ID NOs: 1 to 3. An example of modified VEGFR-2 peptides for the HLA-02 type is a peptide comprising the amino acid sequence of SEQ ID NO: 11-17.

Peptides of the present invention can be obtained as described above, but when a peptide sequence is identical to a portion of the amino acid sequence of an endogenous or exogenous protein with a different function, it may cause side effects such as autoimmune diseases or allergic symptoms against specific substances. Therefore, it is preferable to use available databases to carry out homology searches, and examine whether the sequence of the obtained peptide matches the amino acid sequence of other proteins. If the peptide sequence matches the amino acid sequence of another protein, selection of that peptide sequence should preferably be avoided. If homology search shows that no peptides differing in one or two amino acids exist, the above-mentioned amino acid sequence modifications for increasing the binding affinity to HLA antigens and/or the CTL-inducing activity would not cause those problems.

Polynucleotides

The present invention also provides polynucleotides which encode any of the afore-mentioned peptides of the present invention. These include polynucleotides derived from the natural occurring VEGFR-1 gene (GenBank Accession No. NM_002019 (for example, SEQ ID NO: 18)), or VEGFR-2 gene (GenBank Accession No. NM_002253 (for example, SEQ ID NO: 20)) as well as those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill in the art will recognize that each codon in a nucleic acid (except AUG, which is ordinarily the only codon for methionine, and TGG, which is ordinarily the only codon for tryptophan) may be modified to yield a functionally identical molecule. Accordingly, each silent variation of a nucleic acid that encodes a peptide is implicitly described in each disclosed sequence.

The polynucleotide of the present invention may be composed of DNA, RNA, or derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J 1984, 3: 801-5.

Pharmaceutical Compositions and Vaccines Comprising VEGFR-1 Peptide and/or a Polynucleotide Encoding Thereof The present invention provides pharmaceutical compositions for treating and/or preventing a disease caused by neovascularization in human choroid, comprising at least a VEGFR-1 peptide and/or a polynucleotide encoding thereof as an active ingredient.

Treatment in the present invention refers to reducing symptoms characteristic of diseases caused by neovascularization in the choroid in patients who have actually developed the symptoms. In the present invention, the degree of reduction is not particularly limited, and as long as the symptoms can be reduced, even if the degree is very slight, it is included in the meaning of the treatment of the present invention. In the present invention, prevention means suppressing in advance the progress of symptoms characteristic of diseases caused by neovascularization in the choroid. In the present invention, the degree of suppression of the progress is not limited in any way, and as long as the progress can be suppressed, even if the degree is very slight, it is included in the meaning of prevention of the present invention. The symptoms of a disease caused by neovascularization in the choroid include reduced vision. Assessment of whether or not this symptom has been reduced can be determined by a vision test. Furthermore, one can determine whether or not the progress of symptoms is suppressed by evaluating the activity of choroidal neovessels through examinations using fluorescein fundus photography or optical coherence tomography.

Furthermore, the present invention provides vaccines for treating and/or preventing a disease caused by neovascularization in the choroid, comprising at least a VEGFR-1 peptide and/or a polynucleotide encoding thereof as an active ingredient. In the present invention, a vaccine refers to a composition which, when administered to an organism, can induce immune responses in vivo in that organism. In the present invention, immune responses induced in vivo refer to, in particular, induction of CTLs targeting cells expressing VEGFR-1. Since vascular endothelial cells involved in neovascularization in the choroid express VEGFR-1 on the cell surface, they may become targets of CTLs induced by administration of this vaccine. That is, administration of the vaccine of the present invention causes the peptides of the present invention to be presented at high density on the HLA antigens of the antigen-presenting cells, this induces CTLs which react specifically to the complex formed between the presented peptide and HLA antigen, and the power to attack vascular endothelial cells in the choroid is increased. Alternatively, antigen-presenting cells having peptides of the present invention on their cell surface are obtained by extracting dendritic cells from a patient and stimulating them with the peptides of the present invention. Returning the cells to the patient through administration causes CTL induction in the patient, and the power to attack vascular endothelial cells in the choroid can be increased.

The pharmaceutical compositions and vaccines of the present invention are effective against diseases caused by neovascularization in the choroid. There is no limitation on the target diseases of the pharmaceutical compositions and vaccines of the present invention, as long as they are diseases caused by choroid neovascularization. Preferably, the diseases include neovascular maculopathy that associate with diseases such as exudative age-related macular degeneration, myopic macular degeneration, angioid streaks, central exudative chorioretinopathy, various retinal pigment epitheliopathies, choroidal atrophy, choroideremia, and choroidal osteoma. A particularly preferred example is exudative age-related macular degeneration. The pharmaceutical compositions and vaccines of the present invention selectively attack vascular endothelial cells and thus have a low risk of rapid visual reduction and development of severe complications post-treatment, which are problems in conventional therapeutic methods. Therefore, the pharmaceutical compositions of the present invention can be applied not only to patients with severe symptoms but also to early-stage patients with relatively good vision. Since retinal damage is low in early-stage cases with relatively good vision, the visual prognosis post-treatment for advanced cases is expected to be much more favorable than in conventional treatment. Furthermore, pharmaceutical compositions and vaccines of the present invention have been confirmed to show effects in cases that do not respond to conventional therapeutic methods, and can be applied to such cases.

The present invention is based on the finding that neovascularization in the choroid is inhibited by administration of VEGFR-1 peptides. Therefore, the present invention provides pharmaceutical compositions for inhibiting neovascularization in the choroid, comprising at least one type each of a VEGFR-1 peptide and/or a polynucleotide encoding thereof. Furthermore, pharmaceutical compositions comprising VEGFR-1peptides and/or a polynucleotide encoding thereof can be used as vaccines. Therefore, the present invention also provides vaccines for inhibiting neovascularization in the choroid, comprising at least a VEGFR-1 peptide and/or a polynucleotide encoding thereof. The degree of inhibition is not particularly limited, and as long as neovascularization can be inhibited, even if the degree is slight, it is included in the meaning of inhibition.

The pharmaceutical compositions and vaccines of the present invention are not particularly limited so long as they contain at least a VEGFR-1 peptide and/or a polynucleotide encoding thereof, and for example, they may comprise multiple types of VEGFR-1 peptides and/or any other substances, for example immune stimulators. Preferably, a peptide comprising an amino acid sequence derived from other protein and having an activity of inducing cytotoxic T cells can be comprised. More preferably, a peptide comprising an amino acid sequence derived from a VEGFR-2 protein and having an activity of inducing cytotoxic T cells (hereinafter referred to as "VEGFR-2 peptide"). The pharmaceutical compositions and vaccines of the present invention may contain, in addition to peptides, carriers, excipients, and such commonly used for pharmaceuticals when appropriate. For example, they may be used parenterally in the injectable form of sterile solutions or suspensions prepared with water or other pharmaceutically acceptable liquids. They may be formulated by appropriately combining them with pharmaceutically acceptable carriers or vehicles, more specifically, sterilized water or physiological saline solutions, vegetable oils, emulsifiers, suspending agents, surfactants, stabilizers, flavoring agents, excipients, vehicles, preservatives, binding agents, and such, and mixing them at a unit dosage form required by generally accepted pharmaceutical practice. The amount of active ingredient in these formulations is included to achieve appropriate doses within specified limit.

When the present invention is a vaccine, it may include an adjuvant so that cellular immunity is effectively established, and they may also include other active ingredients for neovascular maculopathy and such. They may also be made into particulate formulations. For adjuvants, those described in the document (Johnson A G., Clin. Microbiol. Rev., 7:277-289, 1994) or such are available. Other formulations may be liposome preparations, granular preparations produced by binding to micrometer-diameter beads, or lipid-bound preparations.

The amount of VEGFR-1 peptide contained in the pharmaceutical compositions and vaccines of the present invention is not particularly limited as long as it is a pharmaceutically effective amount. For example, an effective amount of each peptide may be 0.001 mg to 1000 mg, preferably 0.001 mg to 1000 mg, and more preferably 0.1 mg to 10 mg. Furthermore, if the pharmaceutical compositions and vaccines contain VEGFR-2 peptide, the combining ratio of the VEGFR-1 peptide to the VEGFR-2 peptide is not particularly limited, as long as pharmaceutically effective amounts of both peptides are contained. The amounts of VEGFR-1 peptide and VEGFR-2 peptide combined may be the same, or the amount of either one of the peptides combined may be greater than the other peptide. While VEGFR-2 is expressed on the surface of almost all vascular endothelial cells, VEGFR-1 is expressed only on the surface of a specific portion of vascular endothelial cells; therefore, the amount of the VEGFR-2 peptide combined can be greater than that of the VEGFR-1 peptide.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid.

The present invention also includes the use of VEGFR-1 peptide and/or a polynucleotide encoding thereof in manufacturing pharmaceutical compositions or vaccines for treating and/or preventing diseases caused by neovascularization in human choroid. Furthermore, the present invention includes the use of VEGFR-1 peptide and/or a polynucleotide encoding thereof in manufacturing pharmaceutical compositions or vaccines for inhibiting neovascularization in human choroid.

The present invention includes VEGFR-1 peptides and/or a polynucleotide encoding thereof to be administered to subjects for treating and/or preventing diseases caused by neovascularization in human choroid. In addition, the present invention includes VEGFR-2 peptides and/or a polynucleotide encoding thereof to be administered to subjects together with a VEGFR-1 peptide and/or a polynucleotide encoding thereof for treating and/or preventing diseases caused by neovascularization in human choroid. Furthermore, the present invention includes VEGFR-2 peptides to and/or a polynucleotide encoding thereof be administered to subjects together with a VEGFR-1 peptide and/or a polynucleotide encoding thereof for inhibiting neovascularization in human choroid. Additionally, the present invention includes VEGFR-1 peptides and/or a polynucleotide encoding thereof to be administered to subjects together with a VEGFR-2 peptide and/or a polynucleotide encoding thereof for inhibiting neovascularization in human choroid.

Kits for Treating or Preventing Neovascular Maculopathy and Kits for Inhibiting Neovascularization in the Choroid The present invention provides kits for treating and/or preventing diseases caused by neovascularization in the choroid, comprising at least a VEGFR-1 peptide and/or a polynucleotide encoding thereof. The present invention also provides kits for inhibiting neovascularization in the choroid, comprising at least a VEGFR-1 peptide and/or a polynucleotide encoding thereof.

The VEGFR-1 peptide to be included in the kits of the present invention may be present individually alone, or they may exist in the form of formulations or vaccines by appropriately combining with pharmaceutically acceptable carriers or vehicles, or more specifically, sterilized water or physiological saline solutions, vegetable oils, emulsifiers, suspending agents, surfactants, stabilizers, flavoring agents, excipients, vehicles, preservatives, binding agents, and such. When they are produced into vaccines, an adjuvant may be included so that cellular immunity is effectively established, and other active ingredients for neovascular maculopathy and such may also be included. Preferably, VEGFR-2 peptide can be included. They may also be made into granular formulations. For adjuvants, those described in the document (Johnson A G., Clin. Microbiol. Rev., 7:277-289, 1994) or such are available. Other formulations may be liposome preparations, granular preparations produced by binding to micrometer-diameter beads, or lipid-bound preparations.

The kits of the present invention may further include pharmaceutically acceptable carriers or vehicles such as those described above so that one who prepares the pharmaceuticals can make appropriate adjustments.

Methods for Treating or Preventing Neovascular Maculopathy, and Methods for Inhibiting Neovascularization in the Choroid The present invention further provides methods for treating and/or preventing diseases caused by neovascularization in the choroid, comprising the step of administering to a subject at least a VEGFR-1 peptide and/or a polynucleotide encoding thereof. Furthermore, the present invention provides methods for inhibiting neovascularization in the choroid, comprising the step of administering to a subject at least a VEGFR-1 peptide and/or a polynucleotide encoding thereof.

VEGFR-1 peptide can be administered to subjects parenterally in the injectable form of sterile solutions or suspensions prepared with water or other pharmaceutically acceptable liquids. They may also be administered to subjects in the form of a formulation by appropriately combining with pharmaceutically acceptable carriers or vehicles, more specifically, sterilized water or physiological saline solutions, vegetable oils, emulsifiers, suspending agents, surfactants, stabilizers, flavoring agents, excipients, vehicles, preservatives, binding agents, and such, and mixing them at a unit dosage form required for generally accepted pharmaceutical practice. When administering VEGFR-1 peptide as vaccines, they may be administered together with an adjuvant so that cellular immunity is effectively established, and they may also be administered together with other active ingredients for neovascular maculopathy and such. For adjuvants, those described in the document (Johnson A G., Clin. Microbiol. Rev., 7:277-289, 1994) or such are available. VEGFR-2 peptide may also be administered together.

Those skilled in the art can suitably plan the method of administration, dose, and period of administration of VEGFR-1 according to the symptoms of patients (subjects) needing administration of the peptides of the present invention. The VEGFR-1 peptide can be administered to subjects as pharmaceutical compositions or vaccines of the present invention, or they may be administered to subjects as pharmaceutical compositions or vaccines containing each of the peptides individually. The VEGFR-1 peptide can be administered by either systemic administration or local administration. Examples of systemic administration include oral administration, intradermal administration, subcutaneous administration, and intravenous injection. Examples of local administration include administration to the vicinity of the choroid.

The dose of VEGFR-1 peptide may be, for example, 0.001 mg to 1000 mg, preferably 0.001 mg to 1000 mg, and more preferably 0.1 mg to 10 mg, but is not limited thereto. Furthermore, without limitation, the vaccines are preferably administered once in a few days or a few months, and more preferably once a week.

EXAMPLES

Hereinbelow, the present invention will be specifically described with reference to the Examples, but it is not to be construed as being limited thereto.

Example 1

Subjects
HLA-A0201-Case 1
As a subject, a 67-year old male patient with age-related macular degeneration who has been treated by photodynamic therapy and Avastin administration was selected. It is a case that did not go to remission by conventional therapeutic methods. Examination of the HLA-A locus confirmed that the subject carries HLA-A*0201.

HLA-A0201-Case 3
As a subject, a 76-year old male patient with age-related macular degeneration who has been treated by injection of a steroid (triamcinolone) below Tenon's capsule, photodynamic therapy, and Avastin administration was selected. It is a case that did not go to remission by conventional therapeutic methods. Examination of the HLA-A locus confirmed that the subject carries HLA-A*0201.

HLA-A2402-Case 1
As a subject, a 67-year old male patient with a age-related macular degeneration patient was selected. It is a case that did not go to remission by conventional therapeutic methods. Examination of the HLA-A locus confirmed that the subject carries HLA-A*2402.

Peptides
HLA-A*2402 restricted VEGFR1 peptide (VEGFR1-A24-1084; SYGVLLWEI; SEQ ID NO:4), HLA-A*2402 restricted VEGFR2 peptide (VEGFR2-A24-169; RFVPDGNRI; SEQ ID NO:8), HLA-A*0201 restricted VEGFR1 peptide (VEGFR1-A2-770; TLFWLLLTL; SEQ ID NO: 2) and HLA-A*0201 restricted VEGFR2 peptide (VEGFR2-A2-773; VIAMFFWLL; SEQ ID NO: 12) of Good Manufacturing Practice (GMP) grade, HLA-A*2402-restricted HIV-Env protein-derived peptide (HIV-A24; RYLRDQQLL; SEQ ID NO: 22) and HLA-A*0201-restricted HIV-Env protein-derived peptide (HIV-A2; SLYNTYATL; SEQ ID NO: 23) were synthesized and analyzed the quality by the American Peptide Company Inc. (Sunnyvale, Calif.).

Method of Administration
The GMP grade synthetic peptides, VEGFR-1 peptide (TLFWLLLTL; SEQ ID NO: 2) and VEGFR-2 peptide (VIAMFFWLL; SEQ ID NO: 12), were obtained from the Human Genome Center, Institute of Medical Sciences, the University of Tokyo. One milligram each of the VEGFR-1 peptide and the VEGFR-2 peptide was mixed with 1 mL of incomplete Freund's adjuvant (MONTANIDE*ISA51VG, SEPPIC, France), and they were administered subcutaneously to the armpit of the patient. The administration was carried out once a week.

PBMCs
Peripheral blood mononuclear cells (PBMCs) were isolated from patients (HLA-A*2402 or HLA-A*0201 positive) by Ficoll-Plaque (Pharmacia) solution.

IFN-Gamma ELISPOT Assay
Before the treatment and at the every end of treatment course, PBMCs were obtained and immediately frozen. For immune monitoring, all frozen PBMCs derived from each patient were thawed at the same time, and stimulated with 10 micro g/ml of the cognate peptide and 20 IU/mL of interleukine-2 (Chiron, Emeryville, Calif.) at 37 degrees C. with 5% $CO_2$ condition for two weeks. After the depletion of $CD4^+$ cells by Dynal CD4 positive isolation kit (Invitrogen, Carlsbad, Calif.), cells were applied for interferon-gamma (IFN-gamma) enzyme-linked immunospot (ELISPOT) assay. IFN-gamma ELISPOT assay was performed according to manufacture's procedure (BD Biosciences, San Jose, Calif.). Briefly, HLA-A*2402-positive B-lymphoblast TISI cells (IHWG Cell and Gene Bank, Seattle, Wash.) or HLA-A*0201-positive B-lymphoblast T2 cells (ATCC, Tokyo, Japan) were incubated with 20 micro g/ml of the cognate peptide or HIV-Env peptide over night. After washing out the remaining peptide that not bind to HLA on the cells, respective peptide-pulsed cells ($2 \times 10^4$ cells/well) were used to stimulate prepared $CD4^-$ cells ($1 \times 10^4$ cells/well) on 96-well plate (Millipore, Bedford, Mass.) at 37 degrees C. with 5% $CO_2$ condition over night. The plates were scanned and analyzed on an ImmunoSpot S4 Analyzer and ImmunoSpot image analyzer software version 5.0 (Cellular Technology Ltd., Cleveland, Ohio). The number of the cognate peptide specific spots was calculated by subtracting the number of spots when stimulated with HIV-Env peptide from the number of spots when stimulated with the cognate peptide. All ELISPOT assays were performed triplicate wells. When the excess spots were detected, it is unable to calculate the accurate spot counts because of the clustering and those wells were defined to be saturated.

Flow Cytometric Analysis

To detect peptide specific T cell receptor, $5×10^5$ of CD4⁻ cells prepared for ELISPOT assay were stained with phycoerythrin (PE)-conjugated HLA-A*2402/VEGFR1 dextramer or HLA-A*0201/VEGFR1 dextramer (DAKO Japan, Tokyo, Japan), fluoroscein isothiocyanate (FITC)-conjugated anti-human CD8 mAb (RPA-T8, BD Biosciences, San Jose, Calif.) and allophycocyanina (APC)-conjugated anti-human CD3 mAb (UCHT1, BD Biosciences, San Jose, Calif.), then analyzed using FACSCanto II (BD Biosciences, San Jose, Calif.). HLA-A*2402/HIV-Env dextramer or HLA-A*0201/HIV-Env dextramer (DAKO Japan, Tokyo, Japan) were used as negative controls. Dead cells were excluded from the analysis based on the staining with 7-ADD (Sigma-Aldrich Japan, Tokyo, Japan).

Results

HLA-A0201-Case1

The progression stage of age-related macular degeneration was analyzed using optical coherence tomography, fluorescein fundus imaging, and fundus photography. Before starting administration of the VEGFR-1 peptide and the VEGFR-2 peptide, a large detachment of pigment epithelium was observed in the tomographic images of optical coherence tomography (FIG. 1A). Detachment of pigment epithelium was clearly observed also in the fundus photograph (FIG. 1B). Furthermore, a large amount of leakage was observed in the image of fluoroscein fundus photography (FIG. 1D).

Five months after starting administration of the VEGFR-1 peptide and the VEGFR-2 peptide, a significant decrease in the detachment of pigment epithelium was observed in the tomographic images of optical coherence tomography (FIG. 1D). Amelioration of the detachment of pigment epithelium was also observed with fundus photography (FIG. 1E). Furthermore, reduced leakage was confirmed in the fluoroscein fundus photograph (FIG. 1F). It was also reported that subjective symptoms such as distortion were greatly ameliorated. The vision of the right eye was slightly improved (Rv=(0.9)→Rv=(1.2)). These results confirmed that administration of the VEGFR-1 peptide and the VEGFR-2 peptide yields amelioration effects for age-related macular degeneration. Problems suggestive of safety issue did not arise.

HLA-A0201-Case3

Figure 2:
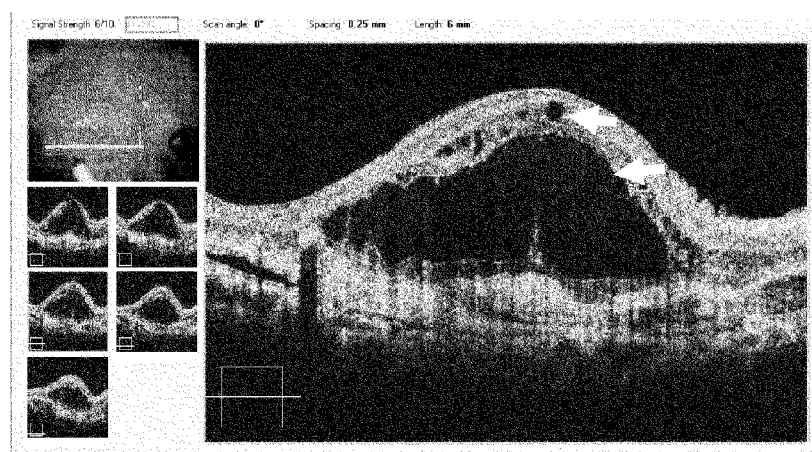
FIG. 2A-2B show retinal tomographic images acquired by optical coherence tomography performed on a single case of an age-related macular degeneration patient HLA-A0201-Case3 who has been given a VEGFR-1-derived peptide and a VEGFR-2-derived peptide. (A) shows the tomographic images before starting the administration and (B) shows the tomographic images one month after starting the administration. The arrows indicate edema, and the dashed arrow indicates an apparently a fibrosed and hypoactive neovascular membrane.
Figure 2:
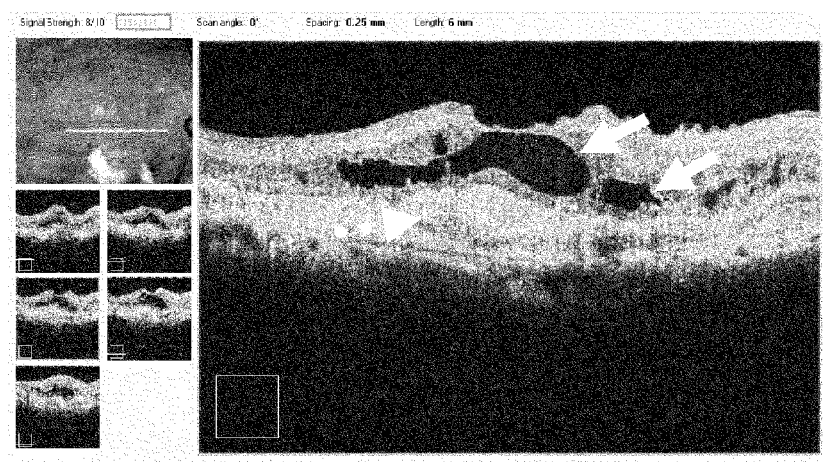

Before starting administration of the VEGFR-1 peptide and the VEGFR-2 peptide, rupture of the retina due to leakage from the neovessels and edema in the retina were observed in the tomographic images of optical coherence tomography (FIG. 2A). One month after starting administration of the VEGFR-1 peptide and the VEGFR-2 peptide, edema of the retina was clearly found to be reduced compared to before the administration was started (FIG. 2B). Furthermore, an apparently fibrosed and hypoactive neovascular membrane was observed (FIG. 2B). Furthermore, it was reported that subjective symptoms such as distortion were significantly ameliorated. These results confirmed that administration of the VEGFR-1 peptide and the VEGFR-2 peptide yields amelioration effects for the symptoms of age-related macular degeneration in this case as well. Problems suggestive of safety issue did not arise.

HLA-A2402-Case1

Figure 3:
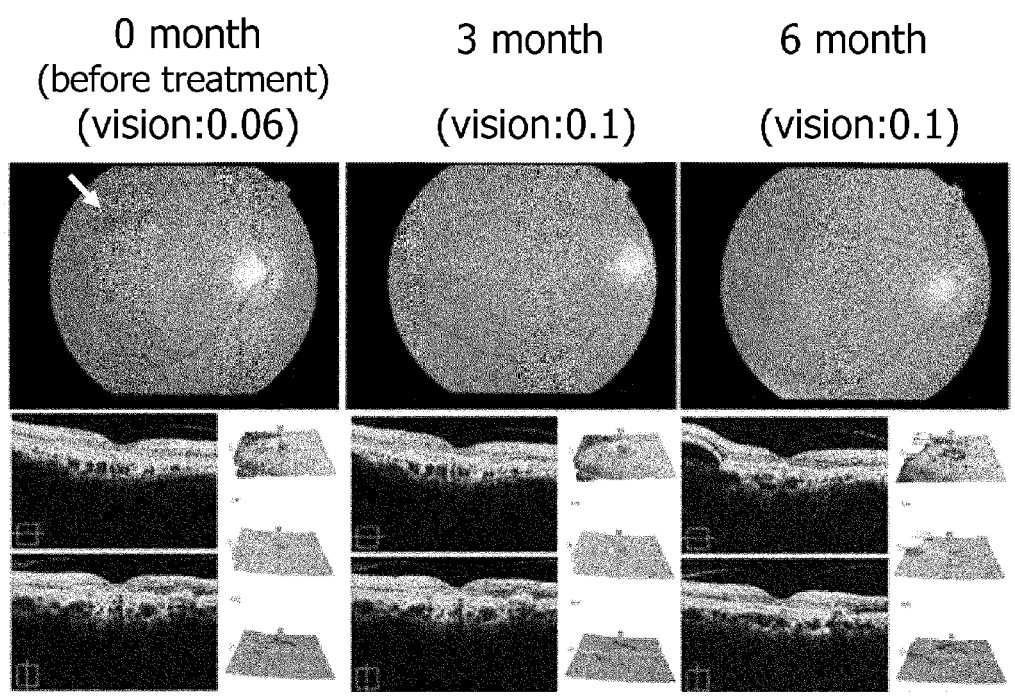
FIG. 3 shows the symptomatic relief and the recovery of vision of an age-related macular degeneration patient HLA-A2402-Case 1 who has been given a VEGFR-1-derived peptide and a VEGFR-2-derived peptide. Upper photographs show ocular fundus photographs and lower photographs show retinal tomographic images subretinal hemorrhages (arrowhead) disappeared and the vision was improved (parenthetic value) after starting the treatment. Additionally, the anatomy of macular was remaining the same.

Before starting administration of the VEGFR-1 peptide and the VEGFR-2 peptide, clear subretinal hemorrhages were observed in the ocular fundus photographs (FIG. 3, upper left panel). Three month after starting administration, the subretinal hemorrhages were obviously relieved compared with before administration (FIG. 3 upper center and right panels). Furthermore, anatomy of macular region have no effect (FIG. 3, lower panel) and the vision was improved.

Monitoring Analysis

IFN-gamma ELISPOT assay and/or Flow cytometric analysis were performed as monitoring of patient treated.

TABLE 1

Summary of monitoring analysis

| Dose | Case | Treatment course | CTL response R1 | R2 | CMV | Multimer analysis CD8⁺ R1dextramer⁺/ CD3⁺ CD4⁻ (%) |
|---|---|---|---|---|---|---|
| 1 mg | HLA-A0201-Case 1 | pre-treatment | +++ | − | +++ | NT |
| | | post-1course | +++ | − | +++ | NT |
| | | post-2course | +++ | − | +++ | NT |
| | | post-3course | +++ | − | +++ | NT |
| | | post-4course | +++ | − | +++ | NT |
| | HLA-A0201-Case 3 | pre-treatment | + | + | +++ | 0.01 |
| | | post-1course | +++ | − | +++ | 0.05 |
| | | post-2course | NT | NT | NT | NT |
| | | post-3course | +++ | − | +++ | 0.69 |
| | | post-4course | +++ | − | +++ | 0.04 |
| | | post-5course | +++ | − | +++ | 0.11 |
| | HLA-A2402-Case 1 | pre-treatment | − | − | +++ | NT |
| | | post-1course | − | − | + | NT |
| | | post-2course | +++ | − | − | NT |
| | | post-3course | ++ | + | ++ | NT |
| | | post-4course | + | − | − | NT |
| | | post-5course | +++ | ++ | +++ | NT |
| | | post-6course | ++ | − | − | NT |

NT: not tested

HLA-A0201-Case1

Figure 4:
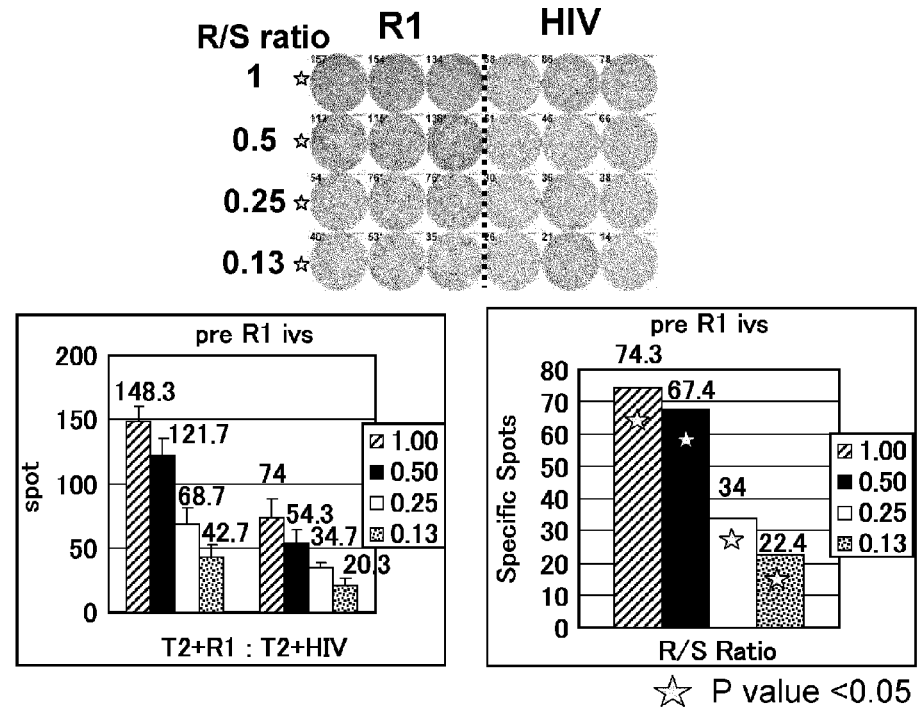
FIG. 4a-4b show the VEGFR1 peptide-specific response of HLA-A0201-Case1. The PBMCs of pre-treatment (a), and post-1 course (b) were tested. In each figure, the photograph of ELISPOT plate in which the PBMCs were stimulated by VEGFR1-A2-770 peptide (upper left panel) or HIV-Env peptide (upper right panel) is shown. R/S; responder/stimulator ratio. The number of spot counts (lower left panel) and VEGFR1 peptide-specific spots (lower right panel) is indicated in the graphs. Statistical analysis was performed using unpaired Student's t-test (Star mark; P<0.05). Circular mark indicates that spot counts are saturated.
FIG. 4c-4d show the VEGFR1 peptide-specific response of HLA-A0201-Case1. The PBMCs of post-2 courses (c), and post-3 courses (d) were tested. In each figure, the photograph of ELISPOT plate in which the PBMCs were stimulated by VEGFR1-A2-770 peptide (upper left panel) or HIV-Env peptide (upper right panel) is shown. R/S; responder/stimulator ratio. The number of spot counts (lower left panel) and VEGFR1 peptide-specific spots (lower right panel) is indicated in the graphs. Statistical analysis was performed using unpaired Student's t-test (Star mark; P<0.05). Circular mark indicates that spot counts are saturated.
FIG. 4e shows the VEGFR1 peptide-specific response of HLA-A0201-Case1. The PBMCs of post-4 courses (e) was tested. In each figure, the photograph of ELISPOT plate in which the PBMCs were stimulated by VEGFR1-A2-770 peptide (upper left panel) or HIV-Env peptide (upper right panel) is shown. RIS; responder/stimulator ratio. The number of spot counts (lower left panel) and VEGFR1 peptide-specific spots (lower right panel) is indicated in the graphs. Statistical analysis was performed using unpaired Student's t-test (Star mark; P<0.05). Circular mark indicates that spot counts are saturated.
Figure 1:
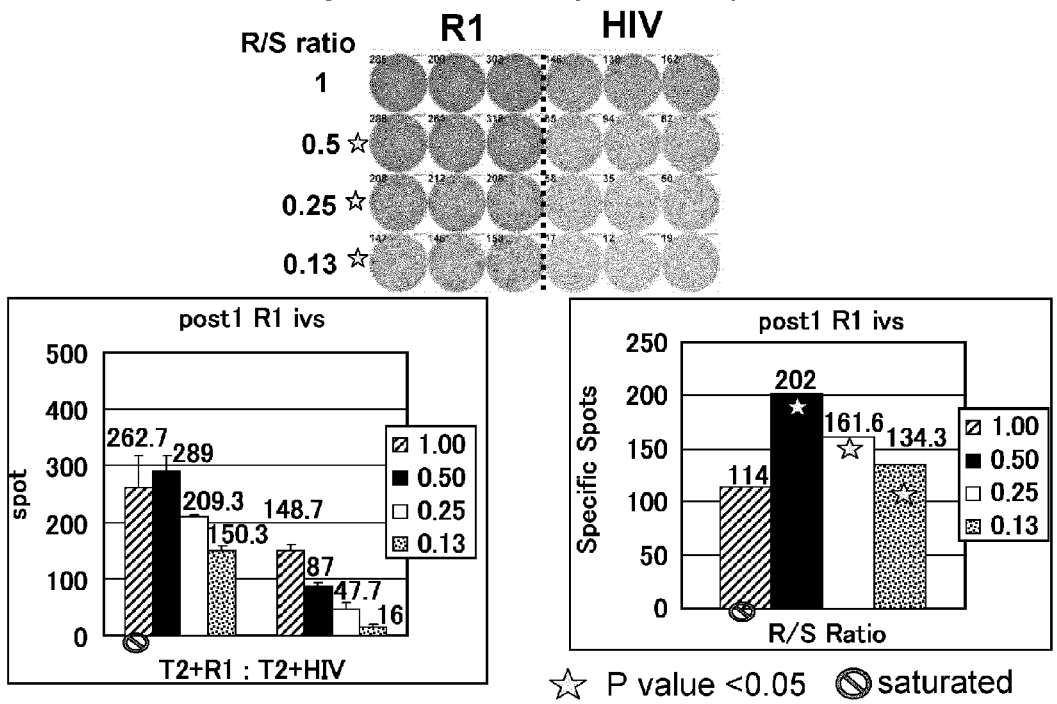
Figure 4:
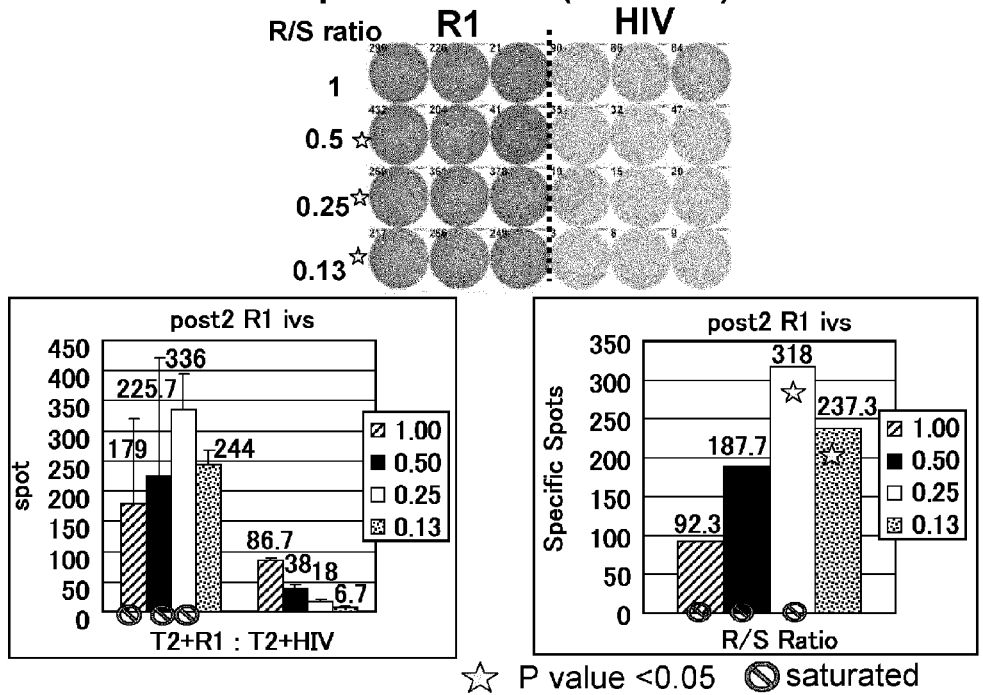
Figure 2:
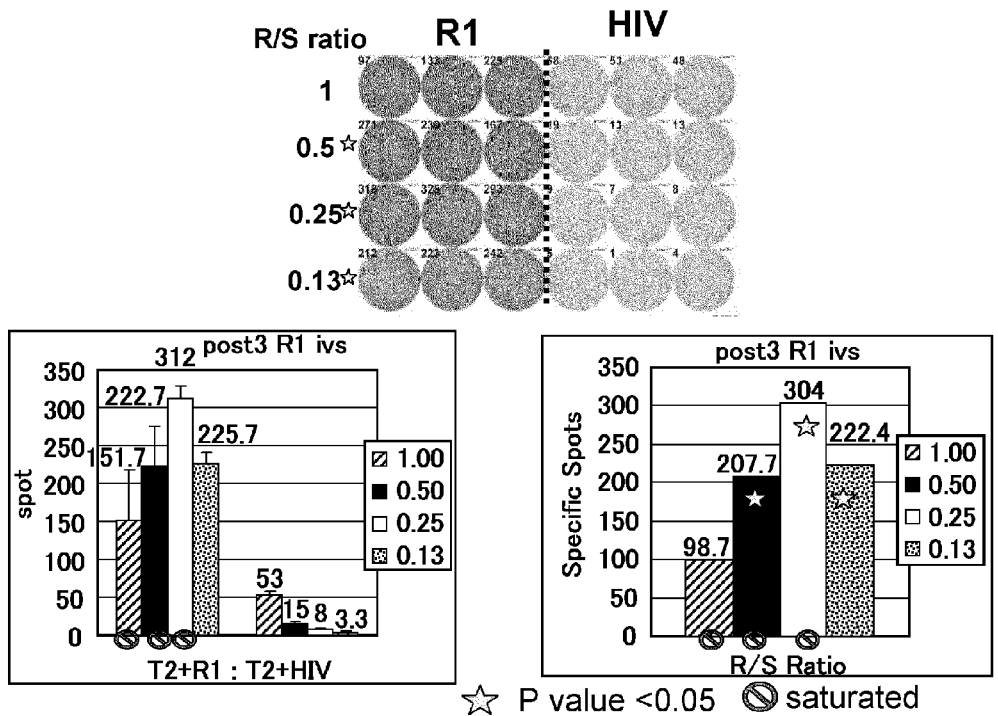
Figures 3, 4:
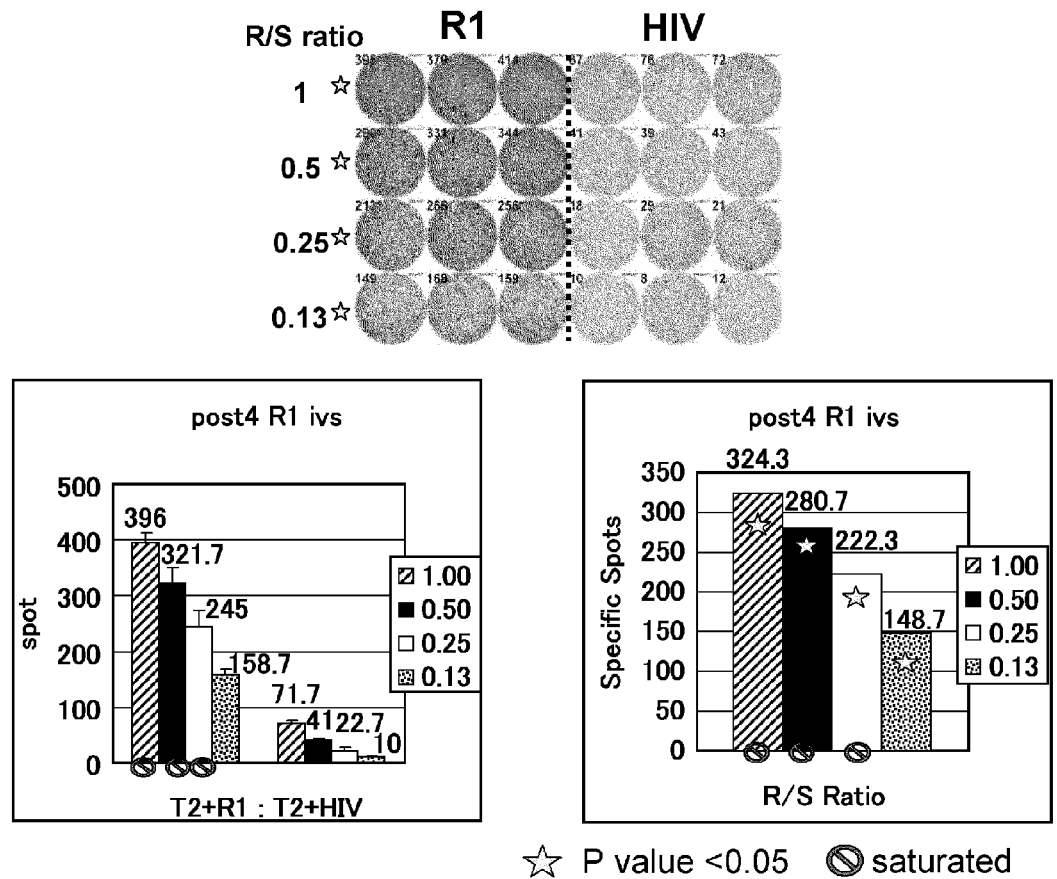
Figure 5:
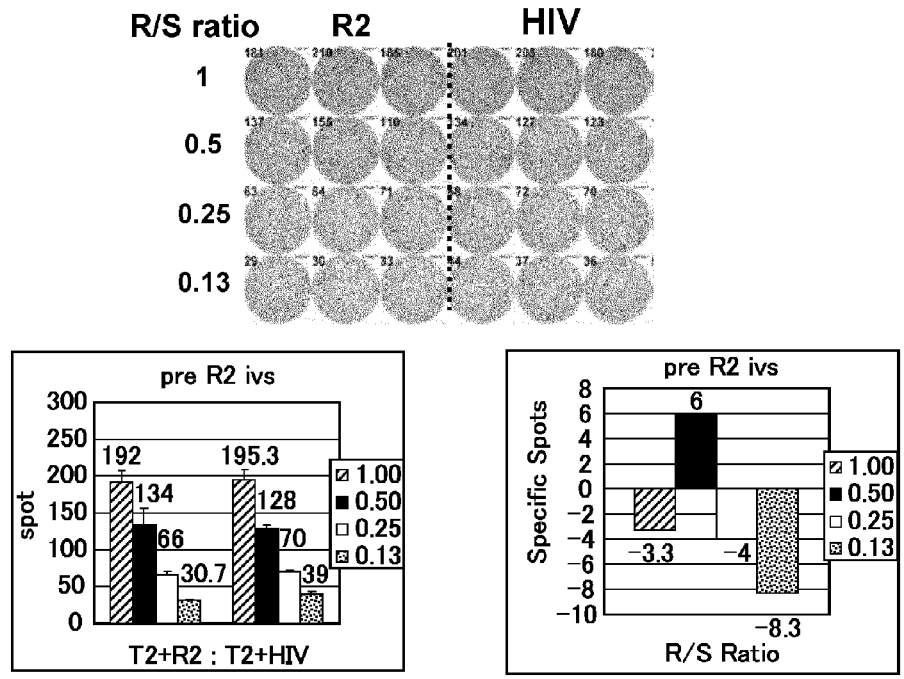
FIG. 5a-5b show the VEGFR2 peptide-specific response of HLA-A0201-Case1. The PBMCs of pre-treatment (a), and post-1 course (b) were tested. In each figure, the photograph of ELISPOT plate in which the PBMCs were stimulated by VEGFR2-A2-773 peptide (upper left panel) or HIV-Env peptide (upper right panel) is shown. R/S; responder/stimulator ratio. The number of spot counts (lower left panel) and VEGFR2 peptide-specific spots (lower right panel) is indicated in the graphs.
FIG. 5c-5d show the VEGFR2 peptide-specific response of HLA-A0201-Case1. The PBMCs of post-2 courses (c), and post-3 courses (d) were tested. In each figure, the photograph of ELISPOT plate in which the PBMCs were stimulated by VEGFR2-A2-773 peptide (upper left panel) or HIV-Env peptide (upper right panel) is shown. R/S; responder/stimulator ratio. The number of spot counts (lower left panel) and VEGFR2 peptide-specific spots (lower right panel) is indicated in the graphs.
FIG. 5e shows the VEGFR2 peptide-specific response of HLA-A0201-Case1. The PBMCs of post-4 courses (e) was tested. In each figure, the photograph of ELISPOT plate in which the PBMCs were stimulated by VEGFR2-A2-773 peptide (upper left panel) or HIV-Env peptide (upper right panel) is shown. RIS; responder/stimulator ratio. The number of spot counts (lower left panel) and VEGFR2 peptide-specific spots (lower right panel) is indicated in the graphs.
Figure 1:
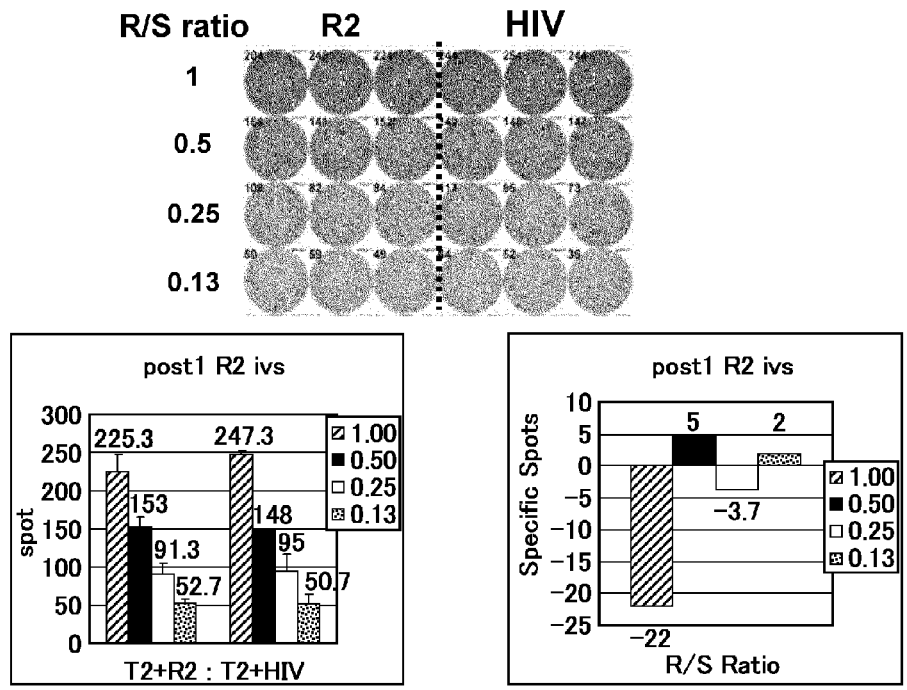
Figure 5:
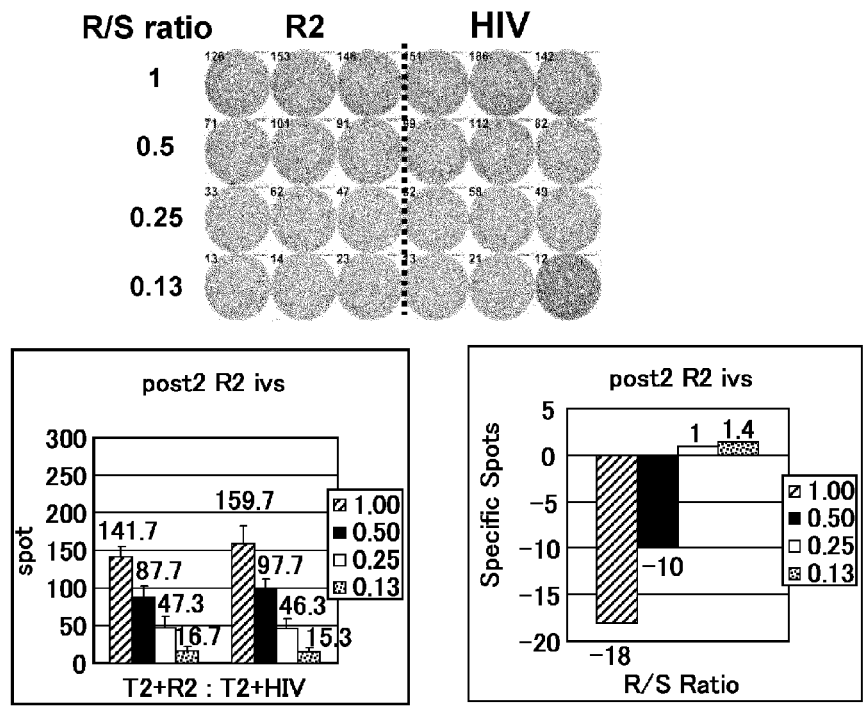
Figure 2:
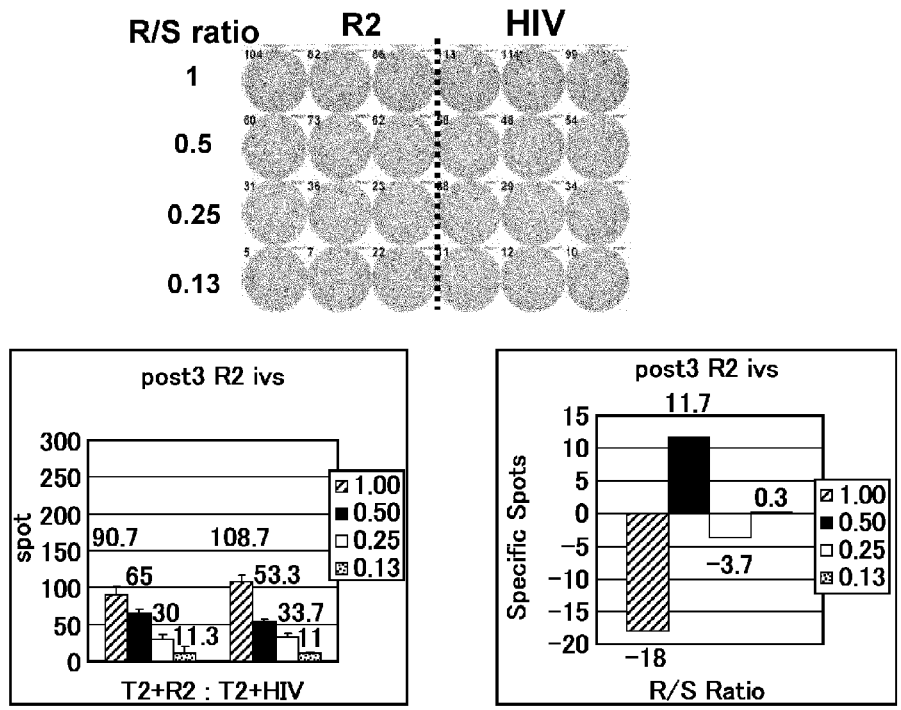
Figures 3, 5:
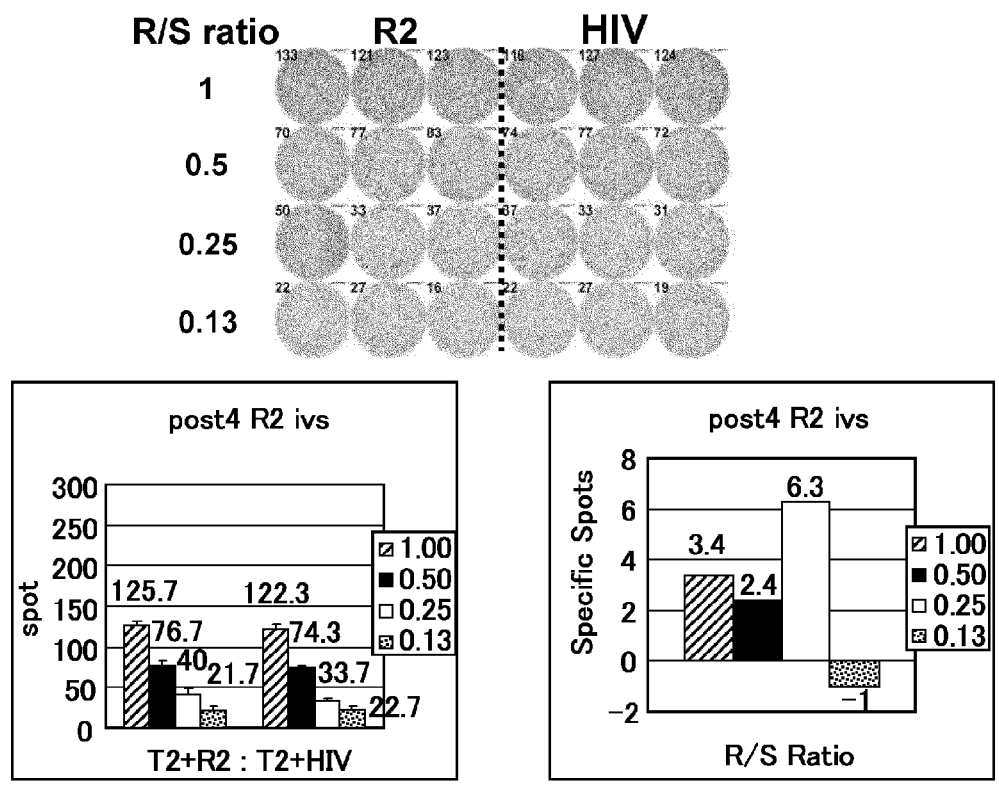

Significantly higher number of spots were observed when stimulated with VEGFR1-A2-770 peptide-pulsed T2 cells compared with that stimulated with HIV-Env peptide-pulsed T2 cells in IFN-gamma ELISPOT assay, especially after treatment courses (Table 1 and FIG. 4). On the other hand, no specific IFN-gamma production was observed by stimulation with VEGFR2-A2-773 peptide (Table 1 and FIG. 5), despite administration of both VEGFR1-A2-770 peptide and VEGFR2-A2-773 peptide shown obvious efficacy in the patient. As a result, it indicated that VEGFR1-A2-770 peptide function to improve the case alone.

HLA-A0201-Case3

Figures 1, 6:
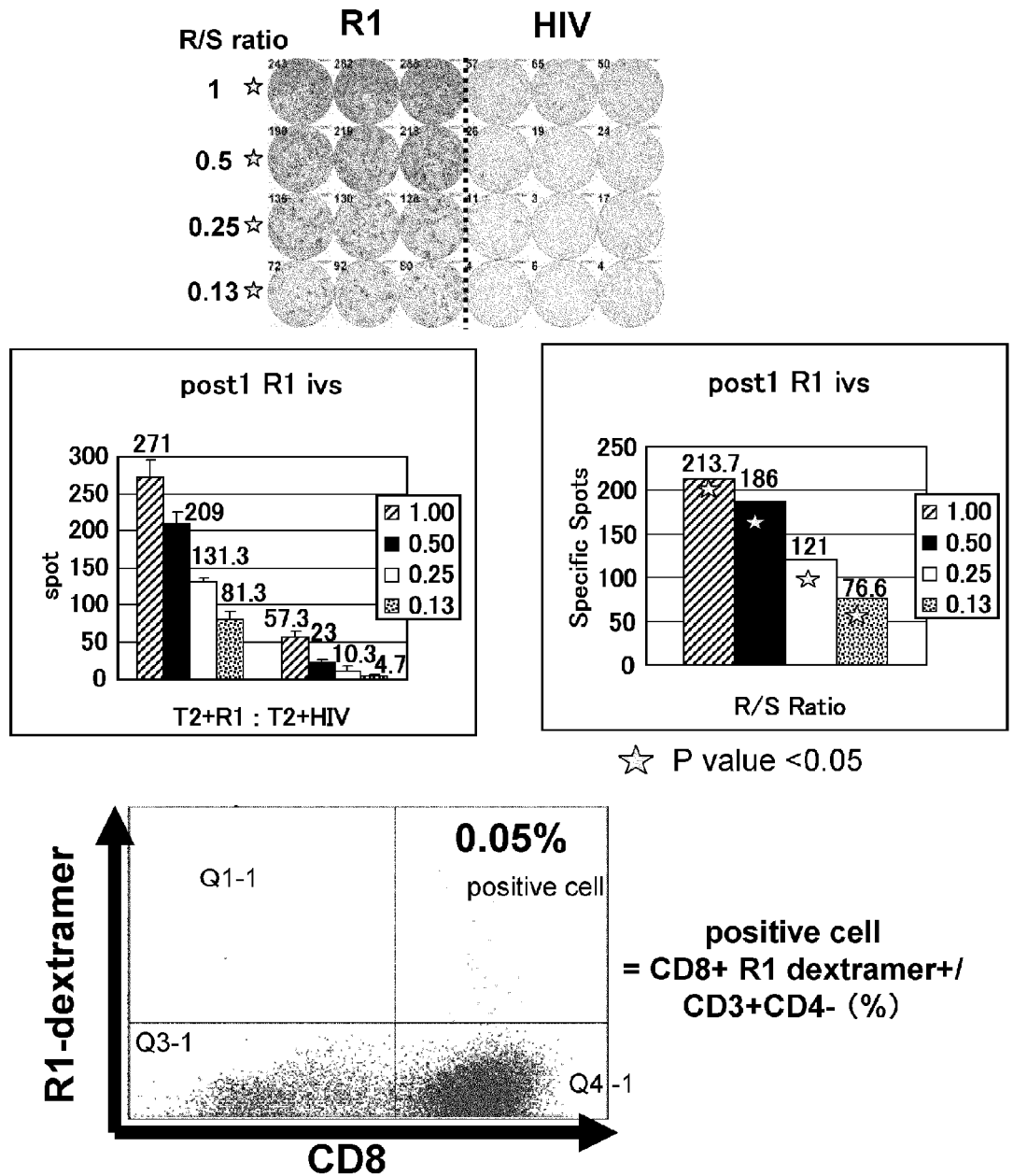
FIG. 6a shows the VEGFR1 peptide-specific response of HLA-A0201-Case3. The responses of the PBMCs of post-1 course (a) is shown as representative results. In each figure, the photograph of ELISPOT plate in which the PBMCs were stimulated by VEGFR1-A2-770 peptide (upper left panel) or HIV-Env peptide (upper right panel) is shown. R/S; responder/stimulator ratio. The number of spot counts (middle left panel) and VEGFR1 peptide-specific spots (middle right panel) is indicated in the graphs. Statistical analysis was performed using unpaired Student's t-test (Star mark; P<0.05). The VEGFR1 peptide-specific T cell receptor was detected by HLA-A*0201/VEGFR1 dextramer (lower panel).
FIG. 6b shows the VEGFR1 peptide-specific response of HLA-A0201-Case3. The responses of the PBMCs of post-3 courses (b) is shown as representative results. In each figure, the photograph of ELISPOT plate in which the PBMCs were stimulated by VEGFR1-A2-770 peptide (upper left panel) or HIV-Env peptide (upper right panel) is shown. RIS; responder/stimulator ratio. The number of spot counts (middle left panel) and VEGFR1 peptide-specific spots (middle right panel) is indicated in the graphs. Statistical analysis was performed using unpaired Student's t-test (Star mark; P<0.05). The VEGFR1 peptide-specific T cell receptor was detected by HLA-A*0201/VEGFR1 dextramer (lower panel).
FIG. 6c shows the VEGFR1 peptide-specific response of HLA-A0201-Case3. The responses of the PBMCs of post-4 courses (c) is shown as representative results. In each figure, the photograph of ELISPOT plate in which the PBMCs were stimulated by VEGFR1-A2-770 peptide (upper left panel) or HIV-Env peptide (upper right panel) is shown. R/S; responder/stimulator ratio. The number of spot counts (middle left panel) and VEGFR1 peptide-specific spots (middle right panel) is indicated in the graphs. Statistical analysis was performed using unpaired Student's t-test (Star mark; P<0.05). The VEGFR1 peptide-specific T cell receptor was detected by HLA-A*0201/VEGFR1 dextramer (lower panel).
FIG. 6d shows the VEGFR1 peptide-specific response of HLA-A0201-Case3. The responses of the PBMCs of post-5 courses (d) is shown as representative results. In each figure, the photograph of ELISPOT plate in which the PBMCs were stimulated by VEGFR1-A2-770 peptide (upper left panel) or HIV-Env peptide (upper right panel) is shown. R/S; responder/stimulator ratio. The number of spot counts (middle left panel) and VEGFR1 peptide-specific spots (middle right panel) is indicated in the graphs. Statistical analysis was performed using unpaired Student's t-test (Star mark; P<0.05). The VEGFR1 peptide-specific T cell receptor was detected by HLA-A*0201/VEGFR1 dextramer (lower panel).
Figure 6:
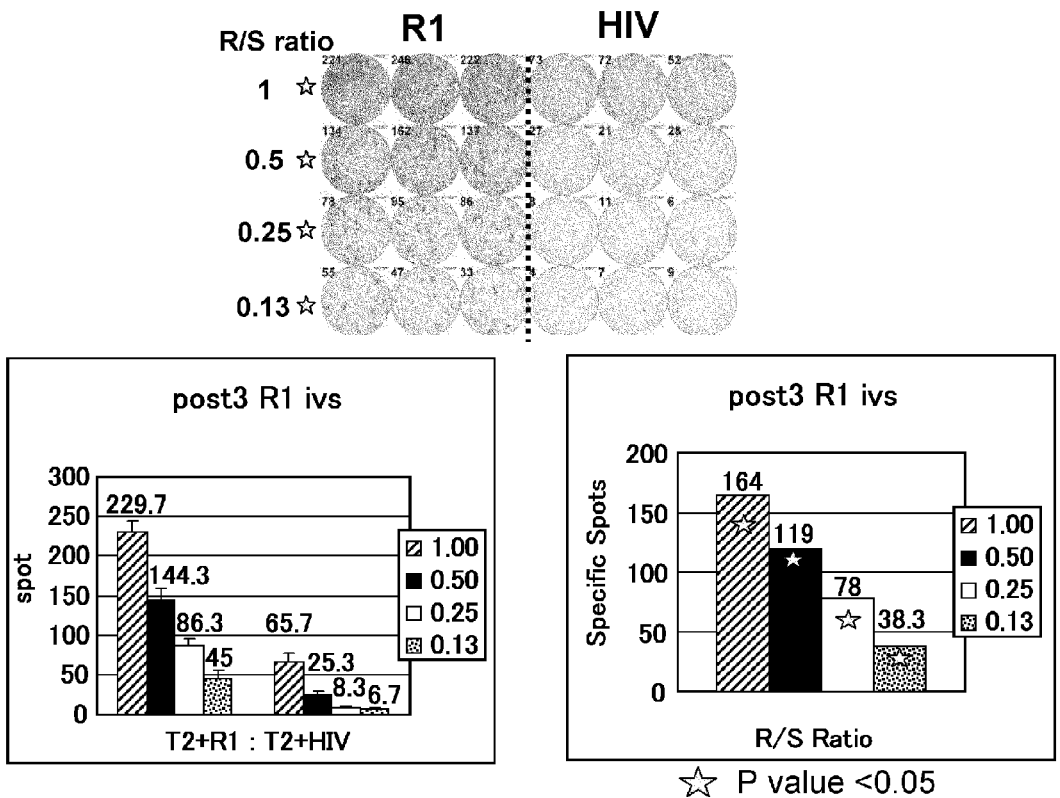
Figure 2:
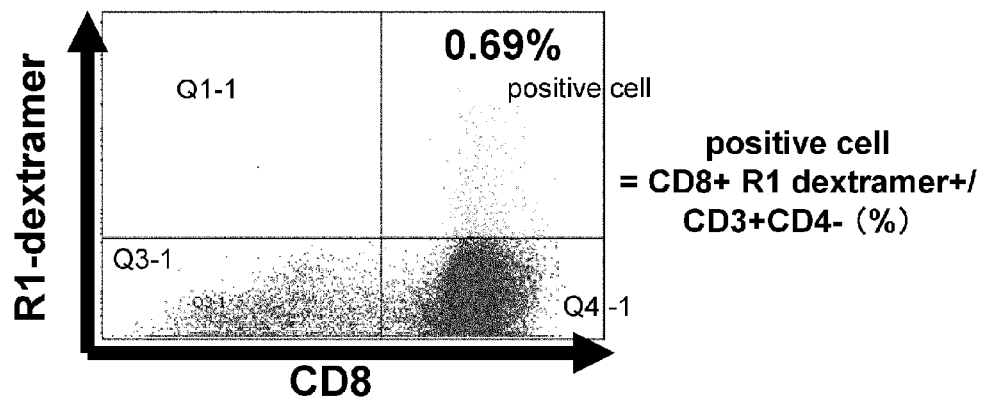
Figures 4, 6:
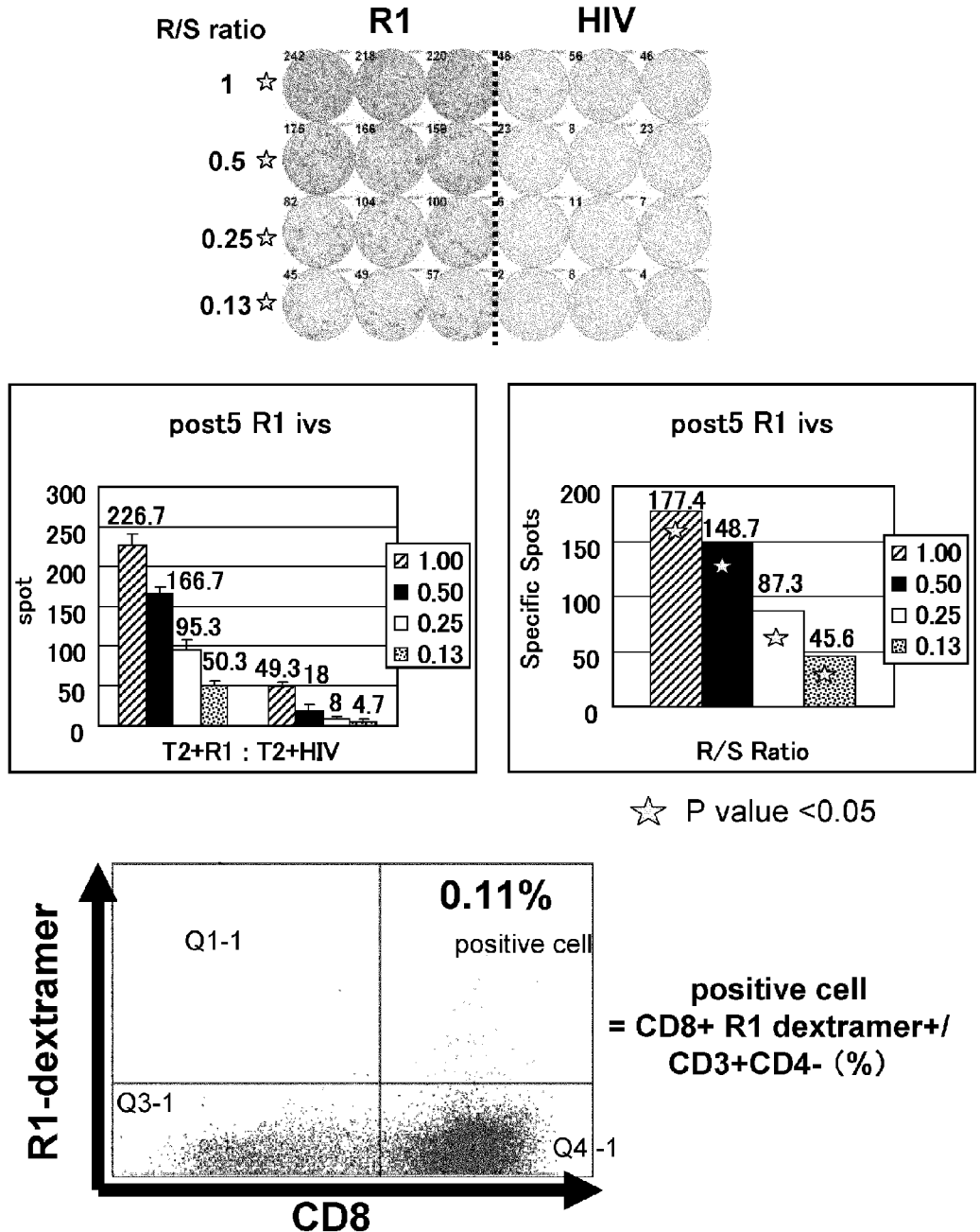
Figure 7:
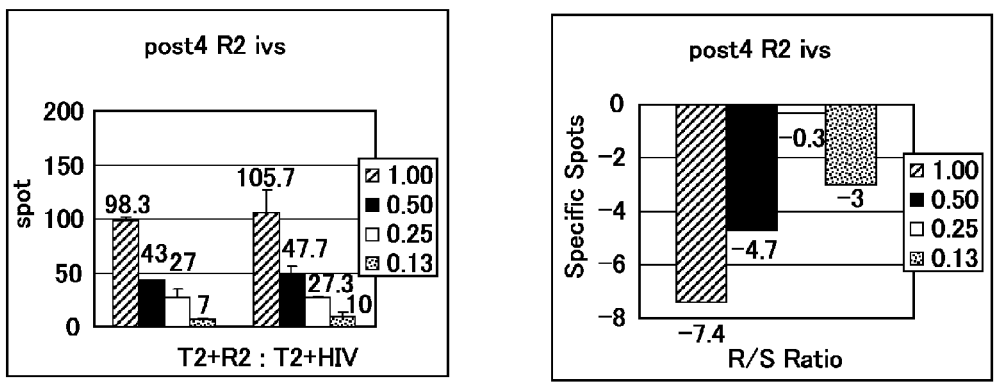
FIG. 7a-7c show the VEGFR2 peptide-specific response of HLA-A0201-Case3. The PBMCs of pre-treatment (a), post-1 course (b), and post-3 courses (c) were tested. In each figure, the number of spot counts against VEGFR2-A2-773 peptide-pulsed TISI or HIV-Env peptide-pulsed TISI (left panel) and VEGFR2 peptide-specific spots (right panel) is indicated in the graphs.
FIG. 7d-7e show the VEGFR2 peptide-specific response of HLA-A0201-Case3. The PBMCs of post-4 courses (d) and post-5 courses (e) were tested. In each figure, the number of spot counts against VEGFR2-A2-773 peptide-pulsed TISI or HIV-Env peptide-pulsed TISI (left panel) and VEGFR2 peptide-specific spots (right panel) is indicated in the graphs.
Figure 2:
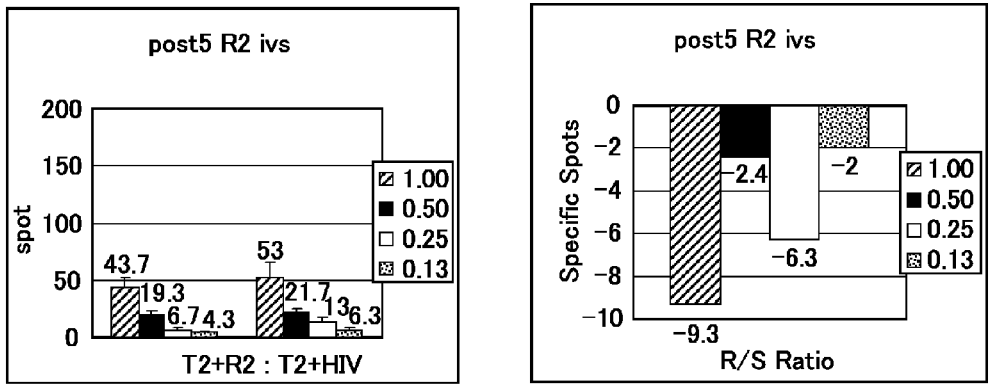

Significantly higher number of spots were observed when stimulated with VEGFR1-A2-770 peptide-pulsed T2 cells compared with that stimulated with HIV-Env peptide-pulsed T2 cells in IFN-gamma ELISPOT assay (Table 1 and FIG. 6). Consistently, significant population of HLA-A*0201/VEGFR1-A2-770 dextramer+CD8+ cells were detected by flow cytometric analysis (FIG. 6 lower panels). On the other hand, no specific IFN-gamma production was observed by stimulation with VEGFR2-A2-773 peptide (Table 1 and FIG. 7), despite administration of both VEGFR1-A2-770 peptide and VEGFR2-A2-773 peptide shown obvious efficacy in the patient. As a result, it indicated that VEGFR1-A2-770 peptide function to improve the case alone.

HLA-A2402-Case1

Figure 8:
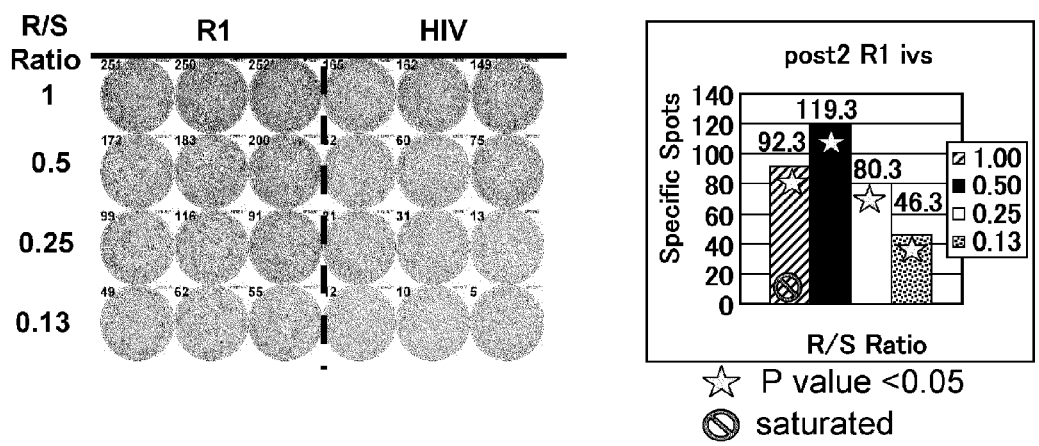
FIG. 8a-8b show the VEGFR1 peptide-specific response of HLA-A2402-Case1. The responses of the PBMCs of post-2 course (a) and post-6 courses (b) are shown as representative results. In each figure, the photograph of ELISPOT plate in which the PBMCs were stimulated by VEGFR1-A24-1084 peptide (left panel) or HIV-Env peptide (right panel) is shown. R/S; responder/stimulator ratio. The number of VEGFR1 peptide-specific spots is indicated in the graphs. Statistical analysis was performed using unpaired Student's t-test (Star mark; P<0.05). Circular mark indicates that spot counts are saturated.
Figure 8:
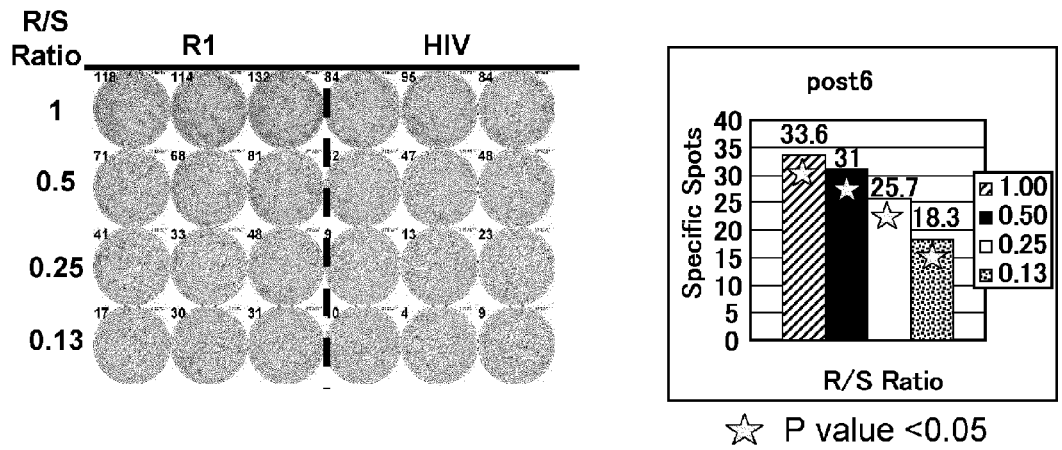
Figure 9:
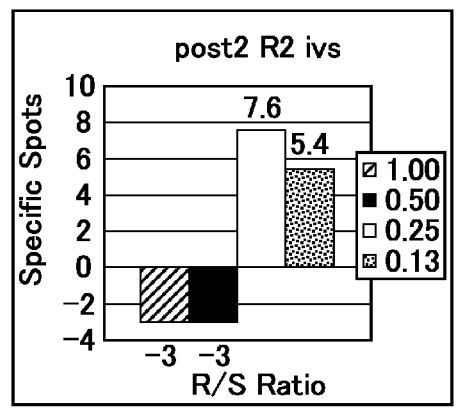
FIG. 9a-9b show the VEGFR2 peptide-specific response of HLA-A2402-Case1. The responses of the PBMCs of post-2 course (a) and post-6 courses (b) are shown as representative results. In each figure, the photograph of ELISPOT plate in which the PBMCs were stimulated by VEGFR2-A24-169 peptide (left panel) or HIV-Env peptide (right panel) is shown. R/S; responder/stimulator ratio. The number of VEGFR2 peptide-specific spots was indicated in the graphs.
Figure 9:
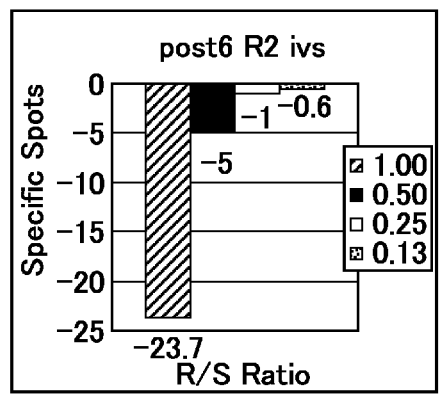

Significantly higher number of spots were observed when stimulated with VEGFR1-A24-1084 peptide-pulsed TISI cells compared with that stimulated with HIV-Env peptide-pulsed TISI cells in IFN-gamma ELISPOT assay, especially after treatment courses (Table 1 and FIG. 8). On the other hand, no specific IFN-gamma production was observed by stimulation with VEGFR2-A24-169 peptide (Table 1 and FIG. 9), despite administration of both VEGFR1-A24-1084 peptide and VEGFR2-A24-169 peptide shown obvious efficacy in the patient. As a result, it indicated that VEGFR1-A24-1084 peptide function to improve the case alone.

Change in Vision After Treatment

Figure 10:
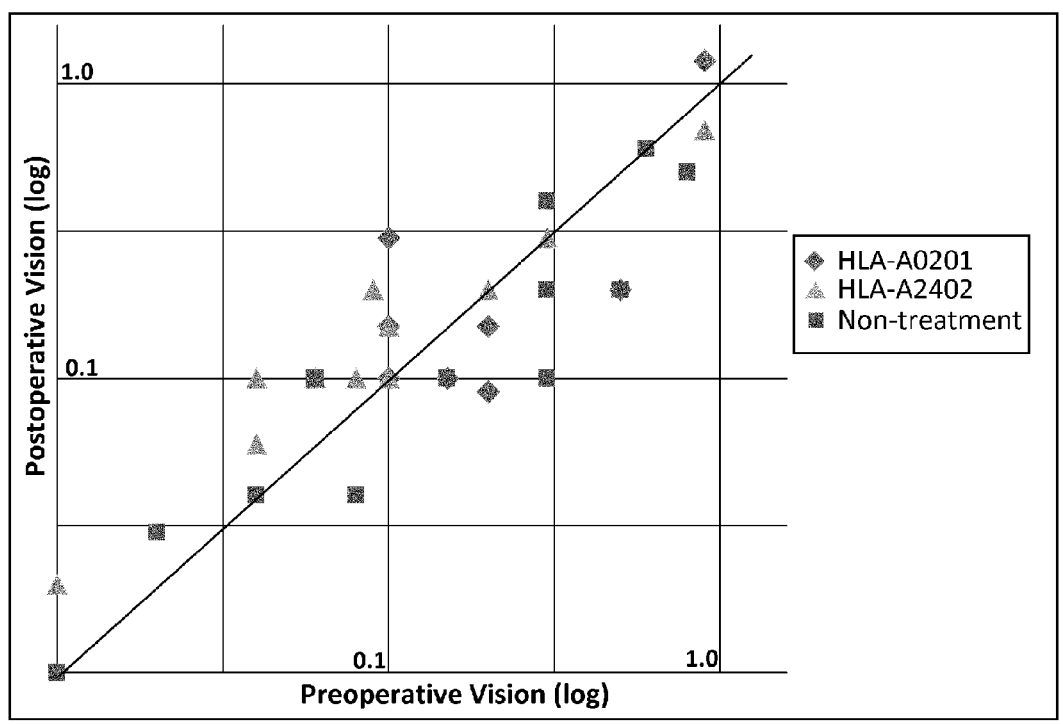
FIG. 10 shows the changes in vision of subjects after treatment. The visions of treatment groups were improved compared to non-treatment group with significant difference (p value=0.015).

The visions of treatment groups were improved with significant difference (p=0.015) (FIG. 10).

INDUSTRIAL APPLICABILITY

The present invention provides pharmaceutical compositions/vaccines for treatment and/or prevention of diseases caused by neovascularization in the choroid (neovascular maculopathy). Conventionally, laser therapy, photodynamic therapy, operative therapy, drug therapy, and such have been performed as therapeutic methods for neovascular maculopathy. However, laser therapy could reduce central vision. There are examples of rapid visual reduction following photodynamic therapy in cases with good vision. In operative therapy, there is a risk of postoperative complications associated with surgical invasion. In drug therapy, there is a risk of serious complications such as endophthalmitis and retinal detachment due to intraocular injection. That is, conventional therapies have a high risk of visual reduction due to treatment-associated adverse effects and complications. Therefore, it was difficult to treat early-stage cases with relatively good vision. Since safety problems did not arise in the administered cases, one can expect the pharmaceutical compositions/vaccines of the present invention to provide low-risk and highly safe therapeutic agents and therapeutic methods for neovascular maculopathy. Furthermore, since they are shown to be effective for cases that do not respond to conventional therapeutic methods, it can be expected that they will provide therapeutic agents and therapeutic methods for cases for which conventional therapeutic methods have not been effective.

The invention claimed is:

1. A method for treating a disease caused by neovascularization in human choroid, comprising the step of administering to a subject a pharmaceutical composition comprising, as active ingredients, at least one peptide selected from the group consisting of:
   (i) a peptide consisting of the amino acid sequence selected from the group consisting of SEQ ID NOs: 2 and 4;
   (ii) a peptide in which the second amino acid from the N terminus of the amino acid sequence of SEQ ID NO: 2 is modified to methionine;
   (iii) a peptide in which the C-terminal amino acid of the amino acid sequence of SEQ ID NO: 2 is modified to valine;
   (iv) a peptide in which the second amino acid from the N terminus of the amino acid sequence of SEQ ID NO: 2 is modified to methionine and the C-terminal amino acid of the amino acid sequence of SEQ ID NO: 2 is modified to valine;
   (v) a peptide in which the second amino acid from the N terminus of the amino acid sequence of SEQ ID NO: 4 is modified to phenylalanine, methionine or tryptophan;
   (vi) a peptide in which the C-terminal amino acid of the amino acid sequence of SEQ ID NO: 4 is modified to phenylalanine, leucine, tryptophan or methionine; and
   (vii) a peptide in which the second amino acid from the N terminus of the amino acid sequence of SEQ ID NO: 4 is modified to phenylalanine, methionine or tryptophan and the C-terminal amino acid of the amino acid sequence of SEQ ID NO: 4 is modified to phenylalanine, leucine, tryptophan or methionine, and
   at least one peptide selected from the group consisting of:
   (viii) a peptide consisting of the amino acid sequence selected from the group consisting of SEQ ID NOs: 8 and 12; and
   (ix) a peptide in which the second amino acid from the N terminus of the amino acid sequence of SEQ ID NO: 12 is modified to leucine or methionine;
   (x) a peptide in which the C-terminal amino acid of the amino acid sequence of SEQ ID NO: 12 is modified to valine;
   (xi) a peptide in which the second amino acid from the N terminus of the amino acid sequence of SEQ ID NO: 12 is modified to leucine or methionine and the C-terminal amino acid of the amino acid sequence of SEQ ID NO: 12 is modified to valine;
   (xii) a peptide in which the second amino acid from the N terminus of the amino acid sequence of SEQ ID NO: 8 is modified to tyrosine, methionine or tryptophan;
   (xiii) a peptide in which the C-terminal amino acid of the amino acid sequence of SEQ ID NO: 8 is modified to phenylalanine, leucine, tryptophan or methionine; and
   (xiv) a peptide in which the second amino acid from the N terminus of the amino acid sequence of SEQ ID NO: 8 is modified to tyrosine, methionine or tryptophan and the C-terminal amino acid of the amino acid sequence of SEQ ID NO: 8 is modified to phenylalanine, leucine, tryptophan or methionine.

2. The method of claim 1, wherein the disease caused by neovascularization in the choroid is selected from exudative age-related macular degeneration, myopic macular degeneration, angioid streaks, central exudative chorioretinopathy, various retinal pigment epitheliopathy, choroidal atrophy, choroideremia, and choroidal osteoma.

3. The method of claim 1, which is administered to a subject whose HLA antigen is HLA-A02 or HLA-A24.

4. A method of treating a disease caused by neovascularization in human choroid, comprising the step of administering to a subject a vaccine comprising, as active ingredients, at least one peptide selected from the group consisting of:
   (i) a peptide consisting of the amino acid sequence selected from the group consisting of SEQ ID NOs: 2 and 4;
   (ii) a peptide in which the second amino acid from the N terminus of the amino acid sequence of SEQ ID NO: 2 is modified to methionine;
   (iii) a peptide in which the C-terminal amino acid of the amino acid sequence of SEQ ID NO: 2 is modified to valine;
   (iv) a peptide in which the second amino acid from the N terminus of the amino acid sequence of SEQ ID NO: 2 is modified to methionine and the C-terminal amino acid of the amino acid sequence of SEQ ID NO: 2 is modified to valine;
   (v) a peptide in which the second amino acid from the N terminus of the amino acid sequence of SEQ ID NO: 4 is modified to phenylalanine, methionine or tryptophan;
   (vi) a peptide in which the C-terminal amino acid of the amino acid sequence of SEQ ID NO: 4 is modified to phenylalanine, leucine, tryptophan or methionine; and
   (vii) a peptide in which the second amino acid from the N terminus of the amino acid sequence of SEQ ID NO: 4 is modified to phenylalanine, methionine or tryptophan and the C-terminal amino acid of the amino acid sequence of SEQ ID NO: 4 is modified to phenylalanine, leucine, tryptophan or methionine,
   and at least one peptide selected from the group consisting of:
   (viii) a peptide consisting of the amino acid sequence selected from the group consisting of SEQ ID NOs: 8 and 12; and
   (ix) a peptide in which the second amino acid from the N terminus of the amino acid sequence of SEQ ID NO: 12 is modified to leucine or methionine;
   (x) a peptide in which the C-terminal amino acid of the amino acid sequence of SEQ ID NO: 12 is modified to valine;
   (xi) a peptide in which the second amino acid from the N terminus of the amino acid sequence of SEQ ID NO: 12 is modified to leucine or methionine and the C-terminal amino acid of the amino acid sequence of SEQ ID NO: 12 is modified to valine;
   (xii) a peptide in which the second amino acid from the N terminus of the amino acid sequence of SEQ ID NO: 8 is modified to tyrosine, methionine or tryptophan;
   (xiii) a peptide in which the C-terminal amino acid of the amino acid sequence of SEQ ID NO: 8 is modified to phenylalanine, leucine, tryptophan or methionine; and
   (xiv) a peptide in which the second amino acid from the N terminus of the amino acid sequence of SEQ ID NO: 8 is modified to tyrosine, methionine or tryptophan and the C-terminal amino acid of the amino acid sequence of SEQ ID NO: 8 is modified to phenylalanine, leucine, tryptophan or methionine.

5. The method of claim 4, wherein the disease caused by neovascularization in the choroid is selected from exudative age-related macular degeneration, myopic macular degeneration, angioid streaks, central exudative chorioretinopathy, various retinal pigment epitheliopathy, choroidal atrophy, choroideremia, and choroidal osteoma.

6. The method of claim 4, which is administered to a subject whose HLA antigen is HLA-A02 or HLA-A24.

7. A method for inhibiting neovascularization in human choroid, comprising the step of administering to a subject a pharmaceutical composition comprising, as active ingredients, at least one peptide selected from the group consisting of:
- (i) a peptide consisting of the amino acid sequence selected from the group consisting of SEQ ID NOs: 2 and 4;
- (ii) a peptide in which the second amino acid from the N terminus of the amino acid sequence of SEQ ID NO: 2 is modified to methionine;
- (iii) a peptide in which the C-terminal amino acid of the amino acid sequence of SEQ ID NO: 2 is modified to valine;
- (iv) a peptide in which the second amino acid from the N terminus of the amino acid sequence of SEQ ID NO: 2 is modified to methionine and the C-terminal amino acid of the amino acid sequence of SEQ ID NO: 2 is modified to valine;
- (v) a peptide in which the second amino acid from the N terminus of the amino acid sequence of SEQ ID NO: 4 is modified to phenylalanine, methionine or tryptophan;
- (vi) a peptide in which the C-terminal amino acid of the amino acid sequence of SEQ ID NO: 4 is modified to phenylalanine, leucine, tryptophan or methionine; and
- (vii) a peptide in which the second amino acid from the N terminus of the amino acid sequence of SEQ ID NO: 4 is modified to phenylalanine, methionine or tryptophan and the C-terminal amino acid of the amino acid sequence of SEQ ID NO: 4 is modified to phenylalanine, leucine, tryptophan or methionine, and at least one peptide selected from the group consisting of:
- (viii) a peptide consisting of the amino acid sequence selected from the group consisting of SEQ ID NOs: 8 and 12; and
- (ix) a peptide in which the second amino acid from the N terminus of the amino acid sequence of SEQ ID NO: 12 is modified to leucine or methionine;
- (x) a peptide in which the C-terminal amino acid of the amino acid sequence of SEQ ID NO: 12 is modified to valine;
- (xi) a peptide in which the second amino acid from the N terminus of the amino acid sequence of SEQ ID NO: 12 is modified to leucine or methionine and the C-terminal amino acid of the amino acid sequence of SEQ ID NO: 12 is modified to valine;
- (xii) a peptide in which the second amino acid from the N terminus of the amino acid sequence of SEQ ID NO: 8 is modified to tyrosine, methionine or tryptophan;
- (xiii) a peptide in which the C-terminal amino acid of the amino acid sequence of SEQ ID NO: 8 is modified to phenylalanine, leucine, tryptophan or methionine; and
- (xiv) a peptide in which the second amino acid from the N terminus of the amino acid sequence of SEQ ID NO: 8 is modified to tyrosine, methionine or tryptophan and the C-terminal amino acid of the amino acid sequence of SEQ ID NO: 8 is modified to phenylalanine, leucine, tryptophan or methionine.

8. The method of claim 7, which is administered to a subject whose HLA antigen is HLA-A02 or HLA-A24.

9. A method for inhibiting neovascularization in human choroid, comprising the step of administering to a subject a vaccine comprising, as active ingredients, at least one peptide selected from the group consisting of:
- (i) a peptide consisting of the amino acid sequence selected from the group consisting of SEQ ID NOs: 2 and 4,
- (ii) a peptide in which the second amino acid from the N terminus of the amino acid sequence of SEQ ID NO: 2 is modified to methionine;
- (iii) a peptide in which the C-terminal amino acid of the amino acid sequence of SEQ ID NO: 2 is modified to valine;
- (iv) a peptide in which the second amino acid from the N terminus of the amino acid sequence of SEQ ID NO: 2 is modified to methionine and the C-terminal amino acid of the amino acid sequence of SEQ ID NO: 2 is modified to valine;
- (v) a peptide in which the second amino acid from the N terminus of the amino acid sequence of SEQ ID NO: 4 is modified to phenylalanine, methionine or tryptophan;
- (vi) a peptide in which the C-terminal amino acid of the amino acid sequence of SEQ ID NO: 4 is modified to phenylalanine, leucine, tryptophan or methionine; and
- (vii) a peptide in which the second amino acid from the N terminus of the amino acid sequence of SEQ ID NO: 4 is modified to phenylalanine, methionine or tryptophan and the C-terminal amino acid of the amino acid sequence of SEQ ID NO: 4 is modified to phenylalanine, leucine, tryptophan or methionine, and at least one peptide selected from the group consisting of:
- (viii) a peptide consisting of the amino acid sequence selected from the group consisting of SEQ ID NOs: 8 and 12; and
- (ix) a peptide in which the second amino acid from the N terminus of the amino acid sequence of SEQ ID NO: 12 is modified to leucine or methionine;
- (x) a peptide in which the C-terminal amino acid of the amino acid sequence of SEQ ID NO: 12 is modified to valine;
- (xi) a peptide in which the second amino acid from the N terminus of the amino acid sequence of SEQ ID NO: 12 is modified to leucine or methionine and the C-terminal amino acid of the amino acid sequence of SEQ ID NO: 12 is modified to valine;
- (xii) a peptide in which the second amino acid from the N terminus of the amino acid sequence of SEQ ID NO: 8 is modified to tyrosine, methionine or tryptophan;
- (xiii) a peptide in which the C-terminal amino acid of the amino acid sequence of SEQ ID NO: 8 is modified to phenylalanine, leucine, tryptophan or methionine; and
- (xiv) a peptide in which the second amino acid from the N terminus of the amino acid sequence of SEQ ID NO: 8 is modified to tyrosine, methionine or tryptophan and the C-terminal amino acid of the amino acid sequence of SEQ ID NO: 8 is modified to phenylalanine, leucine, tryptophan or methionine.

10. The method of claim 9, which is administered to a subject whose HLA antigen is HLA-A02 or HLA-A24.

11. The method of claim 1, wherein the amount of the peptide selected from the group consisting of (i) to (vii) is 0.1 mg to 10 mg.

12. The method of claim 11, wherein the amount of the peptide selected from the group consisting of (viii) to (xiv) is the same amount as the peptide selected from the group consisting of (i) to (vii).

13. The method of claim 4, wherein the amount of the peptide selected from the group consisting of (i) to (vii) is 0.1 mg to 10 mg.

14. The method of claim 13, wherein the amount of the peptide selected from the group consisting of (viii) to (xiv) is the same amount as the peptide selected from the group consisting of (i) to (vii).

15. The method of claim 4, wherein the vaccine is administered together with an adjuvant.

16. The method of claim 15, wherein the adjuvant is incomplete Freund's adjuvant.

17. The method of claim 7, wherein the amount of the peptide selected from the group consisting of (i) to (vii) is 0.1 mg to 10 mg.

18. The method of claim 17, wherein the amount of the peptide selected from the group consisting of (viii) to (xiv) is the same amount as the peptide selected from the group consisting of (i) to (vii).

19. The method of claim 9, wherein the amount of the peptide selected from the group consisting of (i) to (vii) is 0.1 mg to 10 mg.

20. The method of claim 19, wherein the amount of the peptide selected from the group consisting of (viii) to (xiv) is the same amount as the peptide selected from the group consisting of (i) to (vii).

21. The method of claim 9, wherein the vaccine is administered together with an adjuvant.

22. The method of claim 21, wherein the adjuvant is incomplete Freund's adjuvant.

* * * * *

```
SEQUENCE LISTING

<160> NUMBER OF SEQ ID NOS: 23

<210> SEQ ID NO 1
<211> LENGTH: 9
<212> TYPE: PRT
<213> ORGANISM: Artificial
<220> FEATURE:
<223> OTHER INFORMATION: a synthesized epitope peptide

<400> SEQUENCE: 1

Val Leu Leu Trp Glu Ile Phe Ser Leu
1               5

<210> SEQ ID NO 2
<211> LENGTH: 9
<212> TYPE: PRT
<213> ORGANISM: Artificial
<220> FEATURE:
<223> OTHER INFORMATION: a synthesized epitope peptide

<400> SEQUENCE: 2

Thr Leu Phe Trp Leu Leu Leu Thr Leu
1               5

<210> SEQ ID NO 3
<211> LENGTH: 10
<212> TYPE: PRT
<213> ORGANISM: Artificial
<220> FEATURE:
<223> OTHER INFORMATION: a synthesized epitope peptide

<400> SEQUENCE: 3

Asn Leu Thr Ala Thr Leu Ile Val Asn Val
1               5                   10

<210> SEQ ID NO 4
<211> LENGTH: 9
<212> TYPE: PRT
<213> ORGANISM: Artificial
<220> FEATURE:
<223> OTHER INFORMATION: a synthesized epitope peptide

<400> SEQUENCE: 4

Ser Tyr Gly Val Leu Leu Trp Glu Ile
1               5
```

```
<210> SEQ ID NO 5
<211> LENGTH: 9
<212> TYPE: PRT
<213> ORGANISM: Artificial
<220> FEATURE:
<223> OTHER INFORMATION: a synthesized epitope peptide

<400> SEQUENCE: 5

Val Tyr Ser Ser Glu Glu Ala Glu Leu
1               5

<210> SEQ ID NO 6
<211> LENGTH: 9
<212> TYPE: PRT
<213> ORGANISM: Artificial
<220> FEATURE:
<223> OTHER INFORMATION: a synthesized epitope peptide

<400> SEQUENCE: 6

Gly Tyr Arg Ile Tyr Asp Val Val Leu
1               5

<210> SEQ ID NO 7
<211> LENGTH: 9
<212> TYPE: PRT
<213> ORGANISM: Artificial
<220> FEATURE:
<223> OTHER INFORMATION: a synthesized epitope peptide

<400> SEQUENCE: 7

Ser Tyr Met Ile Ser Tyr Ala Gly Met
1               5

<210> SEQ ID NO 8
<211> LENGTH: 9
<212> TYPE: PRT
<213> ORGANISM: Artificial
<220> FEATURE:
<223> OTHER INFORMATION: a synthesized epitope peptide

<400> SEQUENCE: 8

Arg Phe Val Pro Asp Gly Asn Arg Ile
1               5

<210> SEQ ID NO 9
<211> LENGTH: 9
<212> TYPE: PRT
<213> ORGANISM: Artificial
<220> FEATURE:
<223> OTHER INFORMATION: a synthesized epitope peptide

<400> SEQUENCE: 9

Lys Trp Glu Phe Pro Arg Asp Arg Leu
1               5

<210> SEQ ID NO 10
<211> LENGTH: 9
<212> TYPE: PRT
<213> ORGANISM: Artificial
<220> FEATURE:
<223> OTHER INFORMATION: a synthesized epitope peptide

<400> SEQUENCE: 10

Asp Phe Leu Thr Leu Glu His Leu Ile
1               5
```

```
<210> SEQ ID NO 11
<211> LENGTH: 9
<212> TYPE: PRT
<213> ORGANISM: Artificial
<220> FEATURE:
<223> OTHER INFORMATION: a synthesized epitope peptide

<400> SEQUENCE: 11

Ala Met Phe Phe Trp Leu Leu Leu Val
1               5

<210> SEQ ID NO 12
<211> LENGTH: 9
<212> TYPE: PRT
<213> ORGANISM: Artificial
<220> FEATURE:
<223> OTHER INFORMATION: a synthesized epitope peptide

<400> SEQUENCE: 12

Val Ile Ala Met Phe Phe Trp Leu Leu
1               5

<210> SEQ ID NO 13
<211> LENGTH: 9
<212> TYPE: PRT
<213> ORGANISM: Artificial
<220> FEATURE:
<223> OTHER INFORMATION: a synthesized epitope peptide

<400> SEQUENCE: 13

Ala Val Ile Ala Met Phe Phe Trp Leu
1               5

<210> SEQ ID NO 14
<211> LENGTH: 9
<212> TYPE: PRT
<213> ORGANISM: Artificial
<220> FEATURE:
<223> OTHER INFORMATION: a synthesized epitope peptide

<400> SEQUENCE: 14

Lys Leu Ile Glu Ile Gly Val Gln Thr
1               5

<210> SEQ ID NO 15
<211> LENGTH: 9
<212> TYPE: PRT
<213> ORGANISM: Artificial
<220> FEATURE:
<223> OTHER INFORMATION: a synthesized epitope peptide

<400> SEQUENCE: 15

Tyr Met Ile Ser Tyr Ala Gly Met Val
1               5

<210> SEQ ID NO 16
<211> LENGTH: 10
<212> TYPE: PRT
<213> ORGANISM: Artificial
<220> FEATURE:
<223> OTHER INFORMATION: a synthesized epitope peptide

<400> SEQUENCE: 16

Ile Gln Ser Asp Val Trp Ser Phe Gly Val
1               5                   10
```

<210> SEQ ID NO 17
<211> LENGTH: 9
<212> TYPE: PRT
<213> ORGANISM: Artificial
<220> FEATURE:
<223> OTHER INFORMATION: a synthesized epitope peptide

<400> SEQUENCE: 17

Val Leu Ala Met Phe Phe Trp Leu Leu
1               5

<210> SEQ ID NO 18
<211> LENGTH: 7123
<212> TYPE: DNA
<213> ORGANISM: Homo sapiens

<400> SEQUENCE: 18

| | | | | | |
|---|---|---|---|---|---|
| atcgaggtcc | gcgggaggct | cggagcgcgc | caggcggaca | ctcctctcgg | ctcctccccg | 60 |
| gcagcggcgg | cggctcggag | cgggctccgg | ggctcgggtg | cagcggccag | cgggcgcctg | 120 |
| gcggcgagga | ttacccgggg | aagtggttgt | ctcctggctg | gagccgcgag | acgggcgctc | 180 |
| agggcgcggg | gccggcggcg | gcgaacgaga | ggacggactc | tggcggccgg | gtcgttggcc | 240 |
| gcggggagcg | cgggcaccgg | gcgagcaggc | cgcgtcgcgc | tcaccatggt | cagctactgg | 300 |
| gacaccgggg | tcctgctgtg | cgcgctgctc | agctgtctgc | ttctcacagg | atctagttca | 360 |
| ggttcaaaat | taaaagatcc | tgaactgagt | ttaaaaggca | cccagcacat | catgcaagca | 420 |
| ggccagacac | tgcatctcca | atgcaggggg | gaagcagccc | ataaatggtc | tttgcctgaa | 480 |
| atggtgagta | aggaaagcga | aaggctgagc | ataactaaat | ctgcctgtgg | aagaaatggc | 540 |
| aaacaattct | gcagtacttt | aaccttgaac | acagctcaag | caaaccacac | tggcttctac | 600 |
| agctgcaaat | atctagctgt | acctacttca | agaagaagg | aaacagaatc | tgcaatctat | 660 |
| atatttatta | gtgatacagg | tagacctttc | gtagagatgt | acagtgaaat | ccccgaaatt | 720 |
| atacacatga | ctgaaggaag | ggagctcgtc | attccctgcc | gggttacgtc | acctaacatc | 780 |
| actgttactt | taaaaaagtt | tccacttgac | actttgatcc | ctgatggaaa | acgcataatc | 840 |
| tgggacagta | gaaagggctt | catcatatca | aatgcaacgt | acaaagaaat | agggcttctg | 900 |
| acctgtgaag | caacagtcaa | tgggcatttg | tataagacaa | actatctcac | acatcgacaa | 960 |
| accaatacaa | tcatagatgt | ccaaataagc | acaccacgcc | cagtcaaatt | acttagaggc | 1020 |
| catactcttg | tcctcaattg | tactgctacc | actcccttga | acacgagagt | tcaaatgacc | 1080 |
| tggagttacc | ctgatgaaaa | aaataagaga | gcttccgtaa | ggcgacgaat | tgaccaaagc | 1140 |
| aattcccatg | ccaacatatt | ctacagtgtt | cttactattg | acaaaatgca | gaacaaagac | 1200 |
| aaaggacttt | atacttgtcg | tgtaaggagt | ggaccatcat | tcaaatctgt | taacacctca | 1260 |
| gtgcatatat | atgataaagc | attcatcact | gtgaaacatc | gaaaacagca | ggtgcttgaa | 1320 |
| accgtagctg | gcaagcggtc | ttaccggctc | tctatgaaag | tgaaggcatt | tccctcgccg | 1380 |
| gaagttgtat | ggttaaaaga | tgggttacct | gcgactgaga | atctgctcg | ctatttgact | 1440 |
| cgtggctact | cgttaattat | caaggacgta | actgaagagg | atgcagggaa | ttatacaatc | 1500 |
| ttgctgagca | taaacagtc | aaatgtgttt | aaaaacctca | ctgccactct | aattgtcaat | 1560 |
| gtgaaacccc | agatttacga | aaaggccgtg | tcatcgtttc | cagacccggc | tctctaccca | 1620 |
| ctgggcagca | gacaaatcct | gacttgtacc | gcatatggta | tccctcaacc | tacaatcaag | 1680 |
| tggttctggc | accctgtaa | ccataatcat | tccgaagcaa | ggtgtgactt | tgttccaat | 1740 |
| aatgaagagt | cctttatcct | ggatgctgac | agcaacatgg | gaaacagaat | tgagagcatc | 1800 |

```
actcagcgca tggcaataat agaaggaaag aataagatgg ctagcacctt ggttgtggct    1860
gactctagaa tttctggaat ctacatttgc atagcttcca ataaagttgg gactgtggga    1920
agaaacataa gcttttatat cacagatgtg ccaaatgggt ttcatgttaa cttggaaaaa    1980
atgccgacgg aaggagagga cctgaaactg tcttgcacag ttaacaagtt cttatacaga    2040
gacgttactt ggattttact gcggacagtt aataacagaa caatgcacta cagtattagc    2100
aagcaaaaaa tggccatcac taaggagcac tccatcactc ttaatcttac catcatgaat    2160
gtttccctgc aagattcagg cacctatgcc tgcagagcca ggaatgtata cacaggggaa    2220
gaaatcctcc agaagaaaga aattacaatc agagatcagg aagcaccata cctcctgcga    2280
aacctcagtg atcacacagt ggccatcagc agttccacca ctttagactg tcatgctaat    2340
ggtgtccccg agcctcagat cacttggttt aaaaacaacc acaaaataca acaagagcct    2400
ggaattattt taggaccagg aagcagcacg ctgtttattg aaagagtcac agaagaggat    2460
gaaggtgtct atcactgcaa agccaccaac cagaagggct ctgtggaaag ttcagcatac    2520
ctcactgttc aaggaacctc ggacaagtct aatctgagc tgatcactct aacatgcacc     2580
tgtgtggctg cgactctctt ctggctccta ttaaccctct ttatccgaaa aatgaaaagg    2640
tcttcttctg aaataaagac tgactaccta tcaattataa tggacccaga tgaagttcct    2700
ttggatgagc agtgtgagcg gctcccttat gatgccagca gtgggagtt tgcccgggag     2760 agacttaaac tgggcaaatc acttggaaga ggggcttttg aaaagtggt tcaagcatca     2820 gcatttggca ttaagaaatc acctacgtgc cggactgtgg ctgtgaaaat gctgaaagag    2880
ggggccacgg ccagcgagta caaagctctg atgactgagc taaaaatctt gacccacatt    2940
ggccaccatc tgaacgtggt taacctgctg ggagcctgca ccaagcaagg agggcctctg    3000
atggtgattg ttgaatactg caaatatgga aatctctcca actacctcaa gagcaaacgt    3060
gacttatttt ttctcaacaa ggatgcagca ctacacatgg agcctaagaa agaaaaaatg    3120
gagccaggcc tggaacaagg caagaaacca agactagata gcgtcaccag cagcgaaagc    3180
tttgcgagct ccggctttca ggaagataaa agtctgagtg atgttgagga agaggaggat    3240
tctgacggtt tctacaagga gcccatcact atggaagatc tgatttctta cagttttcaa    3300
gtggccagag gcatggagtt cctgtcttcc agaaagtgca ttcatcggga cctggcagcg    3360
agaaacattc ttttatctga gaacaacgtg gtgaagattt gtgattttgg ccttgcccgg    3420
gatatttata agaaccccga ttatgtgaga aaggagata ctcgacttcc tctgaaatgg     3480
atggctcctg aatctatctt tgacaaaatc tacagcacca gagcgacgt gtggtcttac     3540 ggagtattgc tgtgggaaat cttctcctta ggtgggtctc catacccagg agtacaaatg    3600
gatgaggact tttgcagtcg cctgagggaa ggcatgagga tgagagctcc tgagtactct    3660
actcctgaaa tctatcagat catgctggac tgctggcaca gagacccaaa agaaaggcca    3720
agatttgcag aacttgtgga aaaactaggt gatttgcttc aagcaaatgt acaacaggat    3780
ggtaaagact acatcccaat caatgccata ctgacaggaa atagtgggtt tacatactca    3840
actcctgcct tctctgagga cttcttcaag gaaagtattt cagctccgaa gtttaattca    3900
ggaagctctg atgatgtcag atacgtaaat gctttcaagt tcatgagcct ggaaagaatc    3960
aaaacctttg aagaactttt accgaatgcc acctccatgt ttgatgacta ccagggcgac    4020
agcagcactc tgttggcctc tcccatgctg aagcgcttca cctggactga cagcaaaccc    4080
aaggcctcgc tcaagattga cttgagagta accagtaaaa gtaaggagtc ggggctgtct    4140
gatgtcagca ggcccagttt ctgccattcc agctgtgggc acgtcagcga aggcaagcgc    4200
```

```
aggttcacct acgaccacgc tgagctggaa aggaaaatcg cgtgctgctc cccgccccca   4260
gactacaact cggtggtcct gtactccacc ccacccatct agagtttgac acgaagcctt   4320
atttctagaa gcacatgtgt atttataccc ccaggaaact agcttttgcc agtattatgc   4380
atatataagt ttacaccttt atcttttccat gggagccagc tgcttttttgt gatttttta   4440 atagtgcttt ttttttttg actaacaaga atgtaactcc agatagagaa atagtgacaa   4500
gtgaagaaca ctactgctaa atcctcatgt tactcagtgt tagagaaatc cttcctaaac   4560
ccaatgactt ccctgctcca accccgcca cctcagggca cgcaggacca gtttgattga   4620
ggagctgcac tgatcaccca atgcatcacg tacccactg ggccagccct gcagcccaaa   4680
acccagggca acaagcccgt tagccccagg gatcactggc tggcctgagc aacatctcgg   4740
gagtcctcta gcaggcctaa gacatgtgag gaggaaaagg aaaaaaagca aaaagcaagg   4800
gagaaaagag aaaccgggag aaggcatgag aaagaatttg agacgcacca tgtgggcacg   4860 gaggggacg gggctcagca atgccatttc agtggcttcc cagctctgac ccttctacat   4920
ttgagggccc agccaggagc agatggacag cgatgagggg acattttctg gattctggga   4980
ggcaagaaaa ggacaaatat cttttttgga actaaagcaa attttagaac tttacctatg   5040
gaagtggttc tatgtccatt ctcattcgtg gcatgttttg atttgtagca ctgagggtgg   5100
cactcaactc tgagcccata cttttggctc ctctagtaag atgcactgaa aacttagcca   5160
gagttaggtt gtctccaggc catgatggcc ttacactgaa aatgtcacat tctatttgg    5220 gtattaatat atagtccaga cacttaactc aatttcttgg tattattctg ttttgcacag   5280
ttagttgtga aagaaagctg agaagaatga aaatgcagtc ctgaggagag gagttttctc   5340
catatcaaaa cgagggctga tggaggaaaa aggtcaataa ggtcaaggga aaaccccgtc   5400
tctataccaa ccaaaccaat tcaccaacac agttgggacc caaaacacag gaagtcagtc   5460
acgtttcctt ttcatttaat ggggattcca ctatctcaca ctaatctgaa aggatgtgga   5520
agagcattag ctggcgcata ttaagcactt taagctcctt gagtaaaaag gtggtatgta   5580
atttatgcaa ggtatttctc cagttgggac tcaggatatt agttaatgag ccatcactag   5640
aagaaaagcc cattttcaac tgcttttgaaa cttgcctggg gtctgagcat gatgggaata   5700
gggagacagg gtaggaaagg gcgcctactc ttcagggtct aaagatcaag tgggccttgg   5760
atcgctaagc tggctctgtt tgatgctatt tatgcaagtt agggtctatg tatttatgat   5820
gtctgcacct tctgcagcca gtcagaagct ggagaggcaa cagtggattg ctgcttcttg   5880 gggagaaag tatgcttcct tttatccatg taatttaact gtagaacctg agctctaagt   5940
aaccgaagaa tgtatgcctc tgttcttatg tgccacatcc ttgtttaaag gctctctgta   6000
tgaagagatg ggaccgtcat cagcacattc cctagtgagc ctactggctc ctggcagcgg   6060
cttttgtgga agactcacta gccagaagag aggagtggga cagtcctctc caccaagatc   6120
taaatccaaa caaaagcagg ctagagccaa aagagaggac aaatcttgt tcttcctctt    6180 ctttacatac gcaaaccacc tgtgcacagct ggcaatttta taaatcaggt aactggaagg   6240
aggttaaaca cagaaaaag aagacctcag tcaattctct acttttttt ttttttccaa     6300 atcagataat agcccagcaa atagtgataa caaataaaac cttagctatt catgtcttga   6360
tttcaataat taattcttaa tcattaagag accataataa atactccttt tcaagagaaa   6420
agcaaaacca ttagaattgt tactcagctc cttcaaactc aggtttgtag catacatgag   6480
tccatccatc agtcaaagaa tggttccatc tggagtctta atgtagaaag aaaaatggag   6540
acttgtaata atgagctagt tacaaagtgc ttgttcatta aaatagcact gaaaattgaa   6600
```

-continued

```
acatgaatta actgataata ttccaatcat ttgccattta tgacaaaaat ggttggcact    6660
aacaaagaac gagcacttcc tttcagagtt tctgagataa tgtacgtgga acagtctggg    6720
tggaatgggg ctgaaaccat gtgcaagtct gtgtcttgtc agtccaagaa gtgacaccga    6780
gatgttaatt ttagggaccc gtgccttgtt tcctagccca caagaatgca acatcaaac     6840 agatactcgc tagcctcatt taaattgatt aaaggaggag tgcatctttg gccgacagtg    6900
gtgtaactgt atgtgtgtgt gtgtgtgtgt gtgtgtgtgt gtgtgtgggt gtatgtgtgt    6960
tttgtgcata actatttaag gaaactggaa ttttaaagtt acttttatac aaaccaagaa    7020
tatatgctac agatataaga cagacatggt ttggtcctat atttctagtc atgatgaatg    7080
tattttgtat accatcttca tataataaac ttccaaaaac aca                     7123
```

<210> SEQ ID NO 19
<211> LENGTH: 1338
<212> TYPE: PRT
<213> ORGANISM: Homo sapiens

<400> SEQUENCE: 19

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285
```

-continued

```
Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
            530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700
```

-continued

```
Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
        740                 745                 750

Asp Lys Ser Asn Leu Glu Leu Ile Thr Leu Thr Cys Thr Cys Val Ala
    755                 760                 765

Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
        820                 825                 830

Leu Gly Arg Gly Ala Phe Gly Lys Val Val Gln Ala Ser Ala Phe Gly
    835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
        900                 905                 910

Lys Tyr Gly Asn Leu Ser Asn Tyr Leu Lys Ser Lys Arg Asp Leu Phe
    915                 920                 925

Phe Leu Asn Lys Asp Ala Ala Leu His Met Glu Pro Lys Lys Glu Lys
930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
        980                 985                 990

Pro Ile Thr Met Glu Asp Leu Ile Ser Tyr Ser Phe Gln Val Ala Arg
    995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110
```

| | | | | | | | | | |
|---|---|---|---|---|---|---|---|---|---|
|Arg|Glu|Gly|Met|Arg|Met|Arg|Ala|Pro|Glu|Tyr|Ser|Thr|Pro|Glu|
|1115| | | | |1120| | | |1125| | | | | |

Ile Tyr Gln Ile Met Leu Asp Cys Trp His Arg Asp Pro Lys Glu
 1130             1135                 1140

Arg Pro Arg Phe Ala Glu Leu Val Glu Lys Leu Gly Asp Leu Leu
 1145             1150                 1155

Gln Ala Asn Val Gln Gln Asp Gly Lys Asp Tyr Ile Pro Ile Asn
 1160             1165                 1170

Ala Ile Leu Thr Gly Asn Ser Gly Phe Thr Tyr Ser Thr Pro Ala
 1175             1180                 1185

Phe Ser Glu Asp Phe Phe Lys Glu Ser Ile Ser Ala Pro Lys Phe
 1190             1195                 1200

Asn Ser Gly Ser Ser Asp Asp Val Arg Tyr Val Asn Ala Phe Lys
 1205             1210                 1215

Phe Met Ser Leu Glu Arg Ile Lys Thr Phe Glu Glu Leu Leu Pro
 1220             1225                 1230

Asn Ala Thr Ser Met Phe Asp Asp Tyr Gln Gly Asp Ser Ser Thr
 1235             1240                 1245

Leu Leu Ala Ser Pro Met Leu Lys Arg Phe Thr Trp Thr Asp Ser
 1250             1255                 1260

Lys Pro Lys Ala Ser Leu Lys Ile Asp Leu Arg Val Thr Ser Lys
 1265             1270                 1275

Ser Lys Glu Ser Gly Leu Ser Asp Val Ser Arg Pro Ser Phe Cys
 1280             1285                 1290

His Ser Ser Cys Gly His Val Ser Glu Gly Lys Arg Arg Phe Thr
 1295             1300                 1305

Tyr Asp His Ala Glu Leu Glu Arg Lys Ile Ala Cys Cys Ser Pro
 1310             1315                 1320

Pro Pro Asp Tyr Asn Ser Val Val Leu Tyr Ser Thr Pro Pro Ile
 1325             1330                 1335

<210> SEQ ID NO 20
<211> LENGTH: 6055
<212> TYPE: DNA
<213> ORGANISM: Homo sapiens

<400> SEQUENCE: 20

```
actgagtccc gggaccccgg gagagcggtc aatgtgtggt cgctgcgttt cctctgcctg      60
cgccgggcat cacttgcgcg ccgcagaaag tccgtctggc agcctggata tcctctccta     120
ccggcacccg cagacgcccc tgcagccgcg gtcggcgccc gggctcccta gccctgtgcg     180
ctcaactgtc ctgcgctgcg gggtgccgcg agttccacct ccgcgcctcc ttctctagac     240
aggcgctggg agaaagaacc ggctcccgag ttctgggcat ttcgcccggc tcgaggtgca     300
ggatgcagag caaggtgctg ctggccgtcg ccctgtggct ctgcgtggag acccgggccg     360
cctctgtggg tttgcctagt gtttctcttg atctgcccag gctcagcata caaaaagaca     420
tacttacaat taaggctaat acaactcttc aaattacttg caggggacag agggacttgg     480
actggctttg gcccaataat cagagtggca gtgagcaaag ggtggaggtg actgagtgca     540
gcgatggcct cttctgtaag acactcacaa ttccaaaagt gatcggaaat gacactggag     600
cctacaagtg cttctaccgg gaaactgact tggcctcggt catttatgtc tatgttcaag     660
attacagatc tccatttatt gcttctgtta gtgaccaaca tggagtcgtg tacattactg     720
agaacaaaaa caaaactgtg gtgattccat gtctcgggtc catttcaaat ctcaacgtgt     780
```

```
cactttgtgc aagataccca gaaaagagat ttgttcctga tggtaacaga atttcctggg    840
acagcaagaa gggctttact attcccagct acatgatcag ctatgctggc atggtcttct    900
gtgaagcaaa aattaatgat gaaagttacc agtctattat gtacatagtt gtcgttgtag    960
ggtataggat ttatgatgtg gttctgagtc cgtctcatgg aattgaacta tctgttggag   1020
aaaagcttgt cttaaattgt acagcaagaa ctgaactaaa tgtggggatt gacttcaact   1080
gggaataccc ttcttcgaag catcagcata agaaacttgt aaaccgagac ctaaaaaccc   1140
agtctgggag tgagatgaag aaattttga gcaccttaac tatagatggt gtaacccgga   1200
gtgaccaagg attgtacacc tgtgcagcat ccagtgggct gatgaccaag aagaacagca   1260
catttgtcag ggtccatgaa aaaccttttg ttgcttttgg aagtggcatg gaatctctgg   1320
tggaagccac ggtgggggag cgtgtcagaa tccctgcgaa gtaccttggt tacccacccc   1380
cagaaataaa atggtataaa aatggaatac cccttgagtc caatcacaca attaaagcgg   1440
ggcatgtact gacgattatg gaagtgagtg aaagagacac aggaaattac actgtcatcc   1500
ttaccaatcc catttcaaag gagaagcaga gccatgtggt ctctctggtt gtgtatgtcc   1560
caccccagat tggtgagaaa tctctaatct ctcctgtgga ttcctaccag tacggcacca   1620
ctcaaacgct gacatgtacg gtctatgcca ttcctccccc gcatcacatc cactggtatt   1680
ggcagttgga ggaagagtgc gccaacgagc ccagccaagc tgtctcagtg acaaacccat   1740
acccttgtga agaatggaga agtgtggagg acttccaggg aggaaataaa attgaagtta   1800
ataaaaatca atttgctcta attgaaggaa aaacaaaac tgtaagtacc cttgttatcc   1860
aagcggcaaa tgtgtcagct ttgtacaaat gtgaagcggt caacaaagtc gggagaggag   1920
agagggtgat ctccttccac gtgaccaggg gtcctgaaat tactttgcaa cctgacatgc   1980
agcccactga gcaggagagc gtgtctttgt ggtgcactgc agacagatct acgtttgaga   2040
acctcacatg gtacaagctt ggcccacagc ctctgccaat ccatgtggga gagttgccca   2100
cacctgtttg caagaacttg gatactcttt ggaaattgaa tgccaccatg ttctctaata   2160
gcacaaatga cattttgatc atggagctta agaatgcatc cttgcaggac caaggagact   2220
atgtctgcct tgctcaagac aggaagacca agaaaagaca ttgcgtggtc aggcagctca   2280
cagtcctaga gcgtgtggca cccacgatca caggaaacct ggagaatcag acgacaagta   2340
ttggggaaag catcgaagtc tcatgcacgg catctgggaa tccccctcca cagatcatgt   2400
ggtttaaaga taatgagacc cttgtagaag actcaggcat tgtattgaag gatgggaacc   2460
ggaacctcac tatccgcaga gtgaggaagg aggacgaagg cctctacacc tgccaggcat   2520
gcagtgttct tggctgtgca aaagtggagg catttttcat aatagaaggt gcccaggaaa   2580
agacgaactt ggaaatcatt attctagtag gcacggcggt gattgccatg ttcttctggc   2640
tacttcttgt catcatccta cggaccgtta agcgggccaa tggaggggaa ctgaagacag   2700
gctacttgtc catcgtcatg gatccagatg aactcccatt ggatgaacat tgtgaacgac   2760
tgccttatga tgccagcaaa tgggaattcc ccagagaccg gctgaagcta ggtaagcctc   2820
ttggccgtgg tgcctttggc caagtgattg aagcagatgc ctttggaatt gacaagacag   2880
caacttgcag gacagtagca gtcaaaatgt tgaaagaagg agcaacacac agtgagcatc   2940
gagctctcat gtctgaactc aagatcctca ttcatattgg tcaccatctc aatgtggtca   3000
accttctagg tgcctgtacc aagcaggag ggccactcat ggtgattgtg gaattctgca   3060
aatttggaaa cctgtccact tacctgagga gcaagagaaa tgaatttgtc ccctacaaga   3120
ccaaaggggc acgattccgt caagggaaag actacgttgg agcaatccct gtggatctga   3180
```

```
aacggcgctt ggacagcatc accagtagcc agagctcagc cagctctgga tttgtggagg    3240
agaagtccct cagtgatgta gaagaagagg aagctcctga agatctgtat aaggacttcc    3300
tgaccttgga gcatctcatc tgttacagct tccaagtggc taagggcatg gagttcttgg    3360
catcgcgaaa gtgtatccac agggacctgg cggcacgaaa tatcctctta tcggagaaga    3420
acgtggttaa aatctgtgac tttggcttgg cccgggatat ttataaagat ccagattatg    3480
tcagaaaagg agatgctcgc ctcccttga aatggatggc cccagaaaca atttttgaca    3540
gagtgtacac aatccagagt gacgtctggt cttttggtgt tttgctgtgg gaaatatttt    3600
ccttaggtgc ttctccatat cctggggtaa agattgatga agaattttgt aggcgattga    3660
aagaaggaac tagaatgagg gcccctgatt atactacacc agaaatgtac cagaccatgc    3720
tggactgctg gcacggggag cccagtcaga gacccacgtt tcagagttg gtggaacatt    3780 tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa aagtaatccc agatgacaac cagacggaca    4080
gtggtatggt tcttgcctca gaagagctga aactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt ttcaagtgtt    4440
gttctttcca ccagcaggaa gtagccgcat ttgattttca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc cccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg gaaggatttg cagggctgag    4800
tctatccaag aggctttgtt taggacgtgg gtcccaagcc aagccttaag tgtggaattc    4860
ggattgatag aaaggaagac taacgttacc ttgctttgga gagtactgga gcctgcaaat    4920
gcattgtgtt tgctctggtg gaggtgggca tggggtctgt tctgaaatgt aaagggttca    4980
gacggggttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttaccctttt gttcttcccc ctgtccccaa cccactctca ccccgcaacc    5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga tttttgccct tgttctgtcc    5580
```

-continued

```
tttttttcaa aaagaaaat gtgttttttg tttggtacca tagtgtgaaa tgctgggaac      5640
aatgactata agacatgcta tggcacatat atttatagtc tgtttatgta gaaacaaatg      5700
taatatatta aagccttata tataatgaac tttgtactat tcacattttg tatcagtatt      5760
atgtagcata acaaaggtca taatgctttc agcaattgat gtcattttat aaagaacat       5820 tgaaaaactt gaaggaatcc ctttgcaagg ttgcattact gtacccatca tttctaaaat      5880
ggaagagggg gtggctgggc acagtggccg acacctaaaa acccagcact ttgggggggcc    5940 aaggtgggag gatcgcttga gcccaggagt tcaagaccag tctggccaac atggtcagat      6000
tccatctcaa agaaaaaagg taaaaataaa ataaaatgga gaagaaggaa tcaga           6055
```

<210> SEQ ID NO 21
<211> LENGTH: 1356
<212> TYPE: PRT
<213> ORGANISM: Homo sapiens

<400> SEQUENCE: 21

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285
```

```
Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
690                 695                 700
```

```
Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
            725                 730                 735

Cys Gln Ala Cys Ser Val Leu Gly Cys Ala Lys Val Glu Ala Phe Phe
        740                 745                 750

Ile Ile Glu Gly Ala Gln Glu Lys Thr Asn Leu Glu Ile Ile Ile Leu
    755                 760                 765

Val Gly Thr Ala Val Ile Ala Met Phe Phe Trp Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
        820                 825                 830

Arg Leu Lys Leu Gly Lys Pro Leu Gly Arg Gly Ala Phe Gly Gln Val
    835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
        900                 905                 910

Met Val Ile Val Glu Phe Cys Lys Phe Gly Asn Leu Ser Thr Tyr Leu
    915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Ala Pro
        980                 985                 990

Glu Asp Leu Tyr Lys Asp Phe Leu Thr Leu Glu His Leu Ile Cys Tyr
    995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110
```

```
Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 22
<211> LENGTH: 9
<212> TYPE: PRT
<213> ORGANISM: Artificial
<220> FEATURE:
<223> OTHER INFORMATION: an HIV-Env protein-derived synthesized peptide

<400> SEQUENCE: 22

Arg Tyr Leu Arg Asp Gln Gln Leu Leu
1               5

<210> SEQ ID NO 23
<211> LENGTH: 9
<212> TYPE: PRT
<213> ORGANISM: Artificial
<220> FEATURE:
<223> OTHER INFORMATION: an HIV-Env protein-derived synthesized peptide

<400> SEQUENCE: 23

Ser Leu Tyr Asn Thr Tyr Ala Thr Leu
1               5
```